US011559525B2

(12) United States Patent
Kurita et al.

(10) Patent No.: US 11,559,525 B2
(45) Date of Patent: *Jan. 24, 2023

(54) THERAPEUTIC DRUG FOR DYSKINESIA

(71) Applicant: Sumitomo Pharma Co., Ltd., Osaka (JP)

(72) Inventors: Mitsumasa Kurita, Osaka (JP); Yuki Ikeda, Osaka (JP); Mitsuhiro Nakato, Osaka (JP)

(73) Assignee: SUMITOMO PHARMA CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/461,015

(22) Filed: Aug. 30, 2021

(65) Prior Publication Data

US 2021/0386739 A1 Dec. 16, 2021

Related U.S. Application Data

(63) Continuation-in-part of application No. 16/855,213, filed on Apr. 22, 2020, which is a continuation of application No. 16/395,531, filed on Apr. 26, 2019, now Pat. No. 10,758,535.

(30) Foreign Application Priority Data

Aug. 31, 2020 (JP) .............................. JP2020-145967

(51) Int. Cl.
| | |
|---|---|
| A61K 31/506 | (2006.01) |
| A61K 31/4015 | (2006.01) |
| A61K 9/00 | (2006.01) |
| A61P 25/14 | (2006.01) |
| A61K 31/198 | (2006.01) |
| A61P 25/16 | (2006.01) |
| A61K 9/70 | (2006.01) |
| A61K 31/496 | (2006.01) |

(52) U.S. Cl.
CPC .......... *A61K 31/506* (2013.01); *A61K 9/0014* (2013.01); *A61K 9/0019* (2013.01); *A61K 9/7023* (2013.01); *A61K 31/198* (2013.01); *A61K 31/4015* (2013.01); *A61K 31/496* (2013.01); *A61P 25/16* (2018.01)

(58) Field of Classification Search
CPC .... A61K 31/506; A61K 31/4015; A61K 9/00; A61P 25/14

See application file for complete search history.

(56) References Cited

U.S. PATENT DOCUMENTS

| 4,507,303 | A | 3/1985 | Ishizumi |
| 5,817,331 | A | 10/1998 | Kenealy et al. |
| 10,758,535 | B1 | 9/2020 | Kurita |
| 2006/0110434 | A1 | 5/2006 | Yamaguchi |
| 2006/0193900 | A1 | 8/2006 | Yasukochi |
| 2007/0232629 | A1 | 10/2007 | Yamaguchi |
| 2014/0243350 | A1 | 8/2014 | Hansen |
| 2021/0060015 | A1 | 3/2021 | Kurita |

FOREIGN PATENT DOCUMENTS

| EP | 1743645 | 1/2007 |
| JP | 11-228414 | 8/1999 |
| WO | WO2008044336 | 4/2008 |
| WO | WO2013156035 | 10/2013 |
| WO | WO2020127954 | 6/2020 |
| WO | WO2021166987 | 8/2021 |

OTHER PUBLICATIONS

Huang et al., "Role of tandospirone, a 5-HT1A receptor partial agonist, in the treatment of central nervous system disorders and underlying mechanisms," Oncotarget 8(60):102705-102270 (2017).
Hikiji et al., "A case of tandospirone citrate responsive Parkinson's disease with psychotic symptoms and diurnal fluctuation," Japanese Journal of Psychiatric Treatment, 14(11):1271-1274 (1999) (Abstract Translation).
Iderberg et al., "Activity of serotonin 5-HT(1A) receptor 'biased agonists' in rat models of Parkinson's disease and L-DOPA-induced dyskinesia.," Neuropharmacology, 93:52-67 (2015).
Ishibashi et al., "Antiparkinsonian actions of a selective 5-HT1A agonist, tandospirone, in rats," Advances in Neuroregulation and Neuroprotection; 369-378 (2005).
Ishibashi et al., "Antiparkinsonian actions of a selective 5-HT1A agonist, tandospirone, in rats," Biogenic Amines 18(3-6):329-338 (2004).
Ishibashi et al., "Effect of a selective 5-HT1A agonist tandospirone on abnormal involuntary movements in rat L-DOPA-induced dyskinesia model," Journal of Pharmacological Sciences, 101:110 (2006).
Kannari et al., "Tandospirone citrate, a selective 5-HT1A agonist, alleviates L-DOPA-induced dyskinesia in patients with Parkinson's disease," Brain Nerve 54(2):133-137 (2002) (Abstract Translation).
Kitanaka et al., "Decreased striatal dopamine level accompanied by the increase in the duration of the stereotypy after treatment with 2-phenylethylamine in combination with 1-deprenyl in mice," Journal of Pharmacological Sciences, 100:192 (2006).
Matsubara et al., "Tandospirone, a 5-HT1A agonist, ameliorates movement disorder via non-dopaminergic systems in rats with unilateral 6-hydroxydopamine-generated lesions," Brain Research 1112(1):126-133 (2006).
Nomoto et al., "A 5-HT1A receptor agonist, tandospirone improves gait disturbance of patients with Parksinson's disease," The Journal of Movement Disorder and Disability 7(2):65-70 (1997) (Abstract Translation).

(Continued)

*Primary Examiner* — Samira J Jean-Louis
(74) *Attorney, Agent, or Firm* — Haley Guiliano LLP; James F. Haley, Jr.; Brian M. Gummow

(57) ABSTRACT

The present invention provides a therapeutic drug that is useful for levodopa induced dyskinesia in Parkinson's disease. In particular, the present invention provides a composition and method for treating, improving, delaying the progression, or preventing motor complications associated with levodopa therapy for Parkinson's disease, especially levodopa induced dyskinesia (PD-LID), comprising tandospirone or a pharmaceutically acceptable salt or prodrug thereof, wherein the tandospirone or a pharmaceutically acceptable salt or prodrug thereof is parenterally administered.

29 Claims, 29 Drawing Sheets

(56) References Cited

OTHER PUBLICATIONS

Yoshino et al., "Tandospirone potentiates the fluoxetine-induced increases in extracellular dopamine via 5-HT(1A) receptors in the rat medial frontal cortex," Neurochemistry International, 40(4):355-360 (2002).

Jankovic et al., "Parkinson's disease: etiopathogenesis and treatment", J. Neurol. Neurosurg. Psychiatry, 91:795-808 (2020).

A

B

C

A

B

C

A

B

C

A

B

A

B

C

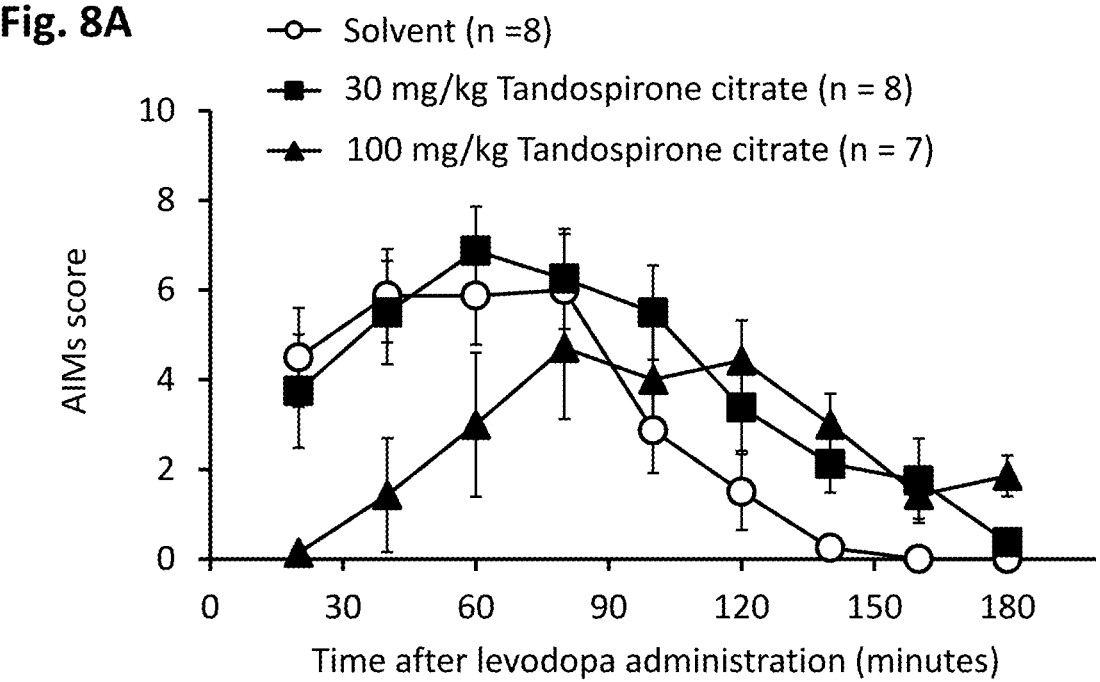

A

B

C

*: $p < 0.05$,
**: $p < 0.01$, Steel's test (vs. solvent)

**: $p < 0.01$, Steel's test (vs. solvent)

THERAPEUTIC DRUG FOR DYSKINESIA

CROSS REFERENCE TO RELATED APPLICATIONS

This application is a continuation-in-part of U.S. patent application Ser. No. 16/855,213 (pending), filed Apr. 22, 2020, which is a continuation of U.S. patent application Ser. No. 16/395,531, filed Apr. 26, 2019, now U.S. Pat. No. 10,758,535. This application also claims priority pursuant to 35 U.S.C. § 119 to Japanese Patent Application No. 2020-145967, filed Aug. 31, 2020. The contents of each of these documents are each hereby incorporated by reference in their entirety.

TECHNICAL FIELD

The present invention relates to a formulation for treating levodopa induced dyskinesia in Parkinson's disease by parenteral administration (e.g., transdermal administration), comprising tandospirone or a pharmaceutically acceptable salt or prodrug thereof that is useful as a medicament as an active ingredient.

BACKGROUND ART

Parkinson's disease is a progressive neurodegenerative disease with a primary symptom of extrapyramidal function abnormality. Pathologically, loss of dopaminergic neurons and alpha-synuclein deposition in the substantia nigra pars compacta are observed. Clinically, various motor symptoms such as akinesia, tremor, rigidity, and loss of postural reflexes are exhibited.

Parkinson's disease therapy is fundamentally a drug therapy intended to supplement intracerebral dopamine. A drug comprising levodopa (L-dopa), which is a dopamine precursor, is used as the first-line drug for the initial therapy of Parkinson's disease. However, motor complications such as Parkinson's Disease Levodopa induced dyskinesia (hereinafter, also referred to as "PD-LID") are manifested in almost all patients undergoing levodopa therapy with the progression in pathological conditions.

The frequency of developing PD-LID in 5 years after the initial levodopa therapy is 30 to 50%. The frequency increases with the progression of the pathological condition and reaches 50 to 100% in 10 years after the initial therapy. Peak-dose dyskinesia is known as an exemplary symptom of PD-LID, which is an involuntary movement manifested in the face, tongue, neck, limbs, body trunk, or the like when the blood levodopa concentration is high.

Patent Literature 1 [Japanese Laid-Open Publication No. 11-228414] has a disclosure on transdermally absorbed tandospirone agents.

CITATION LIST

Patent Literature

[Patent Literature 1] Japanese Laid-Open Publication No. 11-228414

SUMMARY OF INVENTION

Solution to Problem

As a result of diligent studies, the inventors have discovered that a useful technology for treatment, improvement, delay of progression, or prevention with a high effect of improving of Parkinson's disease levodopa induced dyskinesia (PD-LID) or the like can be provided, as compared to oral administration, by parenterally administering (e.g., transdermal administration, intradermal administration, subcutaneous administration, intramuscular administration, or the like) tandospirone or a pharmaceutically acceptable salt or prodrug thereof. The present invention provides transdermally administered pharmaceutical compositions for improving PD-LID, comprising tandospirone or a pharmaceutically acceptable salt or prodrug thereof, and methods of treating, improving, delaying the progression, and preventing motor complications of Parkinson's disease by parenteral administration including tandospirone or a pharmaceutically acceptable salt or prodrug thereof.

It is also critical to control non-motor symptoms in therapy of Parkinson's disease or the like. The composition of the present disclosure also has an advantage of having no adverse effect on non-motor symptoms in the treatment of motor complications such as improvement of dyskinesia in comparison to other therapeutic drugs (e.g., extended release amantadine formulation or the like) for motor symptoms in Parkinson's disease. Depending on the patient, an improvement in non-motor symptoms can also be expected in addition to an effect of improving motor complications such as improving dyskinesia and motor fluctuations.

Examples of the non-motor symptoms include psychiatric symptoms, sleep disorders, sensory disturbance, pain, olfactory dysfunction, autonomic nervous system symptoms, and the like. Examples of psychiatric symptoms include depression, anxiety, apathy, excitation, irascibility, hallucination, delusion, cognitive dysfunction, and the like. Examples of sleep disorders include daytime hypersomnia, insomnia, restless legs syndrome, REM sleep behavior disorder, and the like. Examples of autonomic nervous system symptoms include constipation, dysuria, orthostatic hypotension, and the like.

The composition of the present disclosure is expected not to exacerbate especially depression, anxiety, irascibility, restless legs syndrome, REM sleep behavior disorder, or hallucination, and is expected to have an effect of improving depression, anxiety, irascibility, restless legs syndrome, or REM sleep behavior disorder in comparison to other therapeutic drugs (e.g., extended release amantadine formulation or the like) for motor symptoms in Parkinson's disease.

Specifically, the present invention comprises the following.

X1. A method for treating, improving, delaying the progression, or preventing dyskinesia in a subject, comprising parenterally administering to the subject an effective amount of tandospirone or a pharmaceutically acceptable salt or prodrug thereof, wherein the tandospirone or a pharmaceutically acceptable salt or prodrug thereof is administered so that a human blood (plasma) tandospirone concentration is 0.1 to 15 ng/mL for 12 hours or longer per day; and/or 0.1 to 15 ng/mL for 8 to 16 hours after administration of the tandospirone or a pharmaceutically acceptable salt or prodrug thereof.

X2. The method according to any one of preceding Items, wherein the patient is suffered from Parkinson's disease.

X3. The method according to any one of preceding Items, wherein the subject is subject to a drug therapy of Parkinson's disease.

X4. The method according to any one of preceding Items, wherein the subject is subject to a drug therapy of Parkinson's disease, wherein the drug therapy is at least one selected from the group consisting of Parkinson's disease drug therapy such as levodopa therapy, a therapy with levodopa metabolism enzyme inhibitor and Dopamine receptor agonist; and Parkinson's disease adjunct.

X5. The method according to any one of preceding Items, wherein the subject is subject to a drug therapy of Parkinson's disease, wherein the drug therapy is at least one selected from the group consisting of dopamine replacement therapies such as levodopa therapy, a therapy with levodopa metabolism enzyme inhibitor and a dopamine receptor agonist.

X6 The method according to any one of preceding Items, wherein the subject is subject to a drug therapy of Parkinson's disease, wherein the drug therapy is at least one selected from the group consisting of levodopa therapies such as therapy with levodopa containing formulation, and a therapy with levodopa metabolism enzyme inhibitor and a dopamine receptor agonist.

X7. The method according to any one of preceding Items, wherein dopamine amount in striatal synaptic cleft of the subject is sustainably maintained and/or suppressing rapid changes.

X8. The method according to any one of preceding Items, wherein the administration is performed without inducing rebound symptoms in the subject.

X9. The method according to any one of preceding Items, wherein a levodopa-evoked synaptic dopamine fluxes in the striatum of the subject using $^{11}$C-raclopride Positron Emission Tomography (PET) test is sustainably maintained, and/or suppressing rapid changes and/or intermittent domain receptor stimulation is suppressed.

X10. The method of any one of preceding Items, wherein the parenteral administration comprises transdermal administration.

X11. The method of any one of preceding Items, wherein the treatment, improvement, delay of progression, or prevention improves dyskinesia without a rebound symptom.

X12. The method of any one of preceding Items, wherein the dyskinesia comprises at least one of the group consisting of peak-dose dyskinesia, diphasic dyskinesia, and a combination thereof.

X13. The method of any one of preceding Items, wherein the treatment, improvement, delay of progression, or prevention of dyskinesia comprises improvement, delay of progression, or prevention of a dyskinesia symptom, reduction of a period of PD-LID manifestation, or a combination thereof.

X14. The method of any one of preceding Items3, wherein the improvement of a dyskinesia symptom is a clinically significant improvement or greater.

X15. The method of any one of preceding Items3, wherein the improvement of a dyskinesia symptom is to a sufficient level to attain a clinical effect.

X16. The method of any one of preceding Items, wherein the tandospirone or a pharmaceutically acceptable salt or prodrug thereof is provided as a transdermally administered formulation.

X17. The method of any one of preceding Items, wherein the tandospirone or a pharmaceutically acceptable salt or prodrug thereof is provided as an adhesive formulation.

X18. The method of any one of preceding Items0, wherein the transdermally administered formulation is a tape/patch.

X19. The method of any one of preceding Items, wherein a drug dosage of the tandospirone or a pharmaceutically acceptable salt or prodrug thereof is 0.1 to 100 mg per day as a free form of tandospirone.

X20. The method of any one of preceding Items, wherein an amount of drug penetration for the tandospirone or a pharmaceutically acceptable salt or prodrug thereof is 0.1 to 20 mg per day as a free form of tandospirone.

X21. The method of any one of preceding Items, wherein the tandospirone or a pharmaceutically acceptable salt or prodrug thereof is provided as a transdermally administered formulation, and a total applied area per dose is 1 to 100 cm$^2$.

X22. The method of any one of preceding Items, wherein the human blood (plasma) tandospirone concentration is 1 to 12 ng/mL 23 The method of any one of preceding Items, wherein the human blood (plasma) tandospirone concentration is 2 to 10 ng/mL.

X24. The method of any one of preceding Items, wherein the tandospirone or a pharmaceutically acceptable salt or prodrug thereof is an adjunct of levodopa.

X25. The method of any one of preceding Items, wherein the tandospirone or a pharmaceutically acceptable salt or prodrug thereof is used with levodopa as the fixed-dose combination or concomitantly as separate formulations.

X26. The method according to any one of preceding Items, wherein the method further improves motor fluctuations in the subject.

X27. The method according to any one of preceding Items, wherein the motor fluctuations comprise at least one of the group consisting of a wearing-off phenomenon, an on-off phenomenon, a no-on phenomenon, a delayed on phenomenon, and a combination thereof.

X28. The method according to any one of preceding Items, wherein treatment, improvement, or prevention of the motor fluctuations comprises prolongation of an antiparkinsonian action effective time (ON-time), a reduction of a non-response time (OFF-time), or a combination thereof.

x29. The method of any one of preceding Items, wherein the tandospirone or a pharmaceutically acceptable salt thereof is administered so that a maximum blood concentration of human blood (plasma) tandospirone in a steady state is 1 to 15 ng/mL, and a ratio of a minimum concentration, with respect to the maximum concentration of human blood (plasma) tandospirone concentration as 100%, is 30 to 95% after administration of the tandospirone or a pharmaceutically acceptable salt thereof.

X30. The method of any one of preceding Items, wherein the tandospirone or a pharmaceutically acceptable salt thereof is administered so that a maximum blood concentration of human blood (plasma) tandospirone in a steady state is 2 to 12 ng/mL, and a ratio of a minimum concentration, with respect to the maximum concentration of human blood (plasma) tandospirone concentration as 100%, is 30 to 95% after administration of the tandospirone or a pharmaceutically acceptable salt thereof.

[Item 1A]

A composition for treating, improving, delaying the progression, or preventing motor complications associated with Parkinson's disease, comprising tandospirone or a pharmaceutically acceptable salt or prodrug thereof, wherein the tandospirone or a pharmaceutically acceptable salt or prodrug thereof is parenterally administered.

[Item 1B]

A composition for treating, improving, delaying the progression, or preventing motor complications associated with a drug therapy for Parkinson's disease, comprising tandospirone or a pharmaceutically acceptable salt or prodrug thereof, wherein the tandospirone or a pharmaceutically acceptable salt or prodrug thereof is parenterally administered.

[Item 1]
A composition for treating, improving, delaying the progression, or preventing motor complications associated with levodopa therapy for Parkinson's disease, comprising tandospirone or a pharmaceutically acceptable salt or prodrug thereof, wherein the tandospirone or a pharmaceutically acceptable salt or prodrug thereof is parenterally administered.

[Item 2]
The composition of any one of the preceding items, wherein the parenteral administration is selected from transdermal administration, intradermal administration, subcutaneous administration, intramuscular administration, and a combination thereof.

[Item 3]
The composition of any one of the preceding items, wherein the parenteral administration has sustainability or is sustainably administered.

[Item 4]
The composition of any one of the preceding items, wherein the parenteral administration comprises transdermal administration.

[Item 5]
The composition of any one of the preceding items, wherein the motor complications comprise levodopa induced dyskinesia (PD-LID).

[Item 6]
A composition for treating, improving, or preventing motor complications associated with levodopa therapy for Parkinson's disease, comprising tandospirone or a pharmaceutically acceptable salt or prodrug thereof, wherein levodopa induced dyskinesia (PD-LID) is improved without resulting in a rebound symptom, and wherein the tandospirone or a pharmaceutically acceptable salt or prodrug thereof is transdermally administered.

[Item 7]
The composition of any one of the preceding items, wherein levodopa induced dyskinesia (PD-LID) comprises peak-dose dyskinesia, diphasic dyskinesia, and a combination thereof.

[Item 8]
The composition of any one of the preceding items, wherein the treatment, improvement, delay of progression, or prevention of motor complications comprises improvement, delay of progression, or prevention of a levodopa induced dyskinesia (PD-LID) symptom, reduction of a period of levodopa induced dyskinesia (PD-LID) manifestation, or a combination thereof.

[Item 9]
A composition for accomplishing improvement, delay of progression, or prevention of a levodopa induced dyskinesia (PD-LID) symptom, reduction of a period of levodopa induced dyskinesia (PD-LID) manifestation, or a combination thereof, comprising tandospirone or a pharmaceutically acceptable salt or prodrug thereof, wherein the tandospirone or a pharmaceutically acceptable salt or prodrug thereof is parenterally administered.

[Item 10]
The composition of any one of the preceding items, wherein the improvement of a levodopa induced dyskinesia (PD-LID) symptom is a clinically significant improvement or greater.

[Item 11]
The composition of any one of the preceding items, wherein the improvement a levodopa induced dyskinesia (PD-LID) symptom is to a sufficient level to attain a clinical effect.

[Item 12]
The composition of any one of the preceding items, wherein the composition is a transdermally administered formulation.

[Item 13]
The composition of any one of the preceding items, wherein the composition is an adhesive formulation.

[Item 14]
The composition of any one of the preceding items, wherein a transdermally administered formulation is a tape/patch.

[Item 15]
The composition of any one of the preceding items, wherein a drug dosage of the tandospirone or a pharmaceutically acceptable salt or prodrug thereof is 0.1 to 100 mg per day as a free form of tandospirone.

[Item 16]
The composition of any one of the preceding items, wherein an amount of drug penetration for the tandospirone or a pharmaceutically acceptable salt or prodrug thereof is 0.1 to 20 mg per day as a free form of tandospirone.

[Item 17]
The composition of any one of the preceding items, wherein the composition is a transdermally administered formulation, and a total applied area per dose is 1 to 100 $cm^2$.

[Item 18]
The composition of any one of the preceding items, wherein the tandospirone or a pharmaceutically acceptable salt or prodrug thereof is administered so that a human blood (plasma) tandospirone concentration is 0.05 to 20 ng/mL for 12 hours or longer per day.

[Item 19]
The composition of any one of the preceding items, wherein the tandospirone or a pharmaceutically acceptable salt or prodrug thereof is administered so that a human blood (plasma) tandospirone concentration is 0.05 to 20 ng/mL for 8 to 16 hours after administration of the tandospirone or a pharmaceutically acceptable salt or prodrug thereof.

[Item 20]
The composition of any one of the preceding items, wherein the tandospirone or a pharmaceutically acceptable salt or prodrug thereof is an adjunct of levodopa.

[Item 21]
The composition of any one of the preceding items, which is used with levodopa as the fixed-dose combination or concomitantly as separate formulations.

[Item 22]
A medicament for treating or preventing Parkinson's disease without accompanying or by minimizing PD-LID, comprising a combination of tandospirone or a pharmaceutically acceptable salt or prodrug thereof and (1) levodopa or (2) levodopa and a metabolizing enzyme inhibitor of levodopa, wherein the tandospirone or a pharmaceutically acceptable salt or prodrug thereof is parenterally administered.

[Item 23]
A medicament for treating or preventing Parkinson's disease without accompanying or by minimizing PD-LID, comprising tandospirone or a pharmaceutically acceptable salt or prodrug thereof, wherein the tandospirone or a pharmaceutically acceptable salt or prodrug thereof is administered in combination with (1) levodopa or (2) levodopa and a metabolizing enzyme inhibitor of levodopa, wherein the tandospirone or a pharmaceutically acceptable salt or prodrug thereof is parenterally administered.

[Item 24]
A medicament for treating or preventing Parkinson's disease without accompanying or by minimizing PD-LID, comprising (1) levodopa or (2) levodopa and a metabolizing enzyme inhibitor of levodopa, wherein the (1) levodopa or (2) levodopa and a metabolizing enzyme inhibitor of levodopa is administered in combination with tandospirone or a pharmaceutically acceptable salt or prodrug thereof, wherein the tandospirone or a pharmaceutically acceptable salt or prodrug thereof is parenterally administered.

[Item 25]
A composition for improving the exacerbation in quality of response to levodopa therapy of a Parkinson's disease patient with dyskinesia, comprising tandospirone or a pharmaceutically acceptable salt or prodrug thereof, wherein the tandospirone or a pharmaceutically acceptable salt or prodrug thereof is parenterally administered.

[Item 26]
The medicament or composition of any one of the preceding items, wherein the tandospirone or a pharmaceutically acceptable salt or prodrug thereof is a free form of tandospirone.

[Item 1A-1]
A method for treating, improving, or preventing motor complications associated with Parkinson's disease, comprising parenterally administering an effective amount of tandospirone or a pharmaceutically acceptable salt or prodrug thereof to a subject.

[Item 1A-2]
A method for treating, improving, or preventing motor complications associated with a drug therapy for Parkinson's disease, comprising parenterally administering an effective amount of tandospirone or a pharmaceutically acceptable salt or prodrug thereof to a subject.

[Item 1A]
A method for treating, improving, or preventing motor complications associated with levodopa therapy for Parkinson's disease, comprising parenterally administering an effective amount of tandospirone or a pharmaceutically acceptable salt or prodrug thereof to a subject.

[Item 2A]
The method of any one of the preceding items, wherein the parenteral administration is selected from transdermal administration, intradermal administration, subcutaneous administration, intramuscular administration, and a combination thereof.

[Item 3A]
The method of any one of the preceding items, wherein the parenteral administration has sustainability or is sustainably administered.

[Item 4A]
The method of any one of the preceding items, wherein the parenteral administration comprises transdermal administration.

[Item 5A]
The method of any one of the preceding items, wherein the motor complications comprise levodopa induced dyskinesia (PD-LID).

[Item 6A]
A method of treating, improving, or preventing motor complications associated with levodopa therapy for Parkinson's disease, comprising transdermally administering an effective amount of tandospirone or a pharmaceutically acceptable salt or prodrug thereof to a subject, such that levodopa induced dyskinesia (PD-LID) is improved without a rebound symptom.

[Item 7A]
The method of any one of the preceding items, wherein levodopa induced dyskinesia (PD-LID) comprises peak-dose dyskinesia, diphasic dyskinesia, and a combination thereof.

[Item 8A]
The method of any one of the preceding items, wherein the treatment, improvement, delay of progression, or prevention of motor complications comprises improvement, delay of progression, or prevention of a levodopa induced dyskinesia (PD-LID) symptom, reduction of a period of levodopa induced dyskinesia (PD-LID) manifestation, or a combination thereof.

[Item 9A]
A method for accomplishing improvement, delay of progression, or prevention of a levodopa induced dyskinesia (PD-LID) symptom, reduction of a period of levodopa induced dyskinesia (PD-LID) manifestation, or a combination thereof, comprising parenterally administering an effective amount of tandospirone or a pharmaceutically acceptable salt or prodrug thereof to a subject.

[Item 10A]
The method of any one of the preceding items, wherein the improvement of a levodopa induced dyskinesia (PD-LID) symptom is a clinically significant improvement or greater.

[Item 11A]
The method of any one of the preceding items, wherein the improvement of a levodopa induced dyskinesia (PD-LID) symptom is to a sufficient level to attain a clinical effect.

[Item 12A]
The method of any one of the preceding items, wherein the tandospirone or a pharmaceutically acceptable salt or prodrug thereof is provided as a transdermally administered formulation.

[Item 13A]
The method of any one of the preceding items, wherein the tandospirone or a pharmaceutically acceptable salt or prodrug thereof is provided as an adhesive formulation.

[Item 14A]
The method of any one of the preceding items, wherein the transdermally administered formulation is a tape/patch.

[Item 15A]
The method of any one of the preceding items, wherein a drug dosage of the tandospirone or a pharmaceutically acceptable salt or prodrug thereof is 0.1 to 100 mg per day as a free form of tandospirone.

[Item 16A]
The method of any one of the preceding items, wherein an amount of drug penetration for the tandospirone or a pharmaceutically acceptable salt or prodrug thereof is 0.1 to 20 mg per day as a free form of tandospirone.

[Item 17A]
The method of any one of the preceding items, wherein the administration is accomplished with a transdermally administered formulation, and a total applied area per dose is 1 to 100 cm$^2$.

[Item 18A]
The method of any one of the preceding items, wherein the tandospirone or a pharmaceutically acceptable salt or prodrug thereof is administered so that a human blood (plasma) tandospirone concentration is 0.05 to 20 ng/mL for 12 hours or longer per day.

[Item 19A]
The method of any one of the preceding items, wherein the tandospirone or a pharmaceutically acceptable salt or prodrug thereof is administered so that a human blood (plasma) tandospirone concentration is 0.05 to 20 ng/mL for 8 to 16 hours after administration of the tandospirone or a pharmaceutically acceptable salt or prodrug thereof.

[Item 20A]

The method of any one of the preceding items, wherein the tandospirone or a pharmaceutically acceptable salt or prodrug thereof is an adjunct of levodopa.

[Item 21A]

The method of any one of the preceding items, wherein the tandospirone or a pharmaceutically acceptable salt or prodrug thereof is used with levodopa as the fixed-dose combination or concomitantly as separate formulations.

[Item 22A]

A method for treating or preventing Parkinson's disease without accompanying or by minimizing PD-LID in a subject, comprising administering to the subject an effective amount of a combination of an effective amount of tandospirone or a pharmaceutically acceptable salt or prodrug thereof and (1) an effective amount of levodopa or (2) levodopa and a metabolizing enzyme inhibitor of levodopa, wherein the effective amount of tandospirone or a pharmaceutically acceptable salt or prodrug thereof is parenterally administered.

[Item 23A]

The method of any one of the preceding items, wherein the tandospirone or a pharmaceutically acceptable salt or prodrug thereof and the (1) or (2) are administered simultaneously or at different times.

[Item 24A]

A composition for improving the exacerbation in quality of response to levodopa therapy of a Parkinson's disease patient with dyskinesia, comprising tandospirone or a pharmaceutically acceptable salt or prodrug thereof, wherein an effective amount of the tandospirone or a pharmaceutically acceptable salt or prodrug thereof is parenterally administered.

[Item 25A]

The method of any one of the preceding items, wherein the tandospirone or a pharmaceutically acceptable salt thereof is a free form of tandospirone.

[Item 1B]

Use of tandospirone or a pharmaceutically acceptable salt or prodrug thereof in the manufacture of a medicament for treating, improving, or preventing motor complications associated with levodopa therapy for Parkinson's disease, wherein the medicament is parenterally administered.

[Item 2B]

The use of any one of the preceding items, wherein the parenteral administration is selected from transdermal administration, intradermal administration, subcutaneous administration, intramuscular administration, and a combination thereof.

[Item 3B]

The use of any one of the preceding items, wherein the parenteral administration has sustainability or is sustainably administered.

[Item 4B]

The use of any one of the preceding items, wherein the parenteral administration comprises transdermal administration.

[Item 5B]

The use of any one of the preceding items, wherein the motor complications comprise levodopa induced dyskinesia (PD-LID).

[Item 6B]

Use in the manufacture of a medicament comprising tandospirone or a pharmaceutically acceptable salt or prodrug thereof for the treatment, improvement, or prevention of motor complications associated with levodopa therapy for Parkinson's disease, wherein levodopa induced dyskinesia (PD-LID) is improved without resulting in a rebound symptom, and wherein the tandospirone or a pharmaceutically acceptable salt or prodrug thereof is transdermally administered.

[Item 7B]

The use of any one of the preceding items, wherein levodopa induced dyskinesia (PD-LID) comprises peak-dose dyskinesia, diphasic dyskinesia, and a combination thereof.

[Item 8B]

The use of any one of the preceding items, wherein the treatment, improvement, delay of progression, or prevention of motor complications comprises improvement, delay of progression, or prevention of a levodopa induced dyskinesia (PD-LID) symptom, reduction of a period of levodopa induced dyskinesia (PD-LID) manifestation, or a combination thereof.

[Item 9B]

Use in the manufacture of a medicament comprising tandospirone or a pharmaceutically acceptable salt or prodrug thereof for accomplishing the improvement, delay of progression, or prevention of a levodopa induced dyskinesia (PD-LID) symptom, reduction of a period of levodopa induced dyskinesia (PD-LID) manifestation, or a combination thereof, wherein the tandospirone or a pharmaceutically acceptable salt or prodrug thereof is parenterally administered.

[Item 10B]

The use of any one of the preceding items, wherein the improvement of a levodopa induced dyskinesia (PD-LID) symptom is a clinically significant improvement or greater.

[Item 11B]

The use of any one of the preceding items, wherein the improvement of a levodopa induced dyskinesia (PD-LID) symptom is to a sufficient level to attain a clinical effect.

[Item 12B]

The use of any one of the preceding items, wherein the medicament is a transdermally administered formulation.

[Item 13B]

The use of any one of the preceding items, wherein the medicament is an adhesive formulation.

[Item 14B]

The use of any one of the preceding items, wherein the transdermally administered formulation is a tape/patch.

[Item 15B]

The use of any one of the preceding items, wherein a drug dosage of the tandospirone or a pharmaceutically acceptable salt or prodrug thereof is 0.1 to 100 mg per day as a free form of tandospirone.

[Item 16B]

The use of any one of the preceding items, wherein an amount of drug penetration for the tandospirone or a pharmaceutically acceptable salt or prodrug thereof is 0.1 to 20 mg per day as a free form of tandospirone.

[Item 17B]

The use of any one of the preceding items, wherein the medicament is a transdermally administered formulation, and a total applied area per dose is 1 to 100 cm$^2$.

[Item 18B]

The use of any one of the preceding items, wherein the tandospirone or a pharmaceutically acceptable salt or prodrug thereof is administered so that a human blood (plasma) tandospirone concentration is 0.05 to 20 ng/mL for 12 hours or longer per day.

[Item 19B]

The use of any one of the preceding items, wherein the tandospirone or a pharmaceutically acceptable salt or prodrug thereof is administered so that a human blood (plasma) tandospirone concentration is 0.05 to 20 ng/mL for 8 to 16 hours after administration of the tandospirone or a pharmaceutically acceptable salt or prodrug thereof.

[Item 20B]

The use of any one of the preceding items, wherein the tandospirone or a pharmaceutically acceptable salt or prodrug thereof is an adjunct of levodopa.

[Item 21B]

The use of any one of the preceding items, wherein the medicament is used with levodopa as the fixed-dose combination or concomitantly as separate formulations.

[Item 22B]

Use in the manufacture of a medicament for treating or preventing Parkinson's disease without accompanying or by minimizing PD-LID, wherein the medicament comprises a combination of tandospirone or a pharmaceutically acceptable salt or prodrug thereof and (1) levodopa or (2) levodopa and a metabolizing enzyme inhibitor of levodopa, wherein the tandospirone or a pharmaceutically acceptable salt or prodrug thereof is parenterally administered.

[Item 23B]

Use in the manufacture of a medicament for treating or preventing Parkinson's disease without accompanying or by minimizing PD-LID, wherein the medicament comprises tandospirone or a pharmaceutically acceptable salt or prodrug thereof, wherein the tandospirone or a pharmaceutically acceptable salt or prodrug thereof is administered in combination with (1) levodopa or (2) levodopa and a metabolizing enzyme inhibitor of levodopa, wherein the tandospirone or a pharmaceutically acceptable salt or prodrug thereof is parenterally administered.

[Item 24B]

Use in the manufacture of a medicament for treating or preventing Parkinson's disease without accompanying or by minimizing PD-LID, wherein the medicament comprises (1) levodopa or (2) levodopa and a metabolizing enzyme inhibitor of levodopa, wherein the (1) levodopa or (2) levodopa and a metabolizing enzyme inhibitor of levodopa is administered in combination with tandospirone or a pharmaceutically acceptable salt or prodrug thereof, and wherein the tandospirone or a pharmaceutically acceptable salt or prodrug thereof is parenterally administered.

[Item 25B]

Use in the manufacture of a medicament comprising tandospirone or a pharmaceutically acceptable salt or prodrug thereof for improving the exacerbation in quality of response to levodopa therapy of a Parkinson's disease patient with dyskinesia, wherein the tandospirone or a pharmaceutically acceptable salt or prodrug thereof is parenterally administered.

[Item 26B]

The use of any one of the preceding items, wherein the tandospirone or a pharmaceutically acceptable salt thereof is a free form of tandospirone.

[Item 1C]

Tandospirone or a pharmaceutically acceptable salt or prodrug thereof for treating, improving, or preventing motor complications associated with levodopa therapy for Parkinson's disease, wherein the tandospirone or a pharmaceutically acceptable salt or prodrug thereof is parenterally administered.

[Item 2C]

The tandospirone or a pharmaceutically acceptable salt or prodrug thereof of any one of the preceding items, wherein the parenteral administration is selected from transdermal administration, intradermal administration, subcutaneous administration, intramuscular administration, and a combination thereof.

[Item 3C]

The tandospirone or a pharmaceutically acceptable salt or prodrug thereof of any one of the preceding items, wherein the parenteral administration has sustainability or is sustainably administered.

[Item 4C]

The tandospirone or a pharmaceutically acceptable salt or prodrug thereof of any one of the preceding items, wherein the parenteral administration comprises transdermal administration.

[Item 5C]

The tandospirone or a pharmaceutically acceptable salt or prodrug thereof of any one of the preceding items, wherein the motor complications comprise levodopa induced dyskinesia (PD-LID).

[Item 6C]

Tandospirone or a pharmaceutically acceptable salt or prodrug thereof for treating, improving, or preventing motor complications associated with levodopa therapy for Parkinson's disease, wherein levodopa induced dyskinesia (PD-LID) is improved without resulting in a rebound symptom, and wherein the tandospirone or a pharmaceutically acceptable salt or prodrug thereof is transdermally administered.

[Item 7C]

The tandospirone or a pharmaceutically acceptable salt or prodrug thereof of any one of the preceding items, wherein levodopa induced dyskinesia (PD-LID) comprises peak-dose dyskinesia, diphasic dyskinesia, and a combination thereof.

[Item 8C]

The tandospirone or a pharmaceutically acceptable salt or prodrug thereof of any one of the preceding items, wherein the treatment, improvement, delay of progression, or prevention of motor complications comprises improvement, delay of progression, or prevention of a levodopa induced dyskinesia (PD-LID) symptom, reduction of a period of levodopa induced dyskinesia (PD-LID) manifestation, or a combination thereof.

[Item 9C]

Tandospirone or a pharmaceutically acceptable salt or prodrug thereof for accomplishing the improvement, delay of progression, or prevention of a levodopa induced dyskinesia (PD-LID) symptom, reduction of a period of levodopa induced dyskinesia (PD-LID) manifestation, or a combination thereof, wherein the tandospirone or a pharmaceutically acceptable salt or prodrug thereof is parenterally administered.

[Item 10C]

The tandospirone or a pharmaceutically acceptable salt or prodrug thereof of any one of the preceding items, wherein the improvement of a levodopa induced dyskinesia (PD-LID) symptom is a clinically significant improvement or greater.

[Item 11C]

The tandospirone or a pharmaceutically acceptable salt or prodrug thereof of any one of the preceding items, wherein the improvement of a levodopa induced dyskinesia (PD-LID) symptom is to a sufficient level to attain a clinical effect.

[Item 12C]

The tandospirone or a pharmaceutically acceptable salt or prodrug thereof of any one of the preceding items, which is a transdermally administered formulation.

[Item 13C]

The tandospirone or a pharmaceutically acceptable salt or prodrug thereof of any one of the preceding items, which is an adhesive formulation.

[Item 14C]

The tandospirone or a pharmaceutically acceptable salt or prodrug thereof of any one of the preceding items, wherein the transdermally administered formulation is a tape/patch.

[Item 15C]

The tandospirone or a pharmaceutically acceptable salt or prodrug thereof of any one of the preceding items, wherein a drug dosage of the tandospirone or a pharmaceutically acceptable salt or prodrug thereof is 0.1 to 100 mg per day as a free form of tandospirone.

[Item 16C]

The tandospirone or a pharmaceutically acceptable salt or prodrug thereof of any one of the preceding items, wherein an amount of drug penetration for the tandospirone or a pharmaceutically acceptable salt or prodrug thereof is 0.1 to 20 mg per day as a free form of tandospirone.

[Item 17C]

The tandospirone or a pharmaceutically acceptable salt or prodrug thereof of any one of the preceding items, wherein the tandospirone or a pharmaceutically acceptable salt or prodrug thereof is a transdermally administered formulation, and a total applied area per dose is 1 to 100 cm$^2$.

[Item 18C]

The tandospirone or a pharmaceutically acceptable salt or prodrug thereof of any one of the preceding items, wherein the tandospirone or a pharmaceutically acceptable salt or prodrug thereof is administered so that a human blood (plasma) tandospirone concentration is 0.05 to 20 ng/mL for 12 hours or longer per day.

[Item 19C]

The tandospirone or a pharmaceutically acceptable salt or prodrug thereof of any one of the preceding items, wherein the tandospirone or a pharmaceutically acceptable salt or prodrug thereof is administered so that a human blood (plasma) tandospirone concentration is 0.05 to 20 ng/mL for 8 to 16 hours after administration of the tandospirone or a pharmaceutically acceptable salt or prodrug thereof.

[Item 20C]

The tandospirone or a pharmaceutically acceptable salt or prodrug thereof of any one of the preceding items, wherein the tandospirone or a pharmaceutically acceptable salt or prodrug thereof is an adjunct of levodopa.

[Item 21C]

The tandospirone or a pharmaceutically acceptable salt or prodrug thereof of any one of the preceding items, which is used with levodopa as the fixed-dose combination or concomitantly as separate formulations.

[Item 22C]

A combination of tandospirone or a pharmaceutically acceptable salt or prodrug thereof and (1) levodopa or (2) levodopa and a metabolizing enzyme inhibitor of levodopa for treating or preventing Parkinson's disease without accompanying or by minimizing PD-LID, wherein the tandospirone or a pharmaceutically acceptable salt or prodrug thereof is parenterally administered.

[Item 23C]

Tandospirone or a pharmaceutically acceptable salt or prodrug thereof for treating or preventing Parkinson's disease without accompanying or by minimizing PD-LID, wherein the tandospirone or a pharmaceutically acceptable salt or prodrug thereof is administered in combination with (1) levodopa or (2) levodopa and a metabolizing enzyme inhibitor of levodopa, wherein the tandospirone or a pharmaceutically acceptable salt or prodrug thereof is parenterally administered.

[Item 24C]

A combination of (1) levodopa or (2) levodopa and a metabolizing enzyme inhibitor of levodopa for treating or preventing Parkinson's disease without accompanying or by minimizing PD-LID, wherein the combination of (1) levodopa or (2) levodopa and a metabolizing enzyme inhibitor of levodopa is administered in combination with tandospirone or a pharmaceutically acceptable salt or prodrug thereof, and wherein the tandospirone or a pharmaceutically acceptable salt or prodrug thereof is parenterally administered.

[Item 25C]

Tandospirone or a pharmaceutically acceptable salt or prodrug thereof for improving the exacerbation in quality of response to levodopa therapy of a Parkinson's disease patient with dyskinesia, wherein the tandospirone or a pharmaceutically acceptable salt or prodrug thereof is parenterally administered.

[Item 26C]

The tandospirone or a pharmaceutically acceptable salt or prodrug thereof of any one of the preceding items, which is a free form.

[Item X1A]

A method for treating, improving, or preventing motor complications of Parkinson's disease in a subject, comprising parenterally administering an effective amount of tandospirone or a pharmaceutically acceptable salt thereof to a subject in need thereof.

[Item X1B]

A method for treating, improving, or preventing dyskinesia of Parkinson's disease in a subject, comprising parenterally administering an effective amount of tandospirone or a pharmaceutically acceptable salt thereof to a subject in need thereof.

[Item X1C]

A method for treating, improving, or preventing dyskinesia of Parkinson's disease in a subject undergoing drug therapy for Parkinson's disease, comprising parenterally administering an effective amount of tandospirone or a pharmaceutically acceptable salt thereof to the subject undergoing drug therapy for Parkinson's disease.

[Item X1D]

A method for treating, improving, or preventing dyskinesia of Parkinson's disease in a subject undergoing levodopa therapy for Parkinson's disease, comprising parenterally administering an effective amount of tandospirone or a pharmaceutically acceptable salt thereof to the subject undergoing levodopa therapy for Parkinson's disease.

[Item X1E]

A method for reducing OFF time in a subject who is a Parkinson's disease patient, comprising parenterally administering an effective amount of tandospirone or a pharmaceutically acceptable salt thereof to a subject undergoing drug therapy for Parkinson's disease.

[Item X1F]

A method for reducing OFF time and increasing ON time in a subject who is a Parkinson's disease patient, comprising parenterally administering an effective amount of tandospirone or a pharmaceutically acceptable salt thereof to a subject undergoing drug therapy for Parkinson's disease.

[Item 1G]

A method for reducing OFF time and increasing ON time without a troublesome dyskinesia in a subject who is a Parkinson's disease patient, comprising parenterally administering an effective amount of tandospirone or a pharmaceutically acceptable salt thereof to a subject undergoing drug therapy for Parkinson's disease.

[Item X1H]

A method for reducing OFF time and increasing ON time without a troublesome dyskinesia in a subject who is a Parkinson's disease patient, comprising parenterally administering an effective amount of tandospirone or a pharmaceutically acceptable salt thereof to a subject undergoing levodopa therapy for Parkinson's disease.

[Item X1I]

A method for treating, improving, or preventing motor complications of Parkinson's disease, comprising parenterally administering an effective amount of tandospirone or a pharmaceutically acceptable salt thereof to a subject in need thereof to sustainably maintain an amount of dopamine in a synaptic cleft of a striatum in the subject.

[Item X1I2]

The method of item X1I, wherein the amount of dopamine in a synaptic cleft of a striatum is XX pg/ml to XX pg/ml.

[Item 52]

The method of any one of the preceding items, wherein the tandospirone or a pharmaceutically acceptable salt thereof is administered so that an amount of change in striatal [$^{11}$C] raclopride receptor binding from before levodopa administration to 1 hour after administration (amount of change B/1 h) after administering the tandospirone or a pharmaceutically acceptable salt thereof is less than 10%.

[Item X1I3]

The method of items X1I or X1I2, wherein the tandospirone or a pharmaceutically acceptable salt thereof is administered so as not to induce a rebound symptom in the subject.

In a specific embodiment, the present invention is provided as an adhesive formulation (also referred to as a transdermal patch/tape agent). When the tape agent of the invention is applied, dyskinesia symptoms associated with levodopa therapy for Parkinson's disease can be more preferably prevented or improved. Therapy of Parkinson's disease wherein a single dose and/or a daily dose of levodopa is increased, relative to prior to therapy using the tape agent of the invention, without exacerbation of dyskinesia, can be administered in an actual clinical setting when the tape agent of the invention is applied to more preferably prevent or improve dyskinesia symptoms associated with levodopa therapy for Parkinson's disease.

Current therapy attempts to treat Parkinson's disease patients with small and frequent doses of levodopa to prevent the manifestation of dyskinesia (Pakinsonbyo Shinryo Gaidorain 2018 bajon [Parkinson's Disease Diagnosis and Treatment Guidelines 2018 version] (Third edition, Q&A for Parkinson's disease diagnosis, Chapter III, Therapy for motor symptoms)).

The manifestation of dyskinesia can be delayed and the levodopa containing formulation can be adjusted to an optimal dose by administering a parenterally administered formulation of tandospirone provided by the invention. In other words, a more preferred therapy of Parkinson's disease symptoms is enabled without exacerbating dyskinesia symptoms, even if a single dose of levodopa is increased to reduce the number of doses or the daily dosage of levodopa is increased for Parkinson's disease patients with or at a risk of manifestation of dyskinesia.

The tandospirone or a pharmaceutically accepted salt or prodrug thereof and therapeutic method of the invention enable therapy or prevention to reduce levodopa induced motor complications or levodopa induced dyskinesia involving the normal daily dosage for levodopa therapy specified in Pakinsonbyo Shinryo Gaidorain 2018 bajon [Parkinson's Disease Diagnosis and Treatment Guidelines 2018 version] published by the Japanese Society of Neurology or a corresponding guideline in the US or Europe.

Further, a more preferred effect of improving dyskinesia such as drug-induced dyskinesia including levodopa induced dyskinesia (PD-LID) or the like can be provided relative to oral administration by administering a parenterally administered formulation of tandospirone provided by the invention.

The inventors have found for the first time that oral administration of tandospirone with expectation of an effect of improving dyskinesia instead leads to temporary exacerbation of dyskinesia. In other words, the inventors have found that oral administration of tandospirone is not preferable as a therapeutic drug for the improvement of dyskinesia because the oral administration involves a "rebound symptom" of dyskinesia. As used herein, "rebound symptom" is the symptom described in [0037]. Since oral administration of tandospirone results in a "rebound symptom", it is not preferable to increase the dosage of a levodopa containing formulation.

The inventors have found that the tandospirone parenteral composition of the invention can improve dyskinesia without a "rebound symptom". A dyskinesia score can be measured as an "AIMs score" (AIMs is an abbreviation for "abnormal involuntary movements") by the method described in [0039].

Therefore, the present invention can be practiced as the following specific embodiments.

(1) A method of preventing or treating Parkinson's disease, a method of improving dyskinesia, or a method of preventing or treating Parkinson's disease with improved dyskinesia, comprising:
(A) parenterally administering tandospirone; and
(B) administering an increased dosage of levodopa compared to a conventional dosage.

(2) A method of preventing or treating Parkinson's disease, a method of improving dyskinesia, or a method of preventing or treating Parkinson's disease with improved dyskinesia, comprising:
(A) parenterally administering tandospirone; and
(B) increasing the dosage of levodopa to more than a conventional single dosage to adjust the number of daily dosages.

(3) A method of preventing or treating Parkinson's disease, a method of improving dyskinesia, or a method of preventing or treating Parkinson's disease with improved dyskinesia in a patient with or at a risk of manifestation of dyskinesia, comprising:
(A) parenterally administering tandospirone; and
(B) administering levodopa with a maintained or increased dosage.

(4) A method of preventing or treating Parkinson's disease, a method of improving dyskinesia, or a method of preventing or treating Parkinson's disease with improved dyskinesia in a patient with or at a risk of manifestation of dyskinesia, comprising:

(A) adding parenteral administration of tandospirone to conventional levodopa therapy; and (B) increasing a levodopa dosage to the extent that dyskinesia is not exacerbated and concomitantly using parenteral administration of tandospirone.

(5) A method of preventing or treating Parkinson's disease, a method of improving dyskinesia, or a method of preventing or treating Parkinson's disease with improved dyskinesia comprising:

(A) maintaining a plasma concentration of tandospirone to 0.05 to 20 ng/mL; and (B) administering levodopa.

(6) A method of preventing or treating Parkinson's disease, a method of improving dyskinesia, or a method of preventing or treating Parkinson's disease with improved dyskinesia in a patient with or at a risk of manifestation of dyskinesia, comprising:

(A) maintaining a plasma concentration of tandospirone to 0.05 to 20 ng/mL; and (B) administering levodopa.

The basis of the invention is the following.

*Since levodopa has a short half-life and the effect is not sustained, levodopa is generally administered multiple times per day. Meanwhile, the blood concentration of tandospirone is maintained for 24 hours when the tandospirone of the invention is administered as a tape agent, i.e., applied one sheet per day. For this reason, for transdermally administered formulations, levodopa is administered while being exposed to tandospirone no matter at what time levodopa is administered. On the other hand, if a Sediel tablet and levodopa are administered (orally administered) at the same timing three times a day, levodopa would be administered while the blood concentration of tandospirone is reduced. In other words, the feature is in being different from an oral agent. Further, it is preferable that the blood concentration of tandospirone is maintained upon administration of levodopa.

In a specific embodiment, the present invention can be used in various applications (indications). For example, indications such as improvement of dyskinesia (anti-dyskinesia drug) <PD-LID improving drug>, treating dyskinesia (involuntary movements) in Parkinson's disease patients treated with levodopa therapy, with or without other medicines that increase the effects of dopamine in the brain, a caution for use or a label (package insert) can be appended.

The present invention is intended so that one or more of the aforementioned features can be provided not only as the explicitly disclosed combinations, but also as other combinations. Additional embodiments and advantages of the present invention are recognized by those skilled in the art by reading and understanding the following detailed description, as needed.

As used herein, motor complications and dyskinesia refer to symptoms associated with levodopa therapy for Parkinson's disease, and exclude symptoms originating from other diseases and symptoms associated with therapy using a compound other than levodopa, unless specifically noted otherwise.

As used herein, motor complications such as motor fluctuations and dyskinesia (including, for example, Movement disorders) refer to symptoms associated with drug therapy such as levodopa therapy for Parkinson's disease or a circumstance equivalent thereto (e.g., Drug-induced dyskinesia), unless specifically noted otherwise. Such motor complications exclude symptoms that originate from other diseases and are associated with therapy other than drug therapy for Parkinson's disease with levodopa or the like or a circumstance equivalent thereto. In this regard, "symptoms that originate from other diseases and are associated with therapy other than drug therapy for Parkinson's disease with levodopa or the like or a circumstance equivalent thereto" refers to symptoms originating from only a factor other than Parkinson's disease. Thus, it is understood that motor complications such as motor fluctuations and dyskinesia including symptoms originating from Parkinson's disease (coexistence) are within the scope of the present disclosure. It is also understood that the cause and effect relationship of motor complications such as motor fluctuations and dyskinesia with respect to an agent such as levodopa does not need to be proven, and such motor complications are within the scope of the present disclosure as long as they are manifested upon administration of an agent such as levodopa or during a period where the effect thereof is understood to remain (e.g., a method of treating dyskinesia in a patient undergoing levodopa therapy is encompassed). Motor complications associated with a neurodegenerative disease similar to Parkinson's disease from dopamine deficiency in the striatum and the like are also encompassed. Examples thereof include multiple system atrophy, progressive supranuclear palsy, corticobasal degeneration, Lewy body dementia, and the like.

Advantageous Effects of Invention

The pharmaceutical composition of the invention has expectation as a therapeutic drug, improving drug, progression delaying drug, or prophylactic drug for levodopa induced motor complications in Parkinson's disease (e.g., levodopa induced dyskinesia (PD-LID), or the like). Specifically, the pharmaceutical composition of the invention has expectation as a therapeutic drug, improving drug, progression delaying drug, or prophylactic drug for PD-LID without a rebound symptom.

BRIEF DESCRIPTION OF DRAWINGS

FIGS. 8A-8C show results of evaluating dyskinesia-like symptoms when tandospirone citrate was orally administered to a PD-LID rat model. Specifically, tandospirone citrate (30 mg/kg, 100 mg/kg as citrate concentration) was orally administered to a PD-LID rat model, and levodopa was administered 5 minutes later to evaluate dyskinesia-like symptoms. The results are indicated in terms of mean value±standard error. FIG. 8A shows changes in AIMs score over time after levodopa administration. FIG. 8B shows the total AIMs score in 180 minutes. FIG. 8C shows the total AIMs score in 100 to 180 minutes.

DESCRIPTION OF EMBODIMENTS

Figure 1:
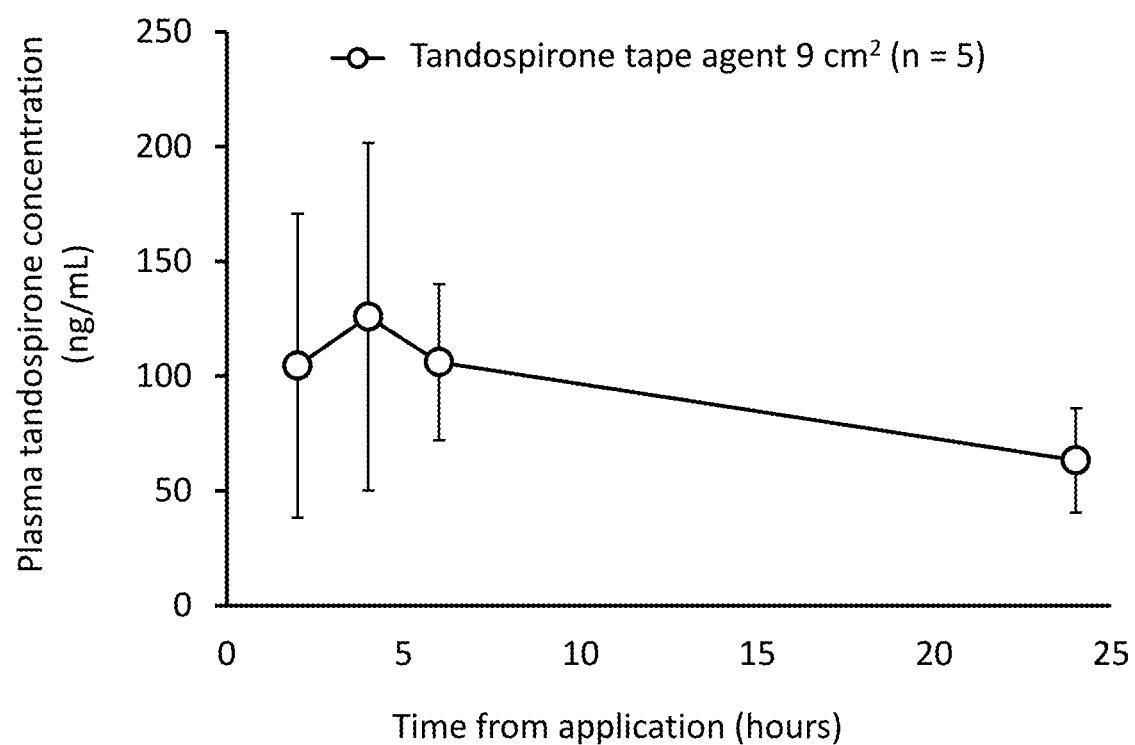
FIG. 1 is a diagram showing changes in plasma concentration when a tandospirone tape agent was applied to a normal rat. Specifically, changes in plasma tandospirone concentrations obtained by applying a tandospirone tape agent to a normal rat (9 cm$^2$: 31±2 cm$^2$/kg) are shown in terms of mean value±standard deviation. The x axis indicates the time from application, and the y axis indicates the plasma tandospirone concentration.

The present invention is explained hereinafter while showing the best modes thereof. Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. Further, the terms used herein should be understood as being used in the meaning that is commonly used in the art, unless specifically noted otherwise. Therefore, unless defined otherwise, all terminologies and scientific technical terms that are used herein have the same meaning as the general understanding of those skilled in the art to which the present invention pertains. In case of a contradiction, the present specification (including the definitions) takes precedence. (Definitions, Etc.)

The definitions and/or the basic technology of the terms that are especially used herein are described hereinafter as appropriate.

As used herein, "tandospirone" [Chemical name: (1R,2S, 3R,4S)—N-[4-{4-(pyrimidine-2-yl)piperadine-1-yl}butyl]-2,3-bicyclo[2.2.1]heptanedicarboximide] has the following structure.

[Chemical Formula 1]

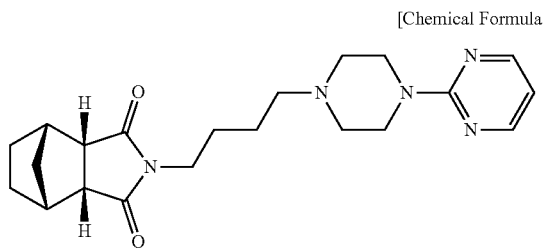

A Sediel tablet comprising a citric acid salt of tandospirone as an active ingredient is used for therapy as a serotonergic anxiolytic drug (e.g., Sediel package insert or label, revised in April 2016, 14th edition, Sumitomo Dainippon Pharma Co., Ltd.; see Japanese Laid-Open Publication No. 58-126865). Tandospirone has a beneficial effect on memory in chronic schizophrenia. In particular, it is known that cognitive dysfunction can be improved by administering tandospirone or a pharmaceutically acceptable salt thereof while continuing maintenance therapy using a typical antipsychotic such as haloperidol (see Japanese Laid-Open Publication No. 2002-20291).

As an active ingredient used in the pharmaceutical composition of the invention, tandospirone (free form) is preferred, but a pharmaceutically acceptable salt of tandospirone or a prodrug of tandospirone can also be used in the same manner. Pharmaceutically acceptable salts and prodrugs of tandospirone include salts of inorganic acid such as hydrochloride, hydrobromide, sulfate, and phosphate and salts of organic acid such as acetate, butyrate, tartrate, citrate, maleate, and fumarate.

Prodrugs of tandospirone refer to any component, which has a different structure from tandospirone, but can be converted into tandospirone or an active ingredient based thereon by metabolism after administration to exert efficacy.

Prodrugs of tandospirone refer to compounds that are converted to tandospirone due to a reaction with an enzyme, or the like under physiological conditions in the body, i.e., compounds that are changed into tandospirone as a result of enzymatic oxidation, reduction, hydrolysis, or the like. Prodrugs of tandospirone may also be compounds that are changed into tandospirone under physiological conditions such as those described in "Iyakuhin no Kaihatsu" [Drug Development], Hirokawa-Shoten Ltd., 1990, Vol. 7, Molecular Design, pp. 163 to 198.

The tandospirone of the invention or a salt or prodrug thereof (hereinafter, also referred to as tandospirones) has excellent serotonin 5-HT1A receptor activation action.

The tandospirone of the invention has low toxicity and is safe.

A drug with an active ingredient of "tandospirone citrate" is clinically applied as an oral agent as a therapeutic agent for (1) depression or panic in neurosis and (2) physical symptoms, and depression, anxiety, restlessness, or sleep disorder in a psychosomatic disease. Tandospirone is highly selective to serotonin 1A receptors (hereinafter, also referred to as "5-HT1A receptor"), but has low affinity to dopamine 2 receptors (also referred to as "D2 receptor") in in vitro receptor binding evaluation for various neurotransmitter receptors. For this reason, tandospirone is understood as activating a 5-HT1A receptor and selectively acting on serotonin nerves to exert an effect on neurosis or the like.

As used herein, "drug therapy for Parkinson's disease" refers to therapy using a therapeutic drug for Parkinson's disease.

Examples of drug therapy for Parkinson's disease include dopamine replacement therapy (levodopa therapy, drug therapy for Parkinson's disease using a levodopa metabolite inhibitor or dopamine receptor agonist, or the like), adjunct agent for Parkinson's disease, and the like. Representative examples of dopamine replacement therapy include levodopa therapy, narrowly defined levodopa therapy, drug therapy using a levodopa metabolite inhibitor, and the like.

The pharmaceutical composition of the present disclosure has expectation as a drug for treating, improving, or preventing motor complications of a patient undergoing such drug therapy for Parkinson's disease. In particular, it is known that motor complications tend to manifest in patients undergoing levodopa therapy, so that the pharmaceutical composition of the present disclosure is useful for such patients.

As used herein, "levodopa" (as broadly defined) includes the narrowly defined levodopa (L-3,4-dihydroxyphenylalanine (IUPAC nomenclature is (S)-2-amino-3-(3,4-dihydroxyphenyl)propanoic acid); also called levodopa) as well as any other drugs attaining the same efficacy as L-3,4-dihydroxyphenylalanine. Examples of such other drugs include, but are not limited to, esters of L-3,4-dihydroxyphenylalanine and salts thereof. Examples of esters of L-3,4-dihydroxyphenylalanine include levodopa ethyl ester (LDEE; ethyl(2S)-2-amino-3-(3,4-dihydroxyphenyl) propanoate), levodopa propyl ester; levodopa propyl ester (propyl(2S)-2-amino-3-(3,4-dihydroxyphenyl) propanoate), levodopa methyl ester (methyl(2S)-2-amino-3-(3,4-dihydroxyphenyl)propanoate), and the like. An ester of L-3,4-dihydroxyphenylalanine can be, for example, a salt including hydrated salt. A salt of levodopa ester can include, but is not limited to, one of octanoate, myristate, succinate, succinate dihydrate, fumarate, fumarate dihydrate, mesylate, tartrate, and hydrochloride. Examples of succinate dehydrate or succinate of ester of L-3,4-dihydroxyphenylalanine include levodopa ethyl ester succinate (LDEE-S) and levodopa ethyl ester succinate dehydrate (LDEE-S-dihydrate or LDEE-S(d))>

As used herein, "metabolizing enzyme inhibitor of levodopa" refers to any drug having action to inhibit the metabolism of broadly defined levodopa to enhance the action thereof. Examples thereof include dopa decarboxylase inhibitors (DCI) that prevent levodopa from changing into dopamine in the intestine, liver, or blood vessel (examples thereof include carbidopa, α-methyldopa, benserazide (Ro4-4602), α-difluoromethyl-DOPA (DPMD), salts thereof, and the like), catechol-O-methyl transferase inhibitors (COMT-I) that similarly prevent the decomposition of levodopa before entering the brain (examples thereof include entacapone), monoamine oxidase inhibitors (MAO-I) that prevent the decomposition of dopamine in the brain (examples thereof include selegiline), and the like.

(Disease/Disorder)

As used herein, "motor complications" refer to any motor symptom that is a problem to be treated found in patients with advanced Parkinson's disease. Examples thereof include dyskinesia (e.g. levodopa induced dyskinesia (PD-LID)), which is an involuntary movement associated with levodopa therapy, and the like. Motor complications are understood to be based on excessive action of levodopa, but the mechanism thereof is not necessarily elucidated.

"Dyskinesia <involuntary movement>" is a type of motor complication manifested in a patient of Parkinson's disease or the like, referring to movement of hands, legs, or body undulating involuntarily. This includes dyskinesia of patients with a neurodegenerative disease accompanied with dopamine deficiency in the striatum just like Parkinson's disease. It is understood that dyskinesia is caused by various factors. Examples thereof include dyskinesia induced by various agents (e.g., levodopa), dyskinesia manifested upon drug dosing, and the like.

As used herein, "levodopa induced dyskinesia <involuntary movement> (PD-LID)" refers to involuntary movement of the hand, leg, or body unintentionally weaving, which is occurred during levodopa treatment. It is known that dyskinesia is readily manifested if a large amount of levodopa is continuously dosed more than necessary from the initial phase of the disease, and it is very difficult to control once it is manifested, even if the dosage of levodopa is subsequently increased or decreased to various levels. Peak-dose dyskinesia is known as an exemplary symptom of PD-LID. The symptom is manifested on the face, tongue, neck, limbs, body trunk, or the like when the blood levodopa concentration is high.

Involuntary movement (dyskinesia) refers to a portion of the body moving involuntarily or not stopping, biting of the lips, difficulty in speech, inability to stay still, or difficulty in moving the hand or leg as intended, and is a motor disorder in which involuntary movement is observed in the limbs and/or mouth or face, and/or body axis. Dyskinesia observed in PD patients undergoing therapy with levodopa is known as levodopa induced dyskinesia (LID), which occurs in more than half of PD patients who have had therapy with levodopa for the past 5 to 10 years. The percentage (%) of patients suffering from LID increases with passage of time (for an overview, see, for example, Encarnacion and Hauser, (2008), "Levodopa-induced dyskinesias in Parkinson's disease: etiology, impact on quality of life, and treatments.", Eur Neurol, 60(2), pages 57 to 66).

Peak-dose dyskinesia is involuntary movement resulting from excessive antiparkinsonian drug. Diphasic dyskinesia is dyskinesia manifested in two phases, i.e., at the start and near the end of the effect of an antiparkinsonian drug.

As used herein, "pharmaceutically acceptable salt" includes acid and/or base salts formed with inorganic and/or organic acid and base. Examples thereof include acid addition salts and base addition salts. Examples of acid addition salts include inorganic acid salts such as hydrochloride, hydrobromide, sulfate, hydroiodide, nitrate, and phosphate, and organic acid salts such as citrate, oxalate, phthalate, fumarate, maleate, succinate, malate, acetate, formate, propionate, benzoate, trifluoroacetate, methanesulfonate, benzenesulfonate, p-toluenesulfonate, and camphorsulfonate. Examples of base addition salts include inorganic base salts such as sodium salt, potassium salt, calcium salt, magnesium salt, barium salt, and aluminum salt, and organic base salts such as trimethylamine, triethylamine, pyridine, picoline, 2,6-lutidine, ethanolamine, diethanolamine, triethanolamine, trometamine [tris(hydroxymethyl)methylamine], tert-butylamine, cyclohexylamine, dicyclohexylamine, and N—N-dibenzylethylamine. Furthermore, examples of "pharmaceutically acceptable salt" include amino acid salts of a basic or acidic amino acid such as arginine, lysine, ornithine, aspartic acid, and glutamic acid. Pharmaceutically acceptable salts are well known in the art. For example, Berge et al. describes pharmaceutically acceptable salts in detail in J. Pharmaceutical Sciences (1977) 66: 1-19.

The tandospirone or a pharmaceutically acceptable salt or prodrug thereof or medicament of the invention can comprise a carrier as needed. As used herein, the term "carrier" refers to a pharmaceutically acceptable substance, composition, or excipient such as a liquid or solid bulking agent, diluent, additive, solvent, base agent, or skin permeation promoting agent, which is associated with or enables the transport or carriage of a target pharmaceutical compound from an organ/tissue of the body or a part thereof to another organ/tissue of the body or a part thereof. "Pharmaceutically acceptable" refers to being compatible with other raw materials in the formulation and being harmless to the subject.

Diseases that are treatable in the present invention include any motor complications such as drug motor complications (e.g. levodopa induced motor complication) in Parkinson's disease.

In a specific embodiment, a patient who is treatable in the present invention includes Parkinson's disease patients who have or have the potential of manifesting motor complications such as drug induced motor complications (e.g. levodopa induced motor complications). Motor complications such as drug induced motor complications (e.g. Levodopa induced motor complications) include dyskinesia such as drug induced dyskinesia (e.g. levodopa induced dyskinesia).

The effect of improvement on dyskinesia such as drug induced dyskinesia (e.g. levodopa induced dyskinesia) in Parkinson's disease in the present invention can be clinically confirmed using a patient diary or a clinical evaluation scale such as Unified Dyskinesia Rating Scale (UDysRS), Clinical Dyskinesia Rating Scale (CDRS), or Abnormal Involuntary Movement Scale (AIMS). The effect of improving dyskinesia can also be confirmed by dyskinesia-like abnormal involuntary movement behavior evaluation in a non-clinical model PD-LID rat model. The improvement, delay of progression, or prevention of dyskinesia such as drug induced dyskinesia (e.g. levodopa induced dyskinesia (PD-LID)) symptoms, as well as reduction in the period of dyskinesia such as drug induced dyskinesia (e.g. levodopa induced dyskinesia (PD-LID)) manifestation can be measured by using this approach.

The present invention can confirm whether a PD-LID symptom is exacerbated by whether a clinical evaluation scale of dyskinesia such as UDysRS, CDRS, or AIMS has significantly deteriorated relative to before therapy with tandospirone. This can also be confirmed by whether clear exacerbation in a dyskinesia associated symptom is observed from a patient diary. Whether a dyskinesia such as drug induced dyskinesia (e.g. levodopa induced dyskinesia) symptom is accompanied with pain can be confirmed herein with clinical records such as a patient diary.

In the present invention, "rebound symptom" of dyskinesia such as drug induced dyskinesia (e.g. levodopa induced dyskinesia (PD-LID)) refers to a phenomenon in which the dyskinesia score is rather exacerbated temporarily by a therapeutic drug for improving dyskinesia. A "rebound symptom" is a phenomenon with more exacerbation in dyskinesia than a case without therapy using a dyskinesia improving drug after the peak period (e.g., 1 hour) of antiparkinsonian action of levodopa during therapy using the dyskinesia improving drug. The symptom is anticipated to manifest in 1 to 6 hours after administration of levodopa.

In the present invention, improvement in dyskinesia such as drug induced dyskinesia (e.g. levodopa induced dyskinesia (PD-LID)) without a rebound symptom means that the total score for dyskinesia is improved without exacerbation of dyskinesia, not even temporarily, compared to a case without therapy using a dyskinesia improving drug after levodopa administration. "Without exacerbation of dyskinesia" refers to a condition with dyskinesia (AIMs score of 2 or greater in an AIMs evaluation system of non-clinical PD-LID rat model) and without significant deterioration in the dyskinesia score compared to a case without therapy using a dyskinesia improving drug.

A rebound symptom of dyskinesia such as drug induced dyskinesia (e.g. levodopa induced dyskinesia (PD-LID)) can be evaluated with clear dyskinesia-like symptoms (AIMs score of 2 or greater) observed at 120 to 140 minutes after levodopa administration, total AIMs score in 100 to 180 minutes, or the like as an indicator in an AIMs evaluation system of non-clinical PD-LID rat model. Improvement of dyskinesia can be evaluated by a total AIMs score in 180 minutes after levodopa administration. In this AIMs evaluation system of a PD-LID rat model, an AIMs score of 2 or greater is diagnosed as dyskinesia, and a greater number means more severe dyskinesia. An AIMs score of less than 2 is diagnosed as no dyskinesia.

The inventors have found that oral administration of tandospirone results in a rebound symptom, so that it is unsuitable for therapy of PD-LID. Meanwhile, the inventors have found that parenteral administration of tandospirone as in the present invention improves dyskinesia such as drug (e.g. levodopa) induced dyskinesia (PD-LID) without a rebound symptom. The therapeutic mode is preferably sustained parenteral administration of tandospirone or parenteral administration of a sustained release formulation, and more preferably transdermal administration of tandospirone.

As used herein, "adjunct" refers to a drug other than the drug with the primary action. If levodopa is the primary agent, tandospirone and the like is an adjunct in the present invention.

The daily dosage of the primary agent levodopa herein is the normal dose for levodopa therapy specified in Pakinsonbyo Shinryo Gaidorain 2018 bajon [Parkinson's Disease Diagnosis and Treatment Guidelines 2018 version] or a corresponding guideline in the US or Europe. In general, the normal daily dose of levodopa is 50 to 1200 mg/day and preferably 100 mg to 600 mg/day in concomitant use or as a combined agent with a peripheral dopa decarboxylase inhibitor (DCI). For example, SINEMET® (Carbidopa-Levodopa combination tablet) (New Drug Application (NDA) #017555) approved by the FDA is provided as a 1:4 ratio combination tablet (25 mg Carbidopa-100 mg Levodopa) and 1:10 ratio combination tablet (10 mg Carbidopa-100 mg Levodopa or 25 mg Carbidopa-250 mg Levodopa). The daily maintenance dose of SINEMET® is administered so that Carbidopa would be 70 mg to 100 mg. SINEMET® is administered at the maximum daily dose of up to 200 mg as Carbidopa.

The tandospirone or a pharmaceutically acceptable salt or prodrug thereof or therapeutic method herein can enable therapy to reduce motor complications associated with administration of a normal dose in levodopa therapy or prevention of motor complications.

The levodopa dosage can be appropriately adjusted by administering the tandospirone or a pharmaceutically acceptable salt or prodrug thereof of the invention. The dosage can be increased within the range of the single dosage and daily dosage specified in, for example, Pakinsonbyo Shinryo Gaidorain 2018 bajon [Parkinson's Disease Diagnosis and Treatment Guidelines 2018 version] published by the Japanese Society of Neurology or a corresponding guideline in the US or Europe.

As used herein, "has sustainability" can be determined by those skilled in the art by utilizing known findings in the art while considering the descriptions herein. Specifically, having sustainability can be defined as maintaining a blood drug concentration for an extended period of time and exhibiting an effect of prolonged biological half-life. Examples of compositions having sustainability include various transdermally administered formulations described in [0052], various sustained release injection agents described in [0090], various implanted agents described in [0091], and the like. As used herein, "sustainably administered" refers to sustained administration of an active ingredient in the present invention from outside to inside the body, which can be achieved through transdermal absorption, injection, infusion, or the like while selecting a parenteral route of administration described in [0049].

As used herein, "clinically significant period" can be determined by those skilled in the art by utilizing known findings in the art while considering the descriptions herein. Specifically, if a significant effect such as prevention, treatment, or alleviation of motor complications targeted by the present invention is exhibited, the period of time can be defined as a clinically significant period. For "clinically significant improvement" as used herein, if a significant effect such as prevention, treatment, or alleviation of motor complications targeted by the present invention is exhibited, the state can be similarly defined as a clinically significant improvement. The approach to measure such a period or improvement can be appropriately selected by those skilled in the art. For example, any method described herein can be considered. However, the method is not limited thereto. For example, Pakinsonbyo Shinryo Gaidorain 2018 bajon [Parkinson's Disease Diagnosis and Treatment Guidelines 2018 version] published by the Japanese Society of Neurology can also be used. Alternatively, it is reported that the dyskinesia clinical evaluation index (MDS UDysRS Part III) is 2.32 points (Parkinsonism Relat Disord 21: 1349, 2015)). The method can be appropriately determined by considering (1) comparison with a placebo, (2) before and after therapy for each patient, or the like.

As used herein, "sustainably maintain a dopamine level in a striatum synaptic cleft" means that the dopamine level in the striatum synaptic cleft is maintained at a certain concentration or higher. This can be confirmed herein by, for example, a PET test under the conditions described in the aforementioned reference document or the like. The effect of a pharmaceutical composition can be confirmed herein from the amount of change 1 h/4 h in the amount of striatal $[^{11}C]$ raclopride receptor binding of less than 5% and/or the ratio of change 1 h/4 h in the amount of striatal $[^{11}C]$ raclopride receptor binding of 90% or less, preferably 80% or less, and more preferably 70% or less, or the like. As used herein, the amount of change in striatal $[^{11}C]$ raclopride receptor binding from before levodopa administration to 1 hour after administration is referred to as the amount of change B/1 h.

As used herein, "suppress a rapid change in a dopamine level in a striatum synaptic cleft" means that the dopamine level in the striatum synaptic cleft does not change significantly in a short period of time. This can be confirmed by, for example, a PET test under the conditions described in the aforementioned reference document or the like. The effect of the pharmaceutical composition of the invention can be confirmed from the amount of change B/1 h in the amount of striatal [$^{11}$C] raclopride receptor binding of less than 10% and/or the ratio of change B/1 h of 90% or less, preferably 80% or less, and more preferably 70% or less, or the like.

As used herein, "suppress intermittent domain receptor stimulation" means to suppress an increase/decrease of the dopamine level in the striatum synaptic cleft over time. This can be confirmed by, for example, a PET test under the conditions described in the aforementioned reference document or the like. The effect of the pharmaceutical composition of the invention can be confirmed from whether the difference between the amount of change B/1 h and the amount of change B/4 h in striatal [$^{11}$C] raclopride receptor binding is reduced or the like.

As used herein, "sufficient period to attain a clinical effect" and "sufficient level to attain a clinical effect" can also be determined by those skilled in the art by utilizing known findings in the art while considering the descriptions herein. Specifically, if the period or level that can attain a clinical effect such as prevention, therapy, or alleviation of motor complications targeted by the present invention can be measured, the period or level can be evaluated as a sufficient period to attain a clinical effect. An approach of measuring such a period or level can be appropriately selected by those skilled in the art. For example, any method described herein can be considered. However, the method is not limited thereto. For example, Pakinsonbyo Shinryo Gaidorain 2018 bajon [Parkinson's Disease Diagnosis and Treatment Guidelines 2018 version] published by the Japanese Society of Neurology or a corresponding guideline in the US or Europe can also be used.

As used herein, "no" "exacerbation of a levodopa induced dyskinesia (PD-LID) symptom in a Parkinson's disease patient" means that an already developed dyskinesia symptom is not exacerbated to a clinically significant degree or is not significantly exacerbated, dyskinesia manifestation period is not prolonged, a symptom is not significantly exacerbated, not even temporarily, as in a rebound symptom of dyskinesia, or a dyskinesia is not newly developed. A dyskinesia symptom can be confirmed, for example, by measurement using UPDRS, UDysRS, CDRS, AIMS, or the like, or a clinical record such as a patient diary.

As used herein, "exacerbation in quality of response to levodopa therapy of a Parkinson's disease patient" refers to any decrease in responsiveness of a patient to levodopa therapy. Such an exacerbation in the quality of response can be measured from a dyskinesia symptom or the like. "Improvement" of "exacerbation in quality of response to levodopa therapy of a Parkinson's disease patient" refers to improvement in the degree of dyskinesia symptom in levodopa therapy of each patient. The improvement can be confirmed by measurement using UPDRS, UDysRS, CDRS, AIMS, or the like, or a clinical record such as a patient diary.

As used herein, "parenteral administration" refers to a dosage form for any route that is not oral administration. Preferably, any mode for administering tandospirone in a mode and level that are effective for motor complications such as drug (e.g. levodopa) induced motor complications in Parkinson's disease is employed. Examples of means of parenteral administration include administration through transdermal absorption or transmucosal absorption, as well as injection, infusion, and combinations thereof. For example, administration through transdermal absorption or transmucosal absorption exerts an effect by contacting a transdermally administered formulation such as a paste agent, adhesive formulation, or spray to the skin or mucous membrane so that a drug in the formulation migrates into the body through the skin or mucous membrane. Examples of administration via injection or infusion include intravenous, intradermal, subcutaneous, intramuscular, and enteral administration (intestinal infusion), which can also be administered as a bolus and/or sustained infusion. Injection or infusion can use a suspension, liquid agent, emulsion, or implanted agent in an oily or aqueous medium, comprising another formulation substance such as a suspending agent, stabilizer, and/or a dispersant. Enteral administration (intestinal infusion) can provide sustained drug delivery to the proximal small intestine by using a tube or portable infusion pump by percutaneous endoscopic gastrostomy. In a preferred embodiment, parenteral administration can be performed in a form of a sustained administration. Such sustained administration can be accomplished with transdermal patch/tape or the like, injection, infusion, or the like.

In the present invention, tandospirone or a pharmaceutically acceptable salt or prodrug thereof is preferably administered by a method that can maintain blood drug concentration for a long period of time, and is more preferably administered by a method that can suppress the generation of metabolites. Examples of administration methods include transdermal administration and injection such as subcutaneous, intradermal, and intramuscular administrations. Injection such as subcutaneous, intradermal, and intramuscular administrations is preferably a method of administration that sustains the blood concentration. In particular, transdermal administration is the most preferred because it is an administration method that has a low degree of invasiveness and requires no hospital visits.

In the present invention, treatment, improvement, delay of progression, or prevention of motor complications associated with levodopa therapy for Parkinson's disease by parenteral administration including tandospirone or a pharmaceutically acceptable salt or prodrug thereof is preferred compared to therapy using an active ingredient other than the inventions herein or therapeutic methods and compositions other than the inventions herein from the viewpoint of having no adverse effect on levodopa action time (ON-time), having no adverse effect on parkinsonian symptoms (can be evaluated by UPDRS or the like), having no attenuation in the effect of the invention in repeated administration, capability to reduce the number of doses of levodopa formulations per day by increasing a levodopa formulation to the optimal dose without exacerbating motor complications, and the like.

"Transdermally administered formulation" refers to a paste agent, adhesive formulation, or spray (aerosol). Specific examples of adhesive formulations include tape agents (transdermal patch), poultice, plaster, and the like, and examples of paste agents include ointment, cream, lotion, liniment, liquid agent, gel, and the like. A transdermally administered formulation is preferably an adhesive formulation and more preferably a tape agent (transdermal patch). Since a "tape agent" is synonymous with a "patch" in the present invention, they are also denoted as "tape/patch" herein.

A transdermally administered formulation is manufactured by a known method using a pharmaceutically acceptable additive. In one embodiment, a transdermally administered formulation used in the present invention has an adhesive layer provided on a support, and the adhesive layer can be manufactured by including a thermoplastic elastomer or the like. A "thermoplastic elastomer" is an elastomer that softens and exhibits fluidity when heated, and exhibits thermoplasticity of returning to a rubber-like elastic when cooled. Examples thereof include various thermoplastic elastomers such as urethane, acrylic, styrene, and olefin based elastomers.

For the transdermally administered formulation of the invention, an adhesive layer can comprise nonvolatile hydrocarbon oil. As nonvolatile hydrocarbon oil, a chained saturated hydrocarbon with about 20 to 40 carbons or chained unsaturated hydrocarbon with about 20 to 40 carbons is preferable. Examples thereof include liquid paraffin, squalene, squalane, pristane, and the like. In particular, liquid paraffin is more preferable from the viewpoint of availability. Liquid paraffin is a mixture of colorless, odorless liquid alkanes with 20 or more carbons. In the present invention, liquid paraffin that is in compliance with the specification specified in the Japanese Pharmacopoeia, US Pharmacopoeia, or the like can be preferably used. Nonvolatile hydrocarbon oil with high viscosity is preferred. Use of liquid paraffin with high viscosity is especially preferable from the viewpoint of adhesiveness.

An adhesive layer can also comprise a tackifier as needed. A tackifier is generally a resin that is commonly used for imparting skin adhesiveness in the art of adhesive formulations. Examples thereof include rosin based resin, polyterpene resin, coumarone-indene resin, petroleum-based resin, terpene-phenol resin, alicyclic saturated hydrocarbon resin, and the like. One or more thereof can be selected therefrom and used.

If transdermal administration is envisioned, this can also be materialized by applying an ointment to the skin.

A dosage form for parenteral administration (e.g., transdermal administration) of the tandospirone or a pharmaceutically acceptable salt or prodrug thereof disclosed herein, other than a tape/patch, can include powder, spray, ointment, paste, cream, lotion, gel, and liquid solution.

Ointment, paste, cream, and gel can comprise, in addition to the tandospirone or a pharmaceutically acceptable salt or prodrug thereof disclosed herein, an additive such as animal and plant fat, oil, wax, paraffin, starch, tragacanth, cellulose derivative, polyethylene glycol, silicone, bentonite, silicic acid, talc, or zinc oxide, or a mixture thereof.

Powder and spray can comprise, in addition to the pharmaceutical composition disclosed herein, an additive such as lactose, talc, silicic acid, aluminum hydroxide, calcium silicate, or polyamide powder or a mixture thereof. A spray can further comprise a common high pressure gas such as chlorofluorohydrocarbon or volatile unsubstituted hydrocarbon such as butane or propane.

In addition to ointment, powder, solution, and the like are also understood to be within the scope of the disclosure herein, as long as it is suitable for parenteral administration.

A composition suitable for parenteral administration can comprise at least one type of pharmaceutically acceptable aseptic isotonic aqueous or non-aqueous solution, dispersion, suspension, emulsion, implanted agent, or aseptic powder that can be reconstituted into an aseptic injection solution or dispersion immediately before use.

The composition disclosed herein can be prepared as a suppository for rectal or vaginal administration. The composition can be prepared by mixing one or more compounds according to the disclosure herein with one or more suitable non-stimulatory additives or carriers including cocoa butter, polyethylene glycol, suppository wax, salicylate, or the like. The composition is a solid at room temperature, but is a liquid at body temperature. Thus, the composition melts in the rectum or the vaginal cavity to release the compound in the disclosure herein. A pharmaceutical composition suitable for vaginal administration can include a pessary, tampon, cream, gel, paste, foam, or spray formulation comprising a carrier known to be suitable in prior art.

As used herein, "drug dosage" is the amount of drug contained in a composition. As used herein, "amount of drug penetration" is the amount of drug intake into the body. If a composition is a transdermally administered formulation, "amount of drug penetration" is the amount of drug that has absorbed into the skin from the transdermally administered formulation, and is a value calculated by the following equation. "Amount of residual drug" is the amount of drug remaining in the transdermally administered formulation that has been peeled off after application. This amount can be quantified by the method described in the Examples (Reference Manufacturing Example) ([0099~0102] or the like. Amount of drug penetration (mg/day)=drug dosage (mg/day)−amount of residual drug (mg/day)

In the present invention, the drug dosage, amount of drug penetration, amount of residual drug, and blood (plasma) tandospirone concentration are amounts converted in terms of tandospirone free form, unless specifically noted otherwise.

In the present invention, the dosage or amount of penetration of tandospirone or a salt thereof can be appropriately adjusted depending on the type of compound, symptom/age/body weight/kidney or liver function of the patient, or the like. For example, the daily drug dosage is 0.1 to 500 mg, 0.1 to 400 mg, 0.1 to 250 mg, 0.1 to 220 mg, 0.1 to 180 mg, 0.1 to 100 mg, and preferably 0.2 to 50 mg, 1 to 250 mg, 3 to 250 mg or the like. Examples of the upper limit thereof include 1000 mg, 800 mg, 500 mg, 400 mg, 250 mg, 220 mg, 180 mg, 150 mg, 100 mg, 80 mg, 50 mg, 30 mg, 15 mg, and the like. Examples of lower limit include 0.1 mg, 0.2 mg, 1 mg, 2 mg, 3 mg, 4 mg, 10 mg, 15 mg, and the like. Examples of a preferred range include any combination of these upper limits and lower limits. The daily amount of drug penetration can be 0.1 to 100 mg, 0.1 to 80 mg, 0.1 to 60 mg, 0.1 to 20 mg, preferably 0.2 to 10 mg, 1 to 60 mg. Examples of the upper limit thereof include 100 mg, 80 mg, 60 mg, 40 mg, 30 mg, 20 mg, 10 mg, 8 mg, 7 mg, 5 mg, 3 mg, and the like. Examples of the lower limit include 0.1 mg, 0.2 mg, 1 mg, 1.5 mg, 3 mg, and the like. Examples of a preferred range include any combination of these upper limits and lower limits. The dosing frequency can be appropriately adjusted depending on the property of the composition. If the composition is a transdermally administered formulation, the frequency is for example once every 12 hours to once every 7 days. Any frequency therebetween can also be selected, such as once a day, once every 2 days, once every 3 days, once every 4 days, or the like, preferably once a day. If the composition is an injection formulation, the frequency is, for example, once daily to once every 3 months. Any frequency therebetween can be selected, such as once a week, once every two weeks, once every 4 weeks, once every 3 months, or the like. It is also possible to adjust the dosing time depending on the symptom with a pump-style automatic injector for sustained administration for 24 hours, or for administration only when the patient is awake. The agent can be mixed with a formulation comprising levodopa and sustainably administered. In a preferred example, the agent can be mixed with a formulation comprising levodopa and sustainably administered.

In the present invention, tandospirone or a pharmaceutically acceptable salt or prodrug thereof is preferably administered so that the human blood (plasma) tandospirone concentration is 0.05 to 20 ng/mL as the amount converted in terms of a free form in a period during which levodopa is desired to be active. Specifically, the period is 12 hours or longer, preferably 16 hours or longer per day.

Examples of the human blood (plasma) tandospirone concentration include 0.05 to 20 ng/mL, 0.5 to 15 ng/mL, 0.1 to 10 ng/mL, 0.5 to 15 ng/mL, 0.5 to 12 ng/mL, 0.1 to 15 ng/mL, 1 to 15 ng/mL, 1 to 12 ng/mL, 2 to 10 ng/mL, and the like as an amount converted in terms of free form. Examples of the upper limit thereof include 20 ng/mL, 15 ng/mL, 12 ng/mL, 10 ng/mL, 8 ng/mL, 5 ng/mL, 4 ng/mL, 3 ng/mL, 2 ng/mL, 1 ng/mL, and the like. Examples of the lower limit include 0.01 ng/mL, 0.02 ng/mL, 0.05 ng/mL, 0.1 ng/mL, 0.2 ng/mL, 0.5 ng/mL, 1 ng/mL, 2 ng/mL, and the like. Examples of a preferred range include any combination of these upper limits and lower limits. The aforementioned human blood (plasma) tandospirone concentration can be attained with a single administration or as a maintenance concentration by repeated administration.

In the present invention, examples of the maximum value (Cmax) of human blood (plasma) tandospirone concentration include 0.1 to 20 ng/mL, 0.2 to 15 ng/mL, 0.3 to 12 ng/mL, 0.3 to 10 ng/mL, 1 to 15 ng/mL, 1 to 12 ng/mL, 1 to 10 ng/mL, 2 to 10 ng/mL, and the like as an amount converted in terms of free form. Examples of the upper limit thereof include 20 ng/mL, 15 ng/mL, 12 ng/mL, 10 ng/mL, 8 ng/mL, 5 ng/mL, 4 ng/mL, 3 ng/mL, 2 ng/mL, 1 ng/mL, and the like. Examples of the lower limit include 0.1 ng/mL, 0.2 ng/mL, 0.5 ng/mL, 1 ng/mL, 2 ng/mL, and the like. Examples of a preferred range include any combination of these upper limits and lower limits.

In the present invention, examples of the area under the human blood (plasma) tandospirone concentration-time curve (AUC) include 3 to 700 ng·h/mL, 3 to 500 ng·h/mL, 3 to 300 ng·h/mL, 3 to 200 ng·h/mL, and the like as an amount converted in terms of free form. Examples of the upper limit thereof include 700 ng·h/mL, 500 ng·h/mL, 600 ng·h/mL, 400 ng·h/mL, 300 ng·h/mL, 200 ng·h/mL, 150 ng·h/mL, 100 ng·h/mL, 50 ng·h/mL, and the like. Examples of the lower limit include 3 ng·h/mL, 5 ng·h/mL, 10 ng·h/mL, 20 ng·h/mL, 30 ng·h/mL, and the like. Examples of a preferred range include any combination of these upper limits and lower limits. Examples of a preferred range include any combination of these upper limits and lower limits. The area under the tandospirone concentration-time curve (AUC) can be calculated by a method of analyzing pharmacokinetics. For example, a value from 0 to 48 hours, 0 to 72 hours, or 0 to the time of final measurement, or a value extrapolated infinitely is calculated.

In the present invention, a composition comprising tandospirone or a pharmaceutically acceptable salt or prodrug thereof is a composition characterized by being administered so that the human blood (plasma) tandospirone concentration is 0.05 to 20 ng/mL, 0.1 to 15 ng/mL, 0.1 to 10 ng/mL, 0.5 to 15 ng/mL, 0.5 to 12 ng/mL, 1 to 15 ng/mL, 1 to 12 ng/mL, 2 to 10 ng/mL or the like for 8 to 16 hours, more preferably 8 to 20 hours after administration of the tandospirone or a pharmaceutically acceptable salt or prodrug thereof, or for 12 hours or longer, preferably 16 hours or longer, and more preferably 18 hours or longer per day. The human blood (plasma) tandospirone concentration described above can be achieved with a single administration, or achieved as a concentration maintained by repeated administration (also considered as a steady state). The blood concentration in a steady state can be calculated by a method stacking single administrations. For concentration maintained by repeated administration (steady state), the time after administration refers to the time after the last administration.

Tandospirone or a pharmaceutically acceptable salt thereof is administered herein so that a maximum blood concentration of human blood (plasma) tandospirone in a steady state is 1 to 15 ng/mL, and a ratio of a minimum concentration, with respect to the maximum concentration of human blood (plasma) tandospirone concentration as 100%, is 30 to 95% and preferably 35 to 85% after administration of the tandospirone or a pharmaceutically acceptable salt thereof.

In the present invention, if the composition comprising tandospirone or a pharmaceutically acceptable salt or prodrug thereof is a transdermally administered formulation, the formulation application area thereof can generally be adjusted when appropriate, but the total application area per dose is preferably 1 to 200 $cm^2$, 1 to 100 $cm^2$, 2 to 80 $cm^2$, 9 to 60 $cm^2$, and the like. Examples of the upper limit thereof include 200 $cm^2$, 160 $cm^2$, 130 $cm^2$, 100 $cm^2$, 80 $cm^2$, $cm^2$, 50 $cm^2$, 40 $cm^2$, 30 $cm^2$, 20 $cm^2$, and the like. Examples of the lower limit include 1 $cm^2$, 2 $cm^2$, 4 $cm^2$, 9 $cm^2$, and the like. Examples of a preferred range include any combination of these upper limits and lower limits, which enables a preferred therapeutic effect to be attained.

The tandospirone or a pharmaceutically acceptable salt or prodrug thereof of the invention exceeds the lower limit value of the human blood (plasma) tandospirone concentration within 8 hours, preferably within 6 hours, and more preferably within 4 hours after a single dose, and the human blood (plasma) tandospirone concentration is maintained in the range between the upper limit and the lower limit for up to 16 hours, preferably up to 18 hours, and more preferably up to 20 hours after the single dose.

The tandospirone or a pharmaceutically acceptable salt or prodrug thereof of the present disclosure preferably has a pharmacokinetic profile of reaching the maximum blood concentration (Cmax) more gradually and being eliminated more gradually relative to oral administration.

The time to reach the maximum blood concentration (Cmax) (mean value) is, for example, between 16 hours and 36 hours or between 20 hours and 32 hours after a single dose. Examples of the lower limit for the time to reach the maximum blood concentration (Cmax) (mean value) include 16 hours, 20 hours, and 24 hours. Examples of the upper limit (mean value) include 36 hours and 32 hours. The half-life (mean value) is, for example, between 3 and 20 hours. Examples of the lower limit for the half-life (mean value) include 3 hours, 4 hours, 5 hours, 6 hours, and the like. Examples of the upper limit (mean value) include 20 hours, 18 hours, 16 hours, 14 hours, and the like.

The following protocol described in a reference document (J Clin Invest. (2014) 124(3):1340-1349.) can be referred to as a suitable clinical evaluation that can confirm the efficacy of the pharmaceutical composition of the invention on dyskinesia in Parkinson's disease. Specifically, brain function image analysis using positron emission tomography (PET) of striatal dopamine D2 receptor is performed on patients with a dyskinesia symptom. This can be utilized in estimating the degree of progression of pathological condition or the effective drug concentration or determining the therapeutic effect.

For example, [$^{11}$C] raclopride can be used as a PET tracer of a dopamine D2 receptor expressed in the striatal dopamine nerve post synapse. The amount of change in released dopamine in the striatum can be evaluated by measuring the amount of change in striatal [$^{11}$C] raclopride binding relative to a baseline (OFF state) from levodopa administration or concomitant use of the pharmaceutical composition of the invention with levodopa administration by [$^{11}$C] raclopride PET.

It has been reported that the amount of change in striatal [$^{11}$C] raclopride receptor binding in Parkinson's disease is related to progression in the pathological state of Parkinson's disease, motor fluctuations, or dyskinesia (reference document: Brain. (2004) 127:2747-2754.)

The result of evaluating the striatal dopamine level under the conditions for the PET test in the aforementioned reference document can be understood as follows.

For example, it is known that the "amount of change in striatal [$^{11}$C] raclopride receptor binding from before levodopa administration to 1 hour after administration (also abbreviated as the amount of change B/1 h)" is higher in Parkinson's disease patients with motor fluctuations or dyskinesia compared to patients without motor fluctuations or dyskinesia, such as by 10% or greater or 15% or greater. If the amount of change B/1 h decreases due to drug therapy, this means that the therapy is effective on motor complications such as dyskinesia. The pharmaceutical composition of the invention is expected to reduce the amount of change B/1 h. In particular, the amount of change B/1 h is reduced in Parkinson's disease patients who have a significantly higher amount of change B/1 h than patients without motor fluctuations or dyskinesia. The composition is also expected to have a therapeutic effect on motor complications such as dyskinesia. Therapy with the pharmaceutical composition of the invention is expected to reduce the amount of change B/1 h to, for example, less than 10%.

For example, it is known that the absolute value of the "amount of change in striatal [$^{11}$C] raclopride receptor binding from 1 hour after levodopa administration to 4 hours after administration (also abbreviated as the amount of change 1 h/4 h)" is higher in Parkinson's disease patients with motor fluctuations or dyskinesia compared to patients without motor fluctuations or dyskinesia, such as by 5% or greater. If the amount of change B/1 h decreases due to drug therapy, this means that the therapy is effective on motor complications such as motor fluctuations. The pharmaceutical composition of the invention is expected to reduce the amount of change B/1 h. In particular, the amount of change 1 h/4 h is reduced in Parkinson's disease patients with motor fluctuations or dyskinesia who have a significantly higher amount of change B/1 h than patients without motor fluctuations or dyskinesia. The composition is also expected to have a therapeutic effect on motor complications such as motor fluctuations. Therapy with the pharmaceutical composition of the invention is expected to reduce the amount of change 1 h/4 h to, for example, less than 5%.

For example, a decrease in the "ratio of amount of change in striatal [$^{11}$C] raclopride receptor binding from before levodopa administration to 1 hour after administration after therapeutic intervention with the pharmaceutical composition of the invention (also abbreviated as the amount of change B/1 h after therapy) with respect to the amount of change in striatal [$^{11}$C] raclopride receptor binding from before levodopa administration to 1 hour after administration before therapy with the composition of the invention (also abbreviated as the amount of change B/1 h before therapy) when this is 100% (also abbreviated as the ratio of change B/1 h)" means that therapy is effective on motor complications such as dyskinesia. The pharmaceutical composition of the invention is expected to reduce the ratio of change B/1 h, and can reduce the ratio of change B/1 h to, for example, 90% or less, preferably 80% or less, and more preferably 70% or less upon a PET test under the conditions reported in a document.

For example, a decrease in the "ratio of amount of change in striatal [$^{11}$C] raclopride receptor binding from 1 hour after levodopa administration to 4 hours after administration after therapeutic intervention with the pharmaceutical composition of the invention (also abbreviated as the amount of change 1 h/4 h after therapy) with respect to the amount of change in striatal [$^{11}$C] raclopride receptor binding from 1 hour after levodopa administration to 4 hours after administration before therapy with the composition of the invention (also abbreviated as the amount of change 1 h/4 h before therapy) (also abbreviated as the ratio of change 1 h/4 h)" in a Parkinson's disease patient with motor fluctuations or dyskinesia means that therapy is effective on motor complications such as motor fluctuations. The pharmaceutical composition of the invention is expected to reduce the ratio of change 1 h/4 h, and can reduce the ratio of change 1 h/4 h to, for example, 90% or less, preferably 80% or less, and more preferably 70% or less upon a PET test under the conditions reported in a document.

As the measurement point before levodopa administration, the amount can be measured at a time at which sufficient time has passed after levodopa administration and an effect of levodopa is not found.

As the measurement point at 1 hour after administration, the amount can be measured at a determined time at 1 to 2 hours after levodopa administration.

As the measurement point at 4 hours after administration, the amount can be measured at a determined time at 4 to 8 hours after levodopa administration.

For the amount of striatal [$^{11}$C] raclopride receptor binding,

Amount of change B/1 h (%)=(amount of receptor binding before levodopa administration−amount of receptor binding 1 hour after levodopa administration)÷amount of receptor binding before levodopa administration×100

Amount of change B/4 h (%)=(amount of receptor binding before levodopa administration−amount of receptor binding 4 hours after levodopa administration)÷amount of receptor binding before levodopa administration×100

Amount of change 1 h/4 h (%)=|amount of receptor binding 1 hour after levodopa administration−amount of receptor binding 4 hours after levodopa administration|÷amount of receptor binding 1 hour after levodopa administration×100

For the amount of striatal [$^{11}$C] raclopride receptor binding,

Ratio of change B/1 h (%)=amount of change B/1 h after therapy with the composition of the invention÷amount of change B/1 h before therapy with the composition of the invention×100

Ratio of change 1 h/4 h (%)=amount of change 1 h/4 h after therapy with the composition of the invention÷amount of change 1 h/4 h before therapy with the composition of the invention×100

The therapeutic effect of the pharmaceutical composition of the invention on motor complications such as motor fluctuations and dyskinesia can be studied by comparing dyskinesia expression time, ON time, OFF time, plasma drug concentration (levodopa or agent), or the like based on an amount of change in [$^{11}$C] raclopride receptor binding, a clinical evaluation scale such as UPDRS, MDS-UPDRS, UDysRS, CDRS, Rush DRS, AIMS, EQ-5D-5L, PDQ-39, CGI, or PGI, ON time or OFF time described in a patient diary, a scale calculated from locomotive movement information obtained from a wearable device such as an accelerometer and/or angular velocimeter, or the like in a placebo treated patient group and a drug treated patient group.

The protocol such as the target patient, dosing period, dosage of agent, or evaluation method in the test described above can be appropriately modified (these tests can be appropriately conducted by those skilled in the art by referring to J Clin Invest (2014) 124 (3) 1340-1349, Mov Disord. (2017) 32(2): 235-240, or the like.

In the present invention, a tandospirone transdermally administered formulation is provided for therapy of Parkinson's disease by concomitant use with a drug used for Parkinson's disease such as a levodopa containing formulation. The tandospirone transdermally administered formulation in the present invention can be expected to have a preferred effect by administration of a levodopa containing formulation after 6 hours, preferably after 8 hours, and more preferably after 12 hours from application of the tandospirone transdermally administered formulation. Further, a stable therapeutic effect is attained without depending on the timing of administering a levodopa containing formulation by repeatedly administering a tandospirone transdermally administered formulation by replacing the formulation every predetermined amount of time.

A manufacturing method of the transdermally administered formulation of the invention is described hereinafter, but the present invention is not limited thereto.

The transdermally administered formulation of the invention can be manufactured by a commonly known method. The tape agent of the invention can be manufactured, for example, according to the following Manufacturing Example 1.

Manufacturing Example 1

A common manufacturing method of tape agents (transdermal patch) is described.

The tape agent of the invention can be manufactured by a common method. For example, the tape agent can be manufactured in accordance with the section directed to the manufacture of plaster agents described in "Keihi Tekiyo Seizai Kaihatsu Manyuaru" [Development manual for transdermally applied formulation], supervised by Mitsuo Matsumoto (1985). The tape agent can also be manufactured, for example, by an apparatus, method, or the like described in "Development of Portable Equipment for Manufacturing Transdermal Patches (MEMBRANE), 32(2), 116-119 (2007))".

Specifically, a common manufacturing method of adhesive tape can be applied for forming an adhesive layer in the manufacture of the tape agent of the invention. A typical example thereof is a solvent coating method, but hot melt coating method, electron beam curing emulsion coating method, or the like can also be used.

To form an adhesive layer using the solvent coating method, tandospirone, adhesive containing mixture, penetration enhancer, curing agent, and other formulation components are mixed with an organic solvent to prepare an adhesive layer mixture, and the mixture is applied to one side of a support or a release liner and dried, then the organic solvent is removed, and the release liner or support is pasted on before or after drying. The thickness of an adhesive layer of a tape agent is not particularly limited, but is preferably about 10 μm to about 600 μm, 10 μm to about 400 μm, more preferably about 20 μm to about 200 μm, still more preferably about 50 μm to about 180 μm, and especially preferably about 70 μm to about 150 μm.

Manufacturing Example 2

Preparation of Other Parenterally Administered Formulations

An ointment can be manufactured by a commonly known method. An oil and fat ointment can generally be manufactured by heating and melting an oil and fat substrate of hydrocarbons or the like such as oil and fat, wax, or paraffin, adding an active ingredient, mixing to dissolve or disperse the active ingredient, and mixing and kneading until the entire mixture is homogeneous. A water soluble ointment can generally be manufactured by heating and melting a water soluble substrate such as macrogol, adding an active ingredient, and mixing and kneading until the entire mixture is homogenous.

An ointment can be manufactured by blending tandospirone with higher alcohols such as cetanol or stearyl alcohol, higher fatty acid such as myristic acid, lauric acid, palmitic acid, stearic acid, or linoleic acid or an ester thereof, wax such as purified lanolin or spermaceti, surfactant such as sorbitan fatty acid ester or sucrose fatty acid ester, and hydrocarbons such as hydrophilic petrolatum, liquid paraffin, or plastibase. The composition of such an ointment formulation is, for example, 0.5 to 10% by weight of tandospirone, 0.1 to 5% of higher alcohol, 1 to 15% by weight of higher fatty acid or ester thereof, 1 to 10% by weight of surfactant, 4 to 10% by weight of wax, and 50 to 80% by weight of hydrocarbon. An ointment can be obtained, for example, by a manufacturing method comprising adding tandospirone and the aforementioned additive components and mixing the ingredients while heating, and maintaining a temperature of 50 to 100° C., and once all the ingredients become a transparent dissolved solution, mixing the ingredients homogenously with a homogenizer mixer, and then stirring while cooling and allowing the mixture to cool.

An injection agent or formulation for subcutaneous, intradermal, or intramuscular administration can be manufactured by a commonly known method. Such an injection agent can generally be manufactured by the following method.

(i) An active ingredient is filled directly, or an active ingredient with an addition of an additive is dissolved, suspended, or emulsified into injection water, other aqueous or non-aqueous solution or the like and homogenized, and the solution is filled into an injection container, sealed, and sterilized.

(ii) An active ingredient is filled directly, or an active ingredient with an addition of an additive is dissolved, suspended, or emulsified into injection water, other aqueous or non-aqueous solution, or the like and homogenized, and the solution is aseptically filtered or aseptically prepared and homogenized and then filled into an injection container and sealed.

The injection agent can also be manufactured as a lyophilized injection agent or powder injection agent to prevent degradation or inactivation of the active ingredient in a solution.

A lyophilized injection agent can generally be manufactured by filling an active ingredient directly, or filling an active ingredient and an additive such as an excipient, which are dissolved into injection water and aseptically filtered, into a container for an injection agent and then lyophilizing, or lyophilizing the ingredient in a specialized container and then directly filling a container therewith.

A powder injection agent can generally be manufactured by filling a container for an injection agent with powder obtained by filtration with an aseptic filter and then crystallization or the powder with addition of a sterilized additive.

For example, an active ingredient solution is prepared by dissolving tandospirone in water, organic solvent, or mixture of water and organic solvent, together with a surfactant. The resulting solution can be filtered and sterilized with a sterilization filter to prepare an aseptic active ingredient solution. In this regard, the solvent used for the dissolution (water, organic solvent, or mixture of water and organic solvent) is preferably an organic solvent or a mixture of an organic solvent and water, and more preferably a mixture of an organic solvent and water. A sterilization filter is effective for filtration and sterilization, as well as removal of foreign objects originating from raw materials or exogenous foreign objects mixed in during the manufacturing process.

Examples of surfactants include polysorbate 80, polysorbate 20, polyoxyethylene hydrogenated castor oil 50, polyoxyethylene hydrogenated castor oil 60, poloxamer 188, polyoxyethylene castor oil, benzalkonium chloride, sodium lauryl sulfate, and the like, and two or more thereof can also be used. A surfactant is preferably polysorbate 80. A surfactant is preferably used at about 0.005% (w/v) to about 10% (w/v).

As the water, purified water, water of the same or higher grade than purified water, or injection water is used. Examples of organic solvent include alcohol solvents (e.g., methanol, ethanol, and the like), aprotic solvents (e.g., acetone, dimethyl sulfoxide, N,N-dimethylacetamide, and the like), and the like, or two or more solvents can be used. The organic solvent is preferably 1-propanol, methanol, ethanol, 2-propanol, acetone, dimethyl sulfoxide, or N,N-dimethylacetamide.

The injection agent of the invention can be intramuscularly or subcutaneously injected after attaching an injection needle to a prefilled syringe filled with a formulation. The injection agent can also be administered by aspirating a formulation from a container such as vial filled with the formulation into an injection syringe via an injection needle and then discharging the formulation intramuscularly or subcutaneously. Furthermore, a formulation can be a lyophilized formulation obtained by filling the formulation into a container such as a vial and lyophilizing the formulation, or a powder filled formulation prepared by filling dried powder crystal obtained by isolating and then drying the active ingredient crystal in the formulation in a container such as a vial. Lyophilized formulations and powder filled formulations can be intramuscularly or subcutaneously injected after aspirating a suspension prepared by suspending the formulation in a container with a suspension solution at the time of use from the container into an injection syringe via an injection needle. The injection agent of the invention can also be intramuscularly or subcutaneously injected after placing a container filled with a formulation on a needleless syringe (syringe capable of administration without an injection needle by utilizing pressure generated by gas, initiating agent, spring, or the like incorporated into an injection device, and having a mechanism for discharging the drug solution filled in the container).

Example of Preparing a Sustained Injection Pump

The injection agent of the invention can be sustainably administered by using a commercially available subcutaneous sustained injection pump. A subcutaneous sustained injection pump is an apparatus for subcutaneously injecting a drug sustainably to a patient via an injection tube, having a drug storage unit and a pump for sustained injection of the drug. Such an apparatus generally has a built-in clock and program that can change the amount of injection per a certain period of time. A drug storage unit is a sealed container filled with a drug solution adjusted to a drug concentration required for the drug efficacy, comprising a drug inlet and outlet for connection to the pump. A pump is a pump that can sustainably inject the drug solution precisely at a minute amount, which is an apparatus that can injection a minute amount of liquid from about 0.1 mL/day to 10 mL/hr. A drug storage unit is filled with and stores an aseptically guaranteed tandospirone solution.

A sustained injection agent is an injection agent that is applied subcutaneously, intradermally, intramuscularly, or the like in order to release an active ingredient over a long period of time. A sustained injection agent can be manufactured by a commonly known method, generally by dissolving or suspending an active ingredient in plant oil or the like, or by preparing a suspension of microspheres using biodegradable macromolecular compounds.

An implanted agent is a solid or gel-like injection agent applied using an instrument for implantation under the skin, in the muscle, or the like, or by surgery in order to release an active ingredient over a long period of time. An implanted agent can be manufactured by a commonly known method. An implanted agent can generally be obtained by using a biodegradable macromolecular compound to prepare a pellet, microsphere, or gel-like formulation.

(Combined Drug)

The transdermally administered formulation of the invention can be concomitantly used with an existing therapeutic agent for Parkinson's disease other than levodopa. Examples of such an existing therapeutic drug for Parkinson's disease include, but are not limited to, dopamine agonists (e.g., bromocriptine, pergolide, talipexole, cabergoline, pramipexole, ropinirole, rotigotine, and the like), monoamine oxidase B (MAOB) inhibitors (e.g., selegiline, rasagiline, and Safinamide), catechol-O-methyltransferase (COMT) inhibitors (e.g., entacapone), amantadine, apomorphine, istradefylline, anticholinergic drugs (e.g., biperiden, trihexyphenidyl, profenamine, and mazaticol), tiapride, droxidopa, carbidopa, zonisamide, and the like.

The present invention is specifically described in more detail with Reference Examples, Examples, and Test Examples, but the present invention is not limited thereto. The compound names used in the following Reference Examples, Examples, and the like do not necessarily follow the IUPAC nomenclature.

EXAMPLES

The Examples are described hereinafter.

While the products described in the Examples were used as the specific reagents, the products can be substituted with an equivalent product from other manufacturers (Sigma-Aldrich, Wako Pure Chemical, Nacalai Tesque, R&D Systems, USCN Life Science INC, or the like).

(Manufacturing Example)

Reference Manufacturing Example 1: Manufacture of Tandospirone

Tandospirone ((1R,2S,3R,4S)—N-[4-[4-(pyrimidine-2-yl) piperadine-1-yl]butyl]-2,3-bicyclo[2.2.1]heptanedicarboximide) has the chemical formula set forth below. The manufacturing method thereof is described in Japanese Laid-Open Publication No. 58-126865. The description thereof is incorporated herein by reference.

[Chemical Formula 1]

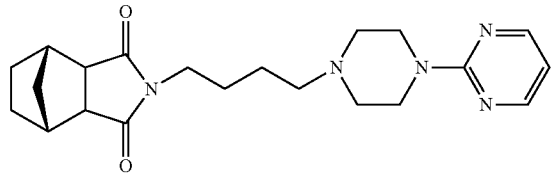

(Reference Manufacturing Example: Manufacture of Tandospirone Tape Agent)

(Manufacture of Tandospirone Tape Agent)

An acrylic adhesive (MAS683, CosMED Pharmaceutical Co. Ltd., 35.6% by weight solids, 12.5068 g), ethyl acetate (1.5 mL), and polyoxyethylene lauryl ether (0.2530 g) were mixed. An ethyl acetate (5.5 mL) solution of tandospirone (0.32512 g) was prepared and added to the mixture of adhesive and thoroughly stirred. The resulting mixture was spread on a support and dried for one day at room temperature. A release liner was then pasted therewith to manufacture a tandospirone tape agent.

(Manufacture of Placebo Tape Agent)

An acrylic adhesive (MAS683, CosMED Pharmaceutical Co. Ltd., 35.6% by weight solids, 18.6962 g), ethyl acetate (5.5 mL), and polyoxyethylene lauryl ether (0.3520 g) were mixed and thoroughly stirred. The resulting mixture was spread on a support and dried for one day at room temperature. A release liner was then pasted therewith to manufacture a placebo tape agent.

50.8 μm of polyethylene terephthalate and/or ethylene vinyl acetate copolymer laminate film (Scotchpak #9732) from 3M Health Care Ltd. was used as the support. Bynasheet 64S-018B from Fujimori Kogyo Co., Ltd. was used as the release liner.

TABLE 1

Table. Drug content in tandospirone tape agent

| | Thickness (μm) | Tandospirone content (mg/cm$^2$) |
|---|---|---|
| Formulation 1 | 99 | 0.6 |
| Formulation 2 | 94 | 0.6 |
| Formulation 3 | 114 | 0.7 |
| Formulation 4 | 105 | 0.7 |
| Formulation 5 | 150 | 1.0 |

Measurement of Amounts of Drug (Drug Dosage) and Residual Drug in Tape Agent

While an example of measurement conditions for the drug dosage and amount of residual drug is described below, another measurement method verified to be able to measure drug dosage or amount of residual drug of tandospirone can be used instead.

<Example of Measurement Conditions>

Preparation of Standard Solution

A tandospirone solution (about 4, 20, or 100 μg/mL) is prepared.

Preparation of Formulation Solution (1) A tape agent is placed in a container. 10 mL of acetone is added, and ultrasound wave is irradiated thereon for 30 minutes.

(2) 1 mL of methanol is added to 1 mL extract of (1) and mixed.

(3) The solution is filtered with a filter (Millipore: Millex-FH (0.45 μm, PTFE)).

High Performance Liquid Chromatography (HPLC) Condition

Column: YMC-Pack ODS-AM 250×4.6 mm (particle size: 5 μm)

Column oven: 40° C.

Detector: ultraviolet absorption spectrophotometer (measurement wavelength: 240 nm)

Flow rate: 0.9 mL/min

Amount injected: 10 μL

Mobile phase: 10 mM phosphate buffer (pH 6.8)/acetonitrile mixture (35:65)

(Evaluation of Plasma Concentration)

1. Testing Method 1.1. Pretreatment Operation Method

50 μL of rat plasma sample was fractionated into a polypropylene microtube. 50 μL of methanol (50 μL of standard solution for calibration curve sample) and 200 μL of internal standard solution (Bezafibrate methanol solution: 200 nmol/L, 200 μL of methanol for blank sample) are added and stirred for about 10 seconds with a mixer. This is centrifuged (4° C., 4500 rpm, 10 min), and then the supernatant is subjected to vacuum filtration using a filter (FastRemover MF 0.2 μm). 70 μL of aqueous 10 mmol/L ammonium acetate solution is added to 70 μL of the resulting filtrate and stirred for about 10 seconds with a mixer to prepare a measurement sample.

The tandospirone concentration is measured by liquid chromatography-mass spectrometry.

1.2. Measurement Conditions

Column: XSELECT CSH C18, 3.5 μm, 100×3.0 mm I.D.

Column temperature: 50° C.

Mobile phase A: aqueous 10 mmol/L ammonium acetate solution

Mobile phase B: methanol

Flow rate: 0.6 mL/min

Gradient Condition:

TABLE 2

| Time (min) | 0 | 0.10 | 5.00 | 6.00 | 6.01 | 9.00 |
|---|---|---|---|---|---|---|
| Mobile phase B(%) | 15 | 15 | 95 | 95 | 15 | 15 |

Ionization method: electrospray ionization

Detection method: multiple reaction monitoring, positive ion detection mode

Monitor ion: 384.2/122.1 (tandospirone Q1/Q3, m/z), 362.02/138.9 (Bezafibrate Q1/Q3, m/z)

Example 1: Evaluation of Changes in Plasma Concentration when Tandospirone Tape Agent is Applied to a Normal Rat (Testing Method)

Wistar male rats (14-week old, Japan SLC, Inc.) were used. The abdominal regions of the rats were shaved prior to the tape agent evaluation date, and the tape agent of formula 1 was applied to the abdominal regions on the evaluation date (the size was 9 cm$^2$). Blood was collected over time after 2, 4, 6, and 24 hours from administration by the application to analyze the plasma tandospirone concentration. The results are indicated by mean value±standard deviation.

(Results)

Changes in the plasma tandospirone concentration shown in FIG. 1 were observed by applying a tandospirone tape agent (9 cm$^2$: 31±2 cm$^2$/kg). It was confirmed that the tape agent smoothed out and sustained the blood concentration of tandospirone.

Example 2: Evaluation of the Dyskinesia Improving Effect of Tandospirone Tape Agent A rat striatum dopaminergic denervation model using topical administration of 6-hydroxydopamine (hereinafter, also referred to as "6-OHDA") to one side of the brain is known as a typical experimental model for PD-LID (rats treated on one side with 6-OHDA (6-OHDA-lesioned rats)). Dyskinesia-like abnormal involuntary movements (AIMs) manifest in said model with repeated administration of levodopa (Lundblad et al., European Journal of Neuroscience, 2002, 15: 120-132, Winkler et al., Neurobiology of Disease, 2002, 10: 165-186).

(Testing Method)

Wistar male rats (12-week old, Japan SLC, Inc.) were used for the preparation of animal models. Desipramine hydrochloride (25 mg/kg; Wako Pure Chemical) was intraperitoneally administered. After 30 minutes from the administration, the rats were subjected to isoflurane inhalational anesthetic using a general anesthesia apparatus for experimental animals. Under isoflurane anesthesia, the rats were immobilized to a brain stereotaxic instrument. The skin on the head was incised with a surgical scalpel to expose the skull. The coordinates of the bregma used as the origin (AP: 0, ML: 0, DV: 0) was determined, and the coordinates of the right medial forebrain bundle (AP: −4.4 mm, ML: 1.5 mm, DV: 7.8 mm from bregma) were measured. After inserting an injection tube for administration at the measured coordinates, 6-OHDA (9 μg/4 μL; Sigma-Aldrich) inducing dopaminergic denervation was topically injected. After 2 weeks from surgery, apomorphine hydrochloride hemihydrate (0.5 mg/kg; Wako Pure Chemical) was subcutaneously administered, and the rotation movement to the opposite side from the 6-OHDA injected site was observed. Rats with 7 rotations or more per minute were used as rats treated on one side with 6-OHDA.

To make a PD-LID model, a mixture of levodopa methyl ester hydrochloride (6 mg/kg; Sigma-Aldrich) dissolved in saline and benserazide hydrochloride (15 mg/kg; Sigma-Aldrich) (hereinafter, also referred to as "levodopa containing solution") was intraperitoneally administered once daily to 6-OHDA-lesioned rats. The levodopa containing solution was repeated administered for 3 weeks or longer to observe and evaluate the behavior. The behavior was observed and evaluated in a transparent acrylic cage for 1 minute every 20 minutes after 20 minutes from the intraperitoneal administration of the levodopa containing solution, up until after 3 hours from administration. Observation of behavior was classified into Limb AIMs (involuntary bending or stretching of front limbs on the opposite side of the disorder, opening/closing of hands, up and down movement of the wrist, chorea-like tremor, dystonia-like stiffening), Axial AIMs (twisting of the upper body/neck to the opposite side of the disorder, losing balance and falling, or maintaining an unstable posture), Orolingual AIMs (trembling of the jaw or violently sticking out the tongue forward), and Locomotive behavior (rotational behavior to the other side of the destruction), and was given a score from 0 to 4 (0: none, 1: less than 30 seconds of manifestation, 2: 30 seconds or more of manifestation, 3: constantly, but stopped with a stimulus such as sound, and 4: constant manifestation, which does not stop with a stimulus such as sound). The sum of the scores for Limb AIMs, Axial AIMs, and Orolingual AIMs in 3 hours was used as the total AIMs score. Individuals with a total AIMs score of less than 10 were excluded from the test as not manifesting a dyskinesia-like symptom. The behavior was observed and evaluated before the drug evaluation date. The rats were assigned to each dosing group by using the 3 hour AIMs score, Locomotive behavior score, and rat body weight as indicators, which were used for evaluation of drugs.

(Transdermal Administration (Condition 1))

When evaluating a tape agent, the hair on the abdominal region of rats was shaved before the evaluation date. The tape agent of formulation 2 was applied to the abdominal regions of rats on the evaluation date at 60 cm$^2$/kg (37 mg/kg). After 4 hours from application, a levodopa containing solution was intraperitoneally administered to observe and evaluate the behavior. Individuals with 50% or more of the tape agent coming off during the test were excluded from analysis. After the completion of observation and evaluation of behavior, plasma was collected to analyze the plasma tandospirone concentration.

(Transdermal Administration (Condition 2))

When evaluating a tape agent under stratum corneum stripping conditions (tandospirone high exposure conditions), stripping was performed 10 times at the abdominal region of rats using a transpore surgical tape (3M) on the evaluation date, and a tape agent of formulation 3 was then applied at 60 cm$^2$/kg (45 mg/kg). After 4 hours from application, a levodopa containing solution was intraperitoneally administered to observe and evaluate the behavior. Individuals with 50% or more of the tape agent coming off during the test were excluded from analysis. After the completion of observation and evaluation of behavior, plasma was collected to analyze the plasma tandospirone concentration.

When evaluating dyskinesia-like symptoms, the sum of the Limb AIMs, Axial AIMs, and Orolingual AIMs at each evaluation point was used as the AIMs score. Statistical analysis on test results was performed by Wilcoxon rank sum test using the total AIMs score, which is the sum of AIMs scores for 3 hours, and total AIMs score in 100 to 180 minutes as parameters. ** indicates p<0.01, meaning that there is a significant difference compared to the placebo tape agent application group. The results in the drawings are indicated in terms of mean value±standard error.

(Results)

Figure 2:
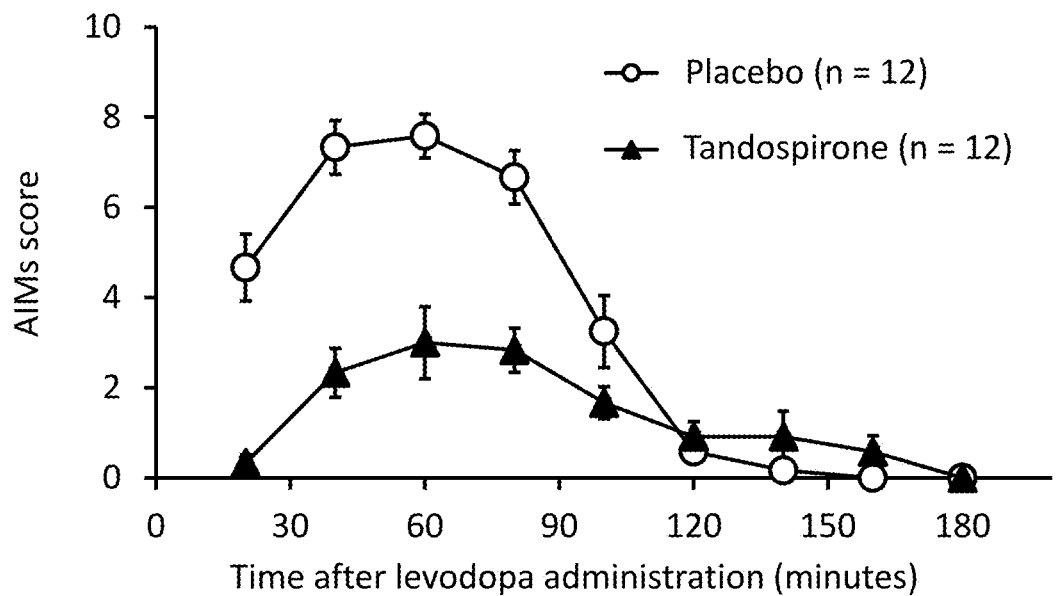
FIG. 2 is a diagram showing results of evaluating dyskinesia-like symptoms when a tandospirone tape agent was applied to a PD-LID rat model under administration condition 1. Specifically, a tandospirone tape agent was transdermally administered to a PD-LID rat model and levodopa was administered 4 hours later to evaluate dyskinesia-like symptoms. The results are indicated in terms of mean value±standard error. ** indicates $p<0.01$, meaning that there is a significant difference compared to a placebo tape agent application group (Wilcoxon rank sum test). In the figure, graph A shows the changes in AIMs score over time after levodopa administration. Graph B shows the total AIMs score in 180 minutes. Graph C shows the total AIMs score in 100 to 180 minutes.
Figure 2:
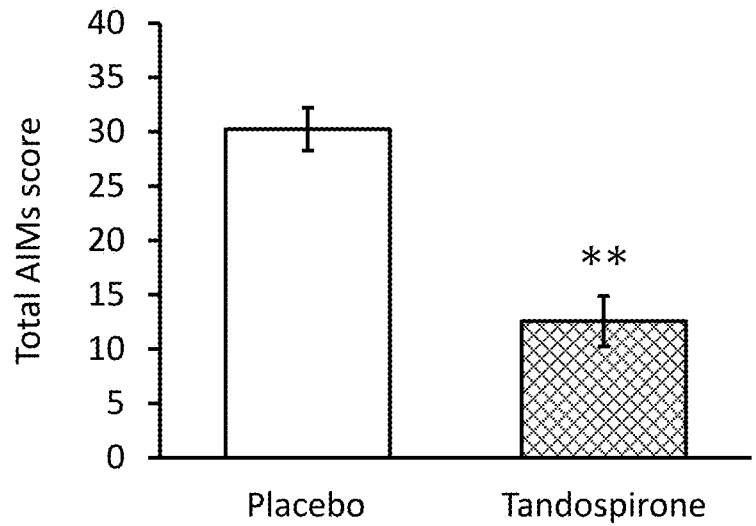
Figure 2:
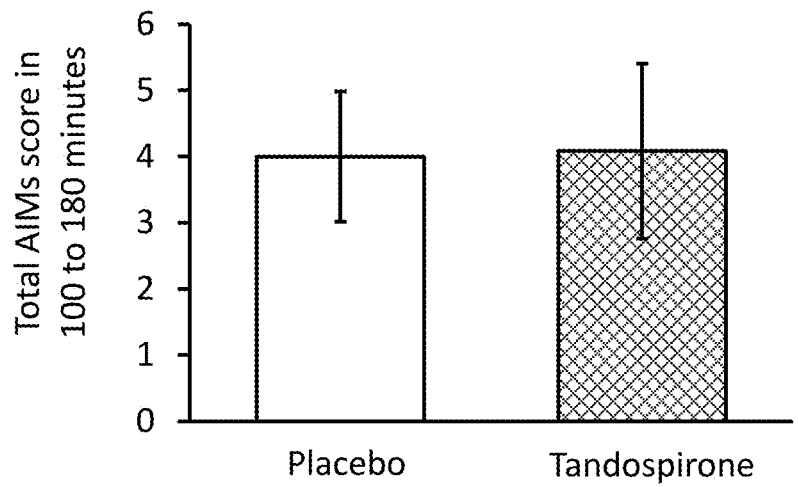

When tandospirone was transdermally absorbed by applying a tandospirone tape agent (formulation 2: drug dosage of 37 mg/kg) via transdermal administration (condition 1), the total AIMs score was 12.6. Compared to application of a placebo tape agent without tandospirone, the total AIMs score decreased 17.7, so that a significant improvement was observed in dyskinesia-like symptoms (FIG. 2, Graphs A and B). Further, a clear dyskinesia-like symptom (mean AIMs score of 2 or greater) was not observed for the placebo tape agent application group or the tandospirone tape agent application group at 120 to 140 minutes after levodopa administration. A significant difference was not found between the two groups in the total AIMs score in 100 to 180 minutes (FIG. 2, Graph C). The mean value of plasma tandospirone concentrations measured after the completion of observation and evaluation of behavior was 71.8 ng/mL.

Figure 3:
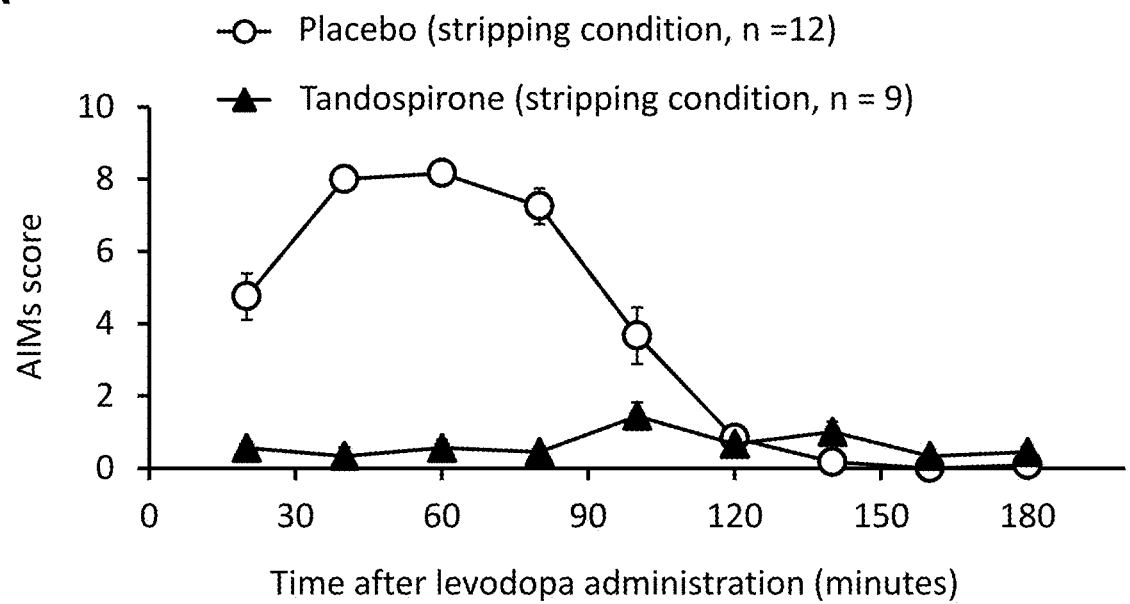
FIG. 3 is a diagram showing the results of evaluating dyskinesia-like symptoms when a tandospirone tape agent was applied to a PD-LID rat model under administration condition 2. Specifically, a tandospirone tape agent was transdermally administered to a PD-LID rat model on which stratum corneum stripping was performed on the tape agent application site, and levodopa was administered 4 hours later to evaluate dyskinesia-like symptoms. The results are indicated in terms of mean value±standard error. ** indicates p<0.01, meaning that there is a significant difference compared to a placebo tape agent application group (Wilcoxon rank sum test). In the figure, graph A shows the changes in AIMs score over time after levodopa administration. Graph B shows the total AIMs score in 180 minutes. Graph C shows the total AIMs score in 100 to 180 minutes.
Figure 3:
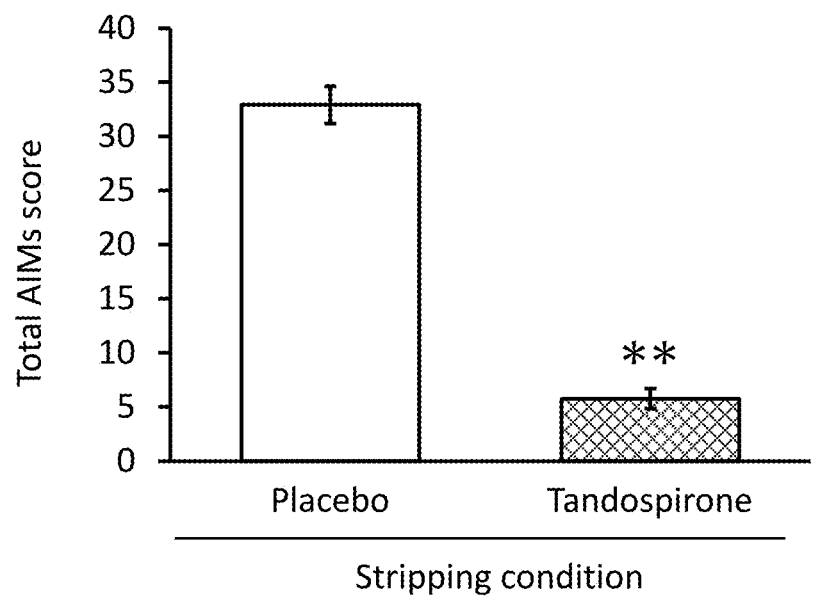
Figure 3:
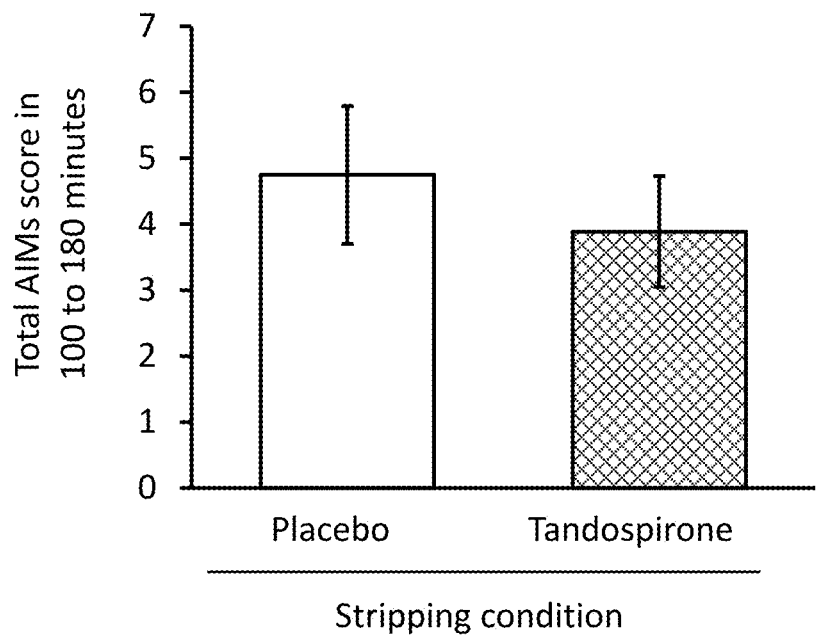

When a high exposure tandospirone was transdermally absorbed by applying a tandospirone tape agent (formulation 3: drug dosage of 45 mg/kg) under stratum corneum stripping conditions via transdermal administration (condition 2), the total AIMs score was 5.8. Compared to application of a placebo tape agent without tandospirone, the total AIMs score decreased 27.1, so that a significant improvement was observed in dyskinesia-like symptoms. A higher effect of improvement was observed under administration condition 2 than under administration condition 1 (FIG. 3, Graphs A and B). Further, a clear dyskinesia-like symptom (mean AIMs score of 2 or greater) was not observed for the placebo tape agent application group or the tandospirone tape agent application group at 120 to 140 minutes after levodopa administration under stratum corneum stripping conditions. A significant difference was not found between the two groups in the total AIMs score in 100 to 180 minutes (FIG. 3, Graph C). The mean value of plasma tandospirone concentrations measured after the completion of observation and evaluation of behavior was 269 ng/mL. The mean value of plasma tandospirone concentration under administration condition 2 was 3 times or higher than that under administration condition 1.

In view of the above results, tandospirone transdermally administered formulations improved PD-LID symptoms without a rebound symptom.

Further, it was found that the effect on PD-LID and anxiolytic action of tandospirone is exerted at the same dosage in a non-clinical model. The anxiolytic action was evaluated using a rat Vogel conflict test model, and the effect on PD-LID was evaluated in 6-OHDA-lesioned rats. Therefore, the therapeutic effect in the invention is exerted at the same blood concentration as tandospirone citrate tablets (Sediel tablets) commercially available as anxiolytic drugs.

Example 3: Evaluation of Dyskinesia Improving Effect Upon Continuous Subcutaneous Infusion of Tandospirone The efficacy of tandospirone on dyskinesia-like symptoms was evaluated by continuous subcutaneous infusion of tandospirone to PD-LID rat models.

(Testing Method)

As in Example 2, a levodopa containing solution was repeated administered to 6-OHDA-lesioned rats for 3 weeks or longer to observe and evaluate the behavior. The behavior was observed and evaluated before the drug evaluation date. The rats were assigned to each dosing group by using the 3 hour AIMs score, Locomotive behavior score, and rat body weight as indicators, which were used for evaluation of drugs. However, individuals with a total AIMs score of less than 10 were excluded from the test as lacking manifestation of a dyskinesia-like symptom. Individuals with a body weight deviating 10% or more from the mean body weight were also excluded from the test to minimize variation in the dosage for each individual.

Tandospirone (free form) was dissolved in 1 M hydrochloric acid (Nacalai Tesque) and diluted with saline and adjusted to 0.05, 0.25, or 1.25 mg/kg/hour. The prepared solution was used after injection into an ALZET® Osmotic Pump MODEL 2ML1 (9.68 µL/hour; DURECT).

An osmotic pump injected with tandospirone or solvent was implanted under the skin of rats in each group with n=6. After 4 hours, a levodopa containing solution was administered to observe and evaluate the behavior. After the observation and evaluation of behavior, blood was collected from rats in the tandospirone administration group to analyze the plasma tandospirone concentration.

The results in the drawings are indicated in terms of mean value±standard error. The test results were statistically analyzed by comparison with the solvent administration group by Steel test using the total AIMs score in 3 hours and the total AIMs score in 100 to 180 minutes as parameters. * indicates p<0.05, meaning that there is a significant difference.

(Results)

Figure 4:
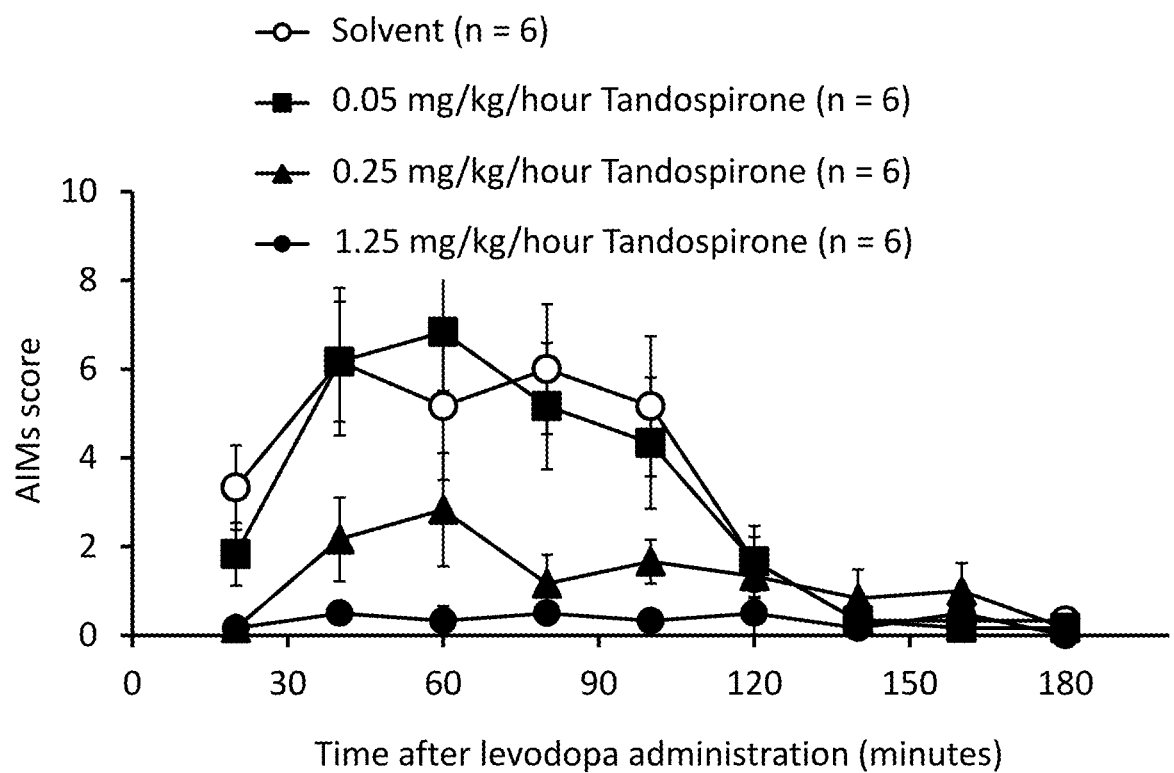
FIG. 4 is a diagram showing results of evaluating dyskinesia symptoms upon continuous subcutaneous infusion of tandospirone to a PD-LID rat model. Specifically, tandospirone was subcutaneously and sustainably administered to a PD-LID rat model, and levodopa was administered 4 hours later to evaluate the dyskinesia-like symptoms. The results are indicated in terms of mean value±standard error. * indicates p<0.05, meaning that there is a significant difference compared to the solvent administration group (Steel test). In the figure, graph A shows changes in the AIMs score over time after levodopa administration. Graph B shows the total AIMs score in 180 minutes. Graph C shows the total AIMs score in 100 to 180 minutes.
Figure 4:
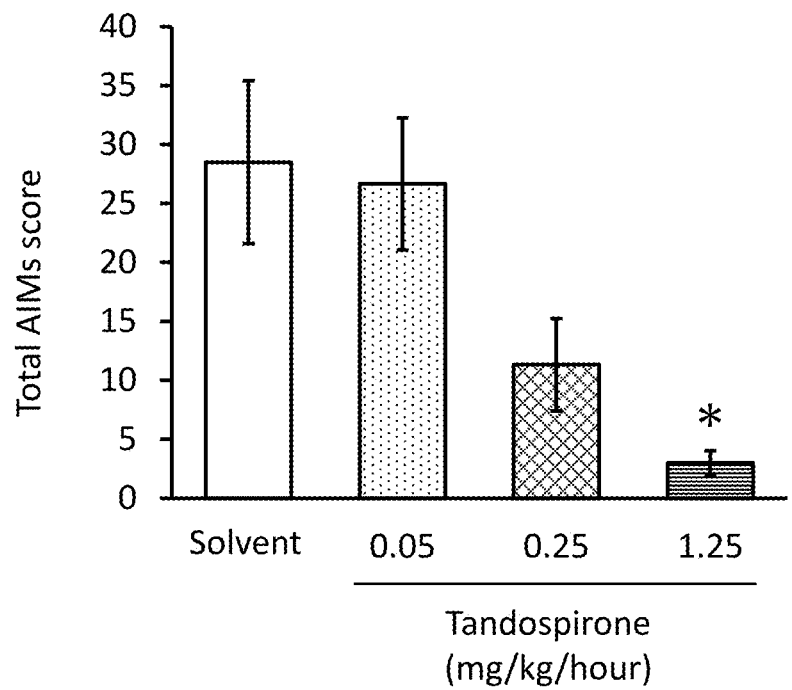
Figure 4:
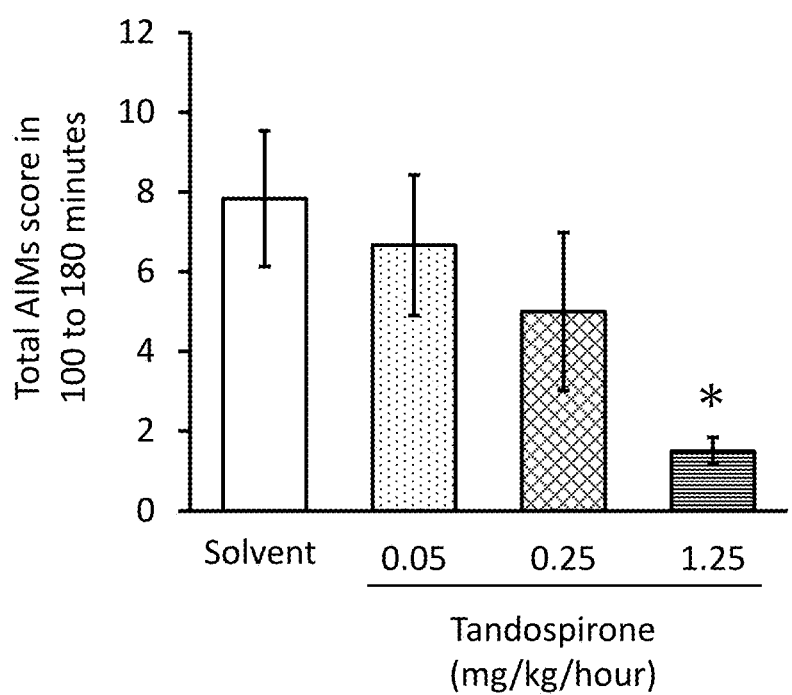

Continuous subcutaneous infusion of tandospirone dose-dependently improved dyskinesia-like symptoms, and significant improvement was observed at 1.25 mg/kg/hour (FIG. 4, Graphs A and B). A clear dyskinesia-like symptom (mean AIMs score of 2 or greater) was not found in both the solvent administration group and the tandospirone administration group at 120 to 140 minutes after levodopa administration. Furthermore, the total AIMs score dose-dependently decreased by continuous subcutaneous infusion of tandospirone, and a significant improvement was observed at 1.25 mg/kg/hour in the total AIMs score in 100 to 180 minutes (FIG. 4, Graph C). The mean value of plasma tandospirone concentration measured after the completion of the observation and evaluation of behavior was 23.5 ng/mL at 0.05 mg/kg/hour, 119 ng/mL at 0.25 mg/kg/hour, and 541 ng/mL at 1.25 mg/kg/hour.

In view of the results, continuous subcutaneous infusion of tandospirone dose-dependently improved dyskinesia-like symptoms. The administration did not lead to a rebound symptom at any of the dosages.

Example 4: Evaluation of Long-Term Dyskinesia Improving Effect of Continuous Subcutaneous Infusion of Tandospirone The sustainability of efficacy of tandospirone on dyskinesia-like symptoms was evaluated by continuous subcutaneous infusion of tandospirone to PD-LID rat model over 2 weeks.

(Testing Method)

A levodopa containing solution was repeatedly administered to 6-OHDA-lesioned rats for 3 weeks or more to observe and evaluate the behavior in the same manner as Example 2. Individuals with a total AIMs score of less than 15 were excluded from the test as not manifesting a dyskinesia-like symptom. The behavior was observed and evaluated before the drug evaluation date. The rats were assigned to each dosing group by using the 3 hour AIMs score, Locomotive behavior score, and rat body weight as indicators, which were used for evaluation of drugs.

Tandospirone citrate was dissolved into 1 M hydrochloric acid (Nacalai Tesque) and diluted with saline and adjusted to a concentration of 60 mg/mL (concentration of citrate). The prepared solution was used after injection into an ALZET® Osmotic Pump MODEL 2ML2 (4.53 µL/hour; DURECT) for releasing a drug solution at a stable rate for 2 weeks.

An osmotic pump injected with tandospirone citrate or solvent was implanted under the skin of rats in each group with n=8. After 4 hours, a levodopa containing solution was administered to observe and evaluate the behavior (day 0 of implanting the pump). Repeat administration of once daily levodopa containing solution was continued thereafter. The behavior was also observed and evaluated on day 13 of implanting the pump. After each observation and evaluation of behavior, blood was collected from half of the rats (n=4) in the tandospirone administration group to analyze the plasma tandospirone concentration.

The results in the drawings are indicated in terms of mean value±standard error of the total AIMs scores in 3 hours. The test results were statistically analyzed using Wilcoxon rank sum test using the total AIMs score as a parameter. ** indicates p<0.01, meaning that there is a significant difference compared to the solvent administration group.

(Results)

Figure 5:
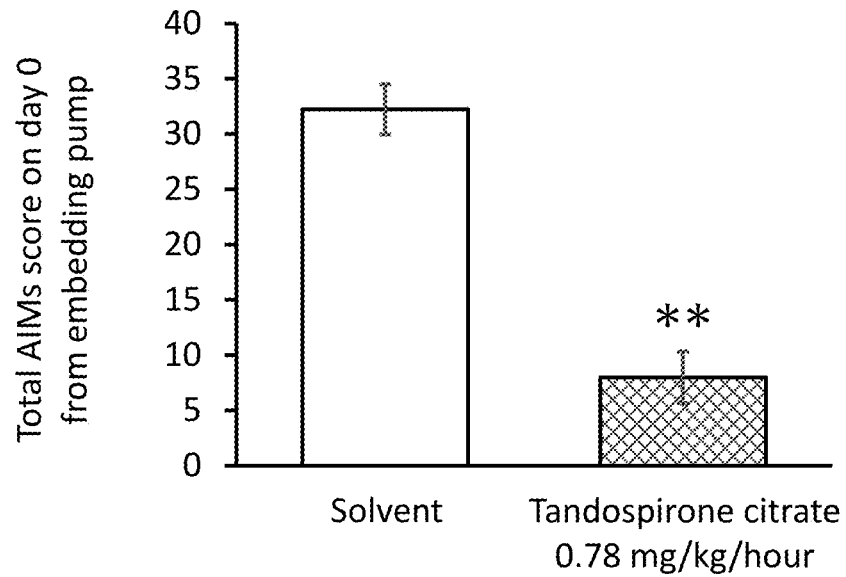
FIG. 5 is a diagram showing results of long term evaluation of dyskinesia-like symptoms upon continuous subcutaneous infusion of tandospirone citrate to a PD-LID rat model. Specifically, tandospirone citrate was subcutaneously and sustainably administered to a PD-LID rat model, and dyskinesia-like symptoms were evaluated on the day of starting the administration and on day 13 of administration. The total AIMs score in 180 minutes is indicated in terms of mean value±standard error. ** indicates p<0.01, meaning that there is a significant difference compared to a solvent administration group (Wilcoxon rank sum test). In the figure, Graph A shows results on day 0 of implanting a pump. Graph B shows results on day 13 of implanting a pump.
Figure 5:
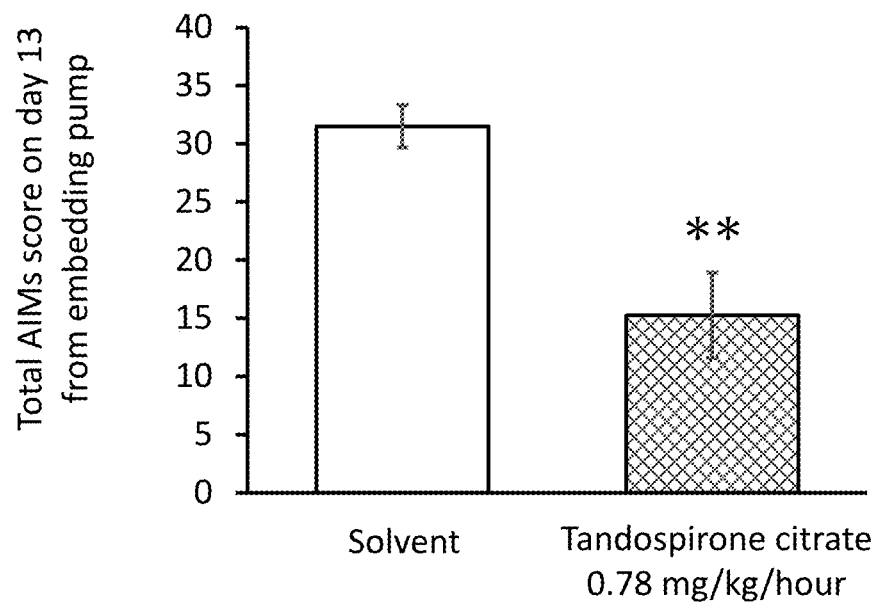

Significant improvement in dyskinesia-like symptoms was observed compared to the solvent group on day 0 of implanting the pump from continuous subcutaneous infusion of tandospirone citrate (60 mg/mL: mean 0.78 mg/kg/hour as tandospirone citrate) (FIG. 5, Graph A). The mean value of the plasma tandospirone concentrations (value converted in terms of free form) measured after the completion of observation and evaluation of behavior was 281 ng/mL. A significant improvement in dyskinesia-like symptoms relative to the solvent group was also observed on day 13 of implanting the pump (FIG. 5, Graph B). The mean value of the plasma tandospirone concentrations (value converted in terms of free form) measured after the completion of observation and evaluation of behavior was 143 ng/mL.

In view of the results, the effect of improving PD-LID symptoms was sustained even after continuous subcutaneous infusion of tandospirone for 13 days.

Example 5: Evaluation of the Effect of Continuous Subcutaneous Infusion of Tandospirone on Prevention/Delay of the Manifestation of Dyskinesia Dyskinesia-like abnormal involuntary movement is manifested when levodopa is repeatedly administered to 6-OHDA-lesioned rats. In this regard, the effect of tandospirone on preventing the manifestation of dyskinesia-like symptoms was evaluated by subcutaneous sustained administration of tandospirone from immediately after starting the repeated administration of levodopa.

(Testing Method)

Tandospirone citrate was dissolved into 1 M hydrochloric acid (Nacalai Tesque) and diluted with saline and adjusted to a concentration of 60 mg/mL or 30 mg/mL. The prepared solution was used after injection into an ALZET® Osmotic Pump MODEL 2ML2 (4.53 µL/hour; DURECT).

6-OHDA-lesioned rats were assigned to each administration group using the number of apomorphine hydrochloride hemihydrate induced rotations and body weight as indicators. An osmotic pump injected with tandospirone citrate or solvent was implanted under the skin of rats on the day after starting repeated administration of a levodopa containing solution with the same composition as Example 2. The behavior was observed and evaluated using the same method as Example 2 on day 3, 5, 9, and 15 after starting the repeated administration of levodopa. The osmotic pump implanted subcutaneously was retrieved after the observation and evaluation of behavior on day 15. The behavior was also observed and evaluated on the following day (day 16 of repeated administration of levodopa).

The results in the drawings are indicated in terms of mean value±standard error of the total AIMs scores in 3 hours. The test results were statistically analyzed by comparison with the solvent administration group using Steel test with the total AIMs score on day 16 of repeated levodopa administration as the parameter. * indicates p<0.05 and ** indicates p<0.01, meaning that there is a significant difference compared to the solvent administration group.

(Results)

Figure 6:
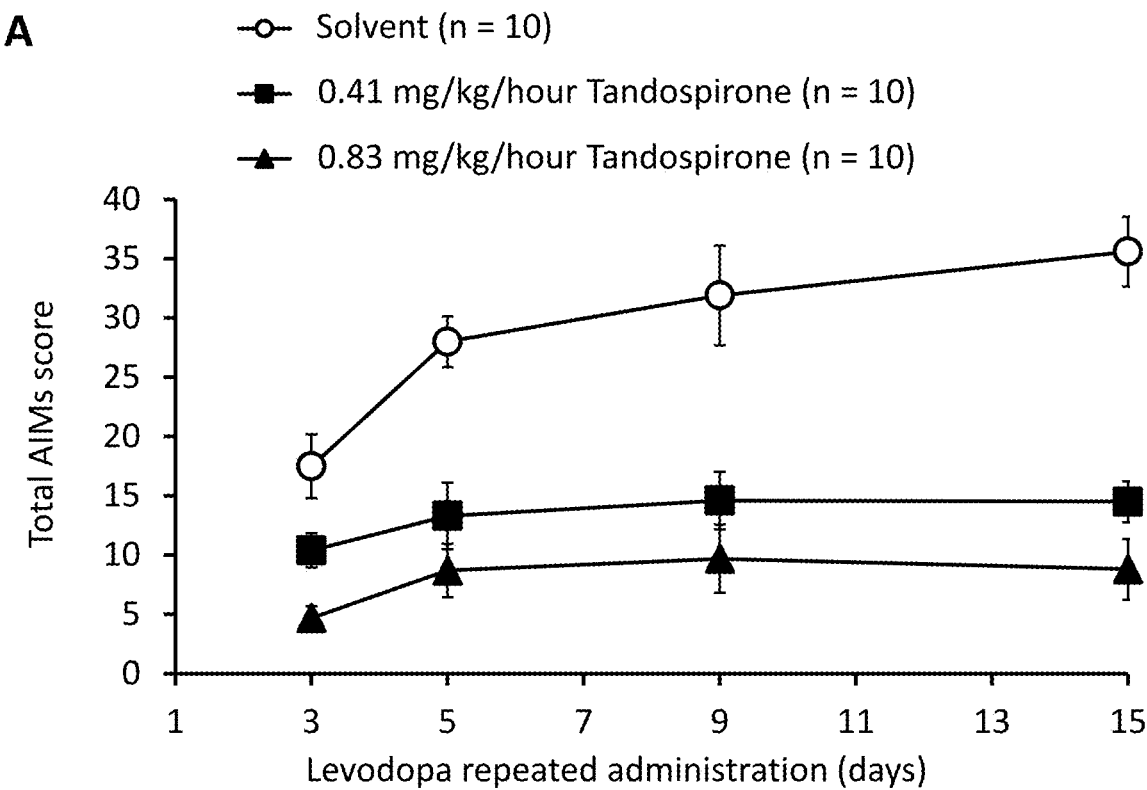
FIG. 6 is a diagram showing the effect of continuous subcutaneous infusion of tandospirone citrate to rats treated on one side of the brain with 6-hydroxydopamine on dyskinesia development. Specifically, levodopa was repeatedly administered and tandospirone citrate was subcutaneously and sustainably administered to rats treated on one side of the brain with 6-hydroxydopamine to evaluate the effect on levodopa repeated administration induced dyskinesia-like symptom manifestation. The results are indicated in terms of mean value±standard error. * indicates p<0.05, and ** indicates p<0.01, meaning that there is a significant difference compared to the solvent administration group (Steel test). In the figure, graph A shows the results of levodopa repeated administration over time, and graph B shows results on the day after the completion of tandospirone citrate administration (day 16).
Figure 6:
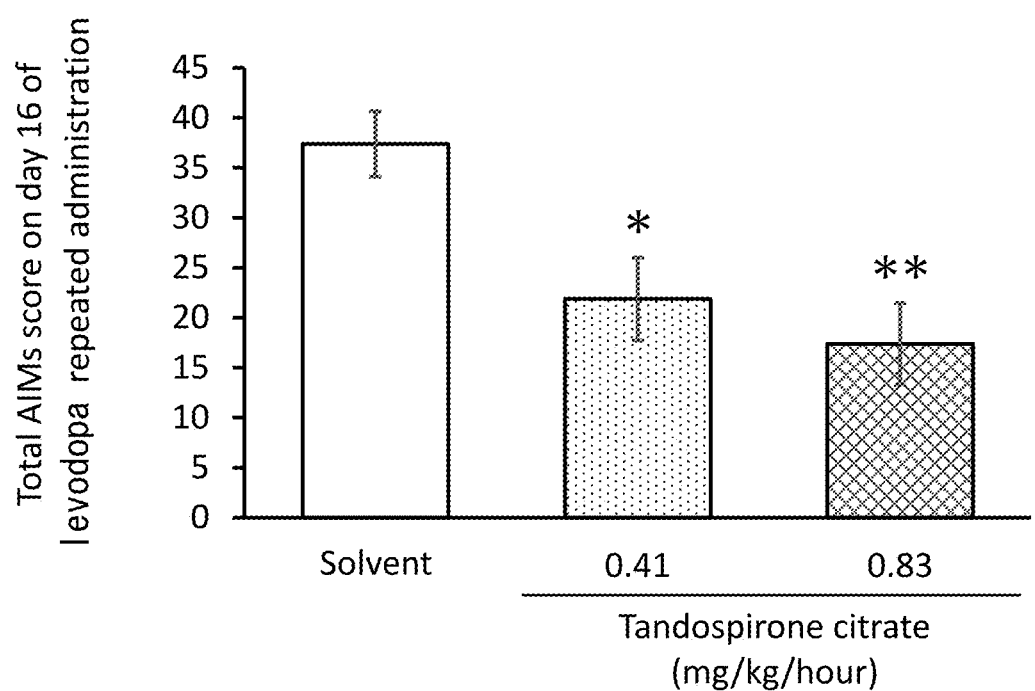
Figure 7:
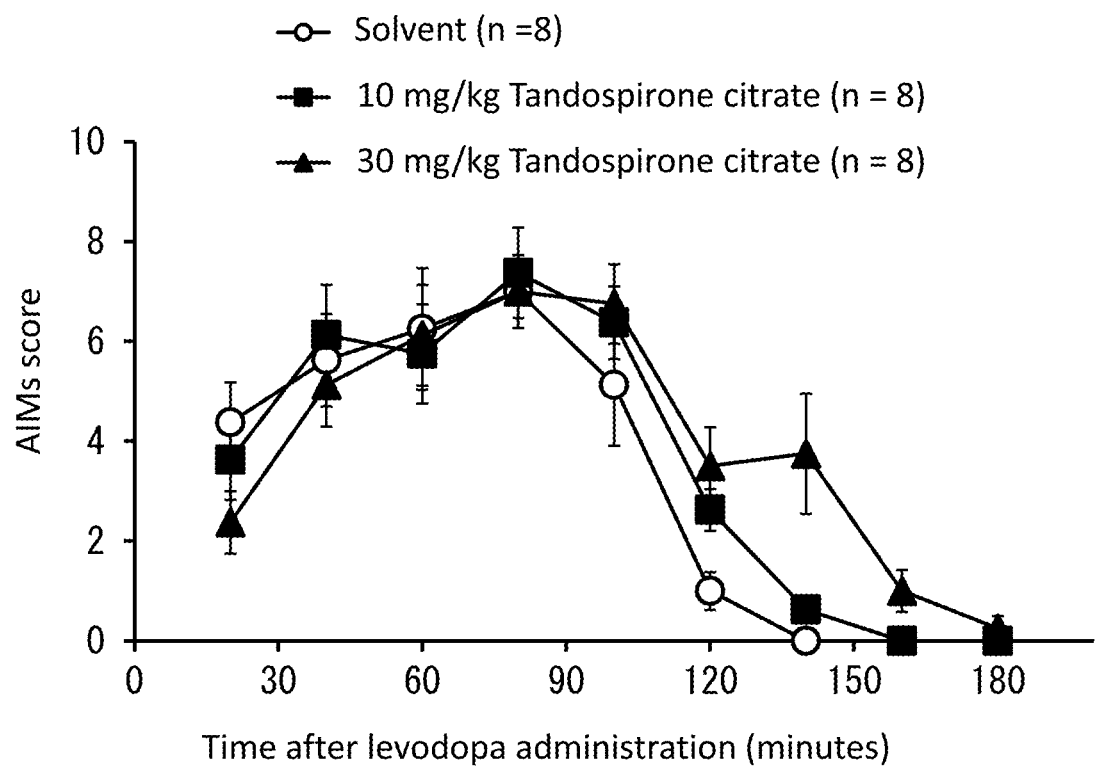
FIG. 7 is a diagram showing results of evaluating dyskinesia-like symptoms when tandospirone citrate was orally administered to a PD-LID rat model. Specifically, tandospirone citrate (10 mg/kg, 30 mg/kg as citrate concentration) was orally administered to a PD-LID rat model, and levodopa was administered 5 minutes later to evaluate dyskinesia-like symptoms. The results are indicated in terms of mean value±standard error. * indicates p<0.05, meaning that there is a significant difference compared to a solvent administration group (Steel test). In the figure, graph A shows changes in AIMs score over time after levodopa administration. Graph B shows the total AIMs score in 180 minutes. Graph C shows the total AIMs score in 100 to 180 minutes.
Figure 7:
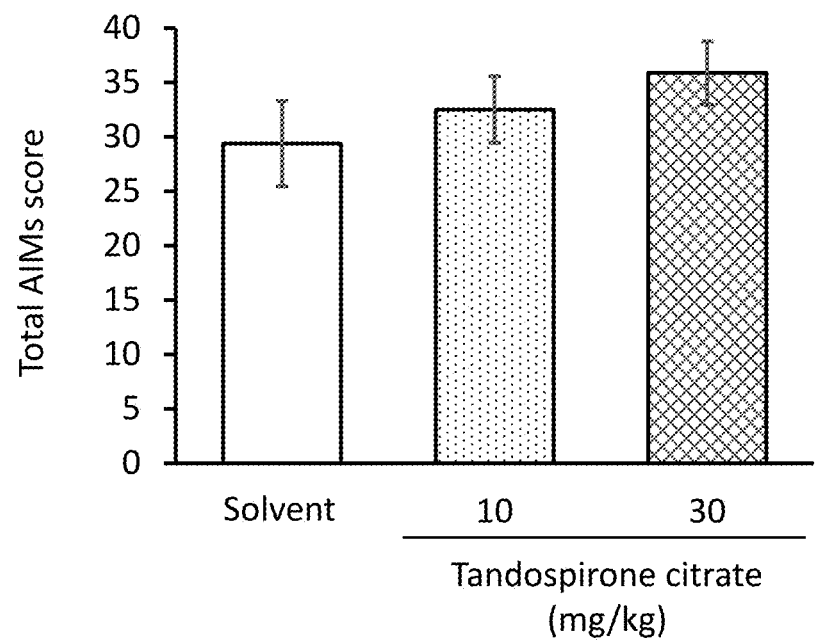
Figure 7:
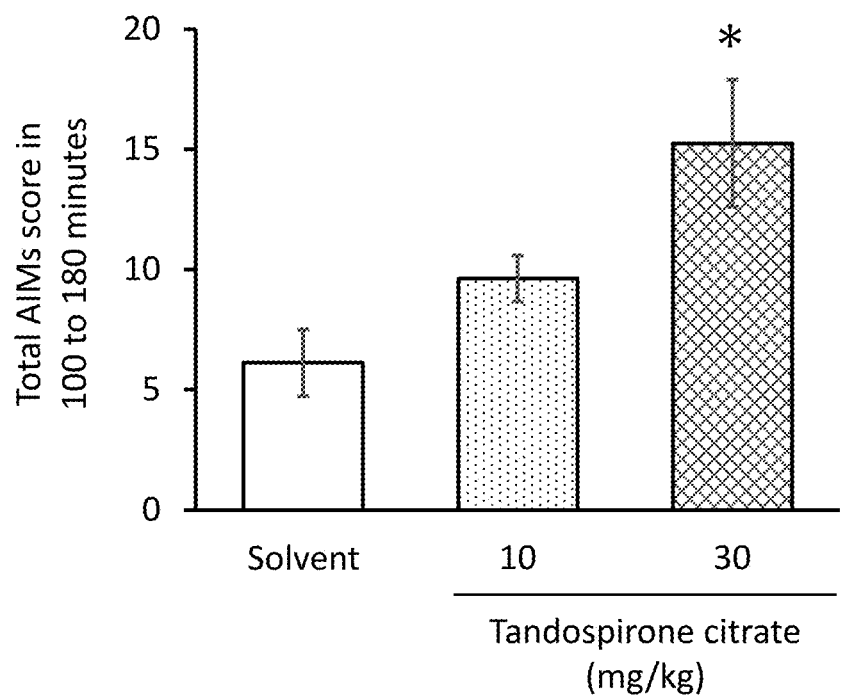
Figure 8B:
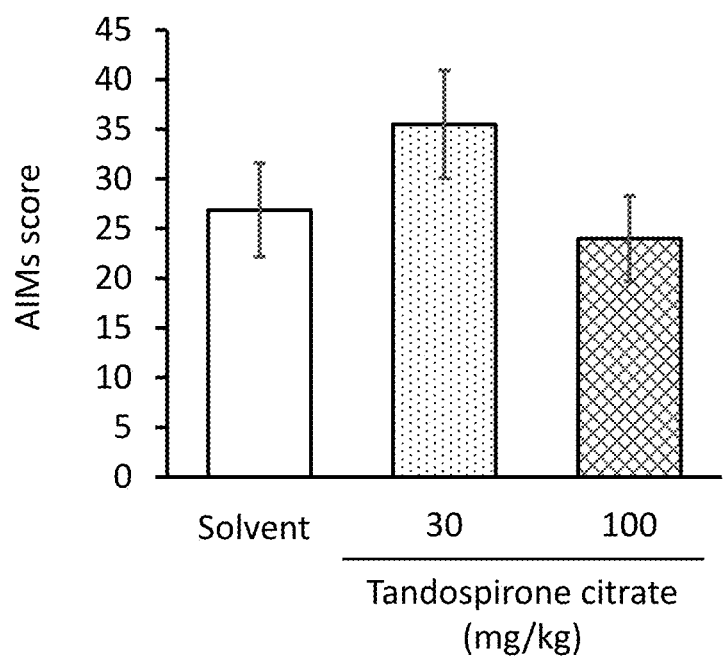
Figure 8C:
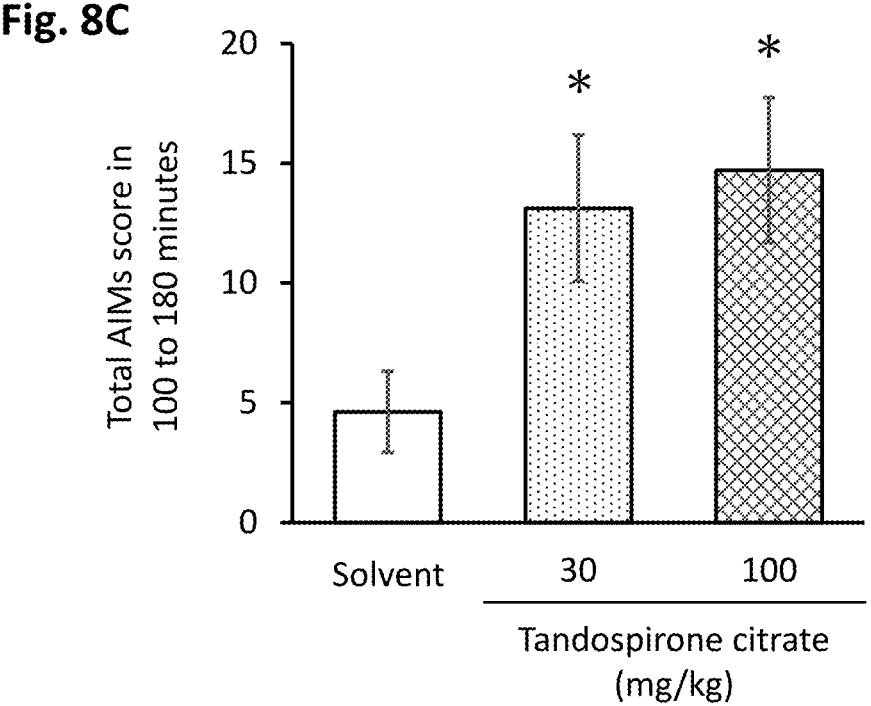
Figure 8D:
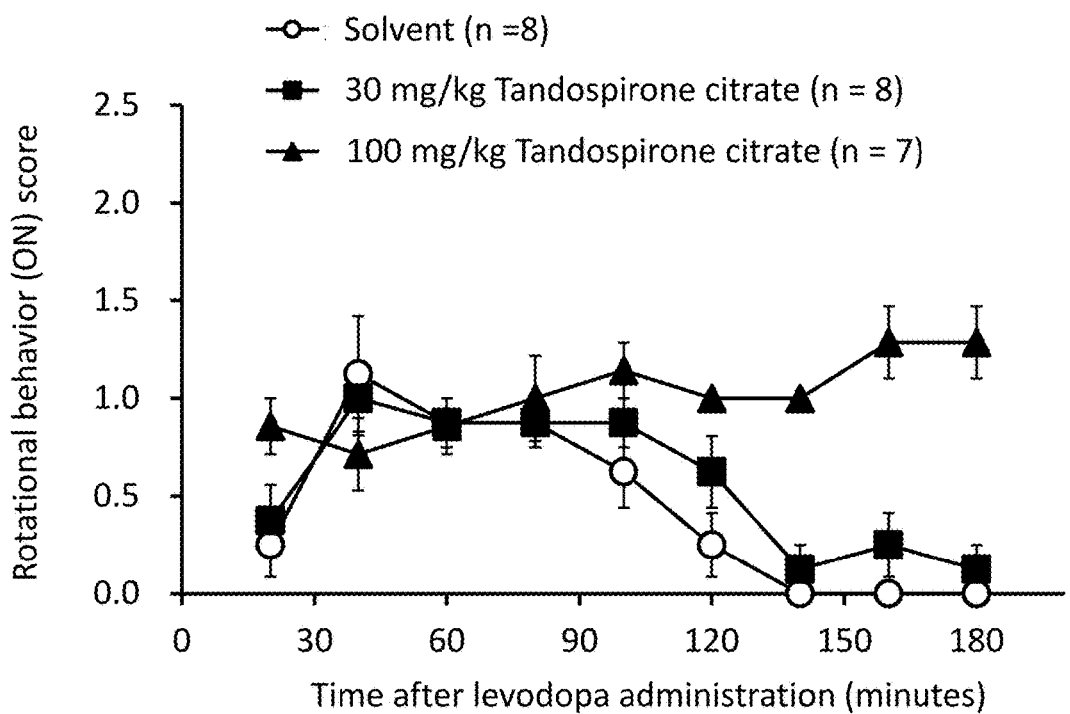
FIGS. 8D, 8E, and 8F show results of measuring dyskinesia-like symptoms and rotational behavior (ON score) for 180 minutes every 20 minutes by administering levodopa to PD-LID rat models by oral administration of tandospirone. Behavior was observed and evaluated from 20 minutes after intraperitoneal administration of levodopa to 3 hours after administration within a transparent acrylic cage for 1 minute every 20 minutes. Observation of behavior was classified into Limb AIMs (involuntary bending or stretching of front limbs on the opposite side of the disorder, opening/closing of hands, up and down movement of the wrist, chorea-like tremor, dystonia-like stiffening), Axial AIMs (twisting of the upper body/neck to the opposite side of the disorder, losing balance and falling, or maintaining an unstable posture), Orolingual AIMs (trembling of the jaw or violently sticking out the tongue forward), and Locomotive behavior (rotational behavior to the other side of the destruction), and was given a score from 0 to 4 (0: none, 1: less than 30 seconds of manifestation, 2: 30 seconds or more of manifestation, 3: constantly, but stop with a stimulus such as sound, and 4: constant manifestation, which does not stop with a stimulus such as sound). The sum of the scores for Limb AIMs, Axial AIMs, and Orolingual AIMs in 3 hours was used as the total dyskinesia-like symptom (AIMs) score. Tandospirone citrate (30 mg/kg, 100 mg/kg as citrate concentration) was orally administered to a PD-LID rat model, and levodopa was administered 5 minutes later to evaluate the scores for dyskinesia-like symptoms (see FIG. 8A, supra) and rotational behavior (FIG. 8D). The results are indicated in terms of mean value±standard error. From oral administration of tandospirone citrate (100 mg/kg), an increase in the total ON score was observed (FIG. 8E), and a significant prolongation in the ON-time without dyskinesia for 180 minutes (Locomotive behavior ≥1, and AIMs score=0) was observed (FIG. 8F).
Figure 8E:
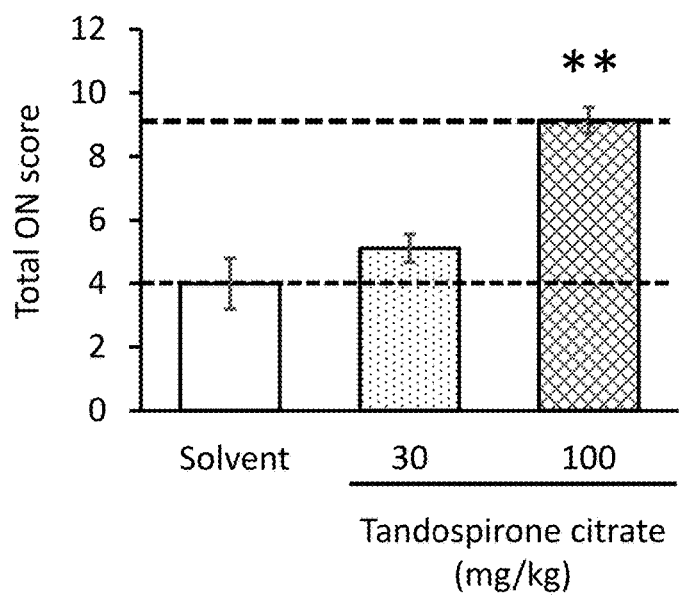
Figure 8F:
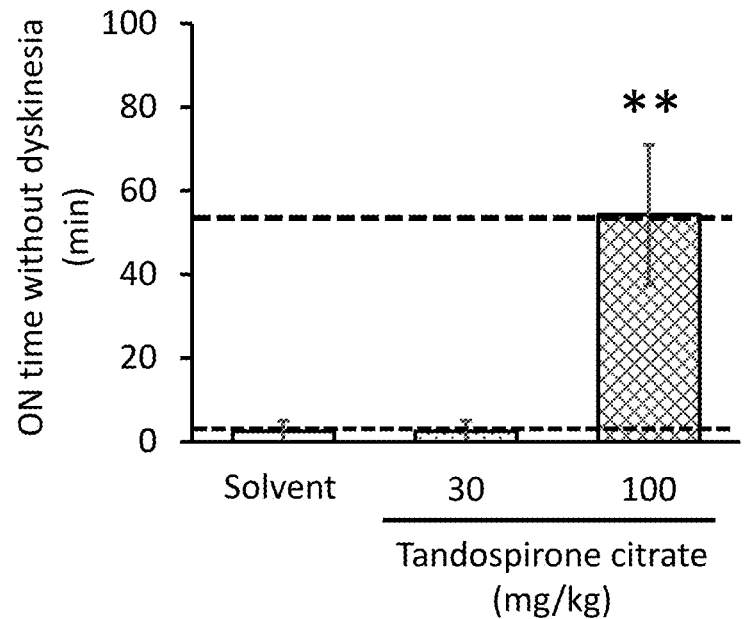
Figure 8G:
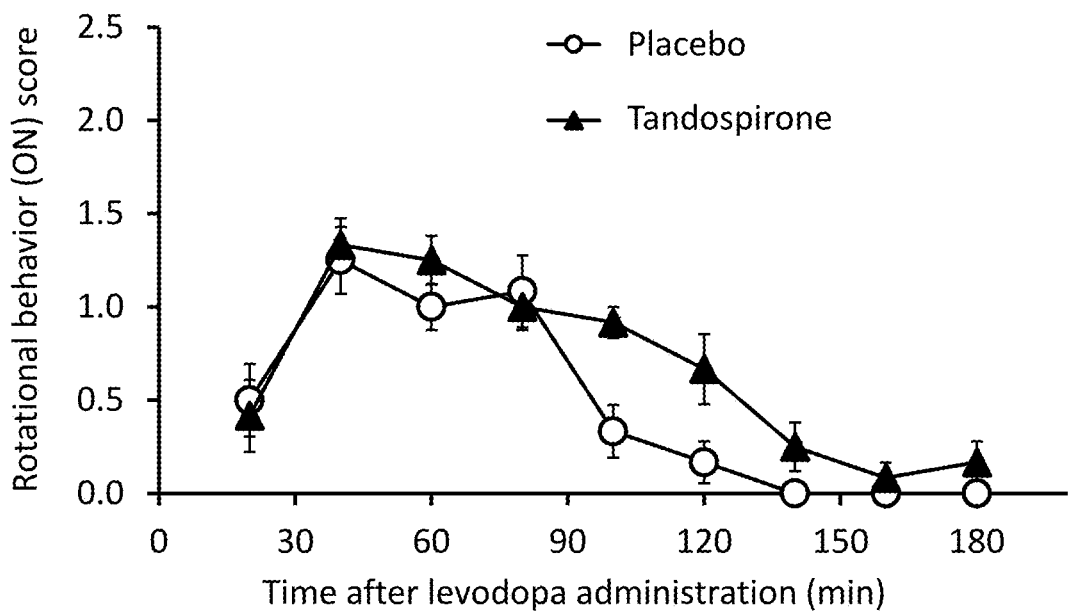
FIGS. 8G, 8H, and 8I show results of measuring dyskinesia-like symptoms and rotational behavior (ON score) for 180 minutes every 20 minutes by administering levodopa to PD-LID rat models by transdermal administration (no stripping) of tandospirone. Specifically, a tandospirone tape agent was transdermally administered to a PD-LID rat model and levodopa was administered 4 hours later to evaluate dyskinesia-like symptoms (see FIG. 2A, supra) and rotational behavior (FIG. 8G). The results are indicated in terms of mean value±standard error. From application of a tandospirone tape agent, an increase in the total ON score was observed (FIG. 8H), and a significant prolongation in the ON-time without dyskinesia for 180 minutes (Locomotive behavior ≥1, and AIMs score=0) was observed (FIG. 8I).
Figure 8H:
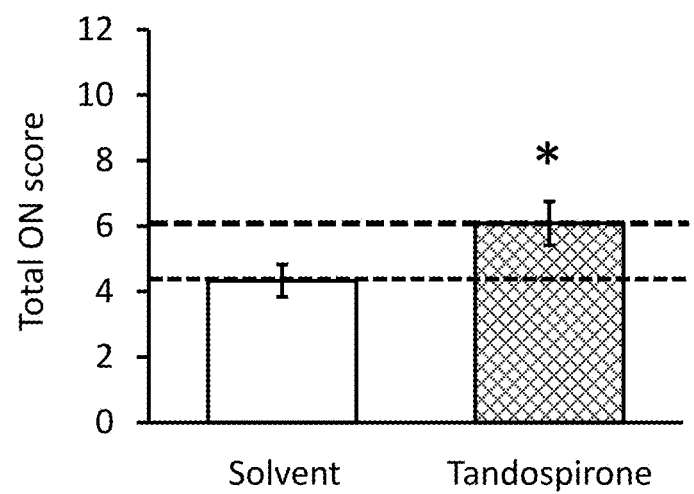
Figure 8I:
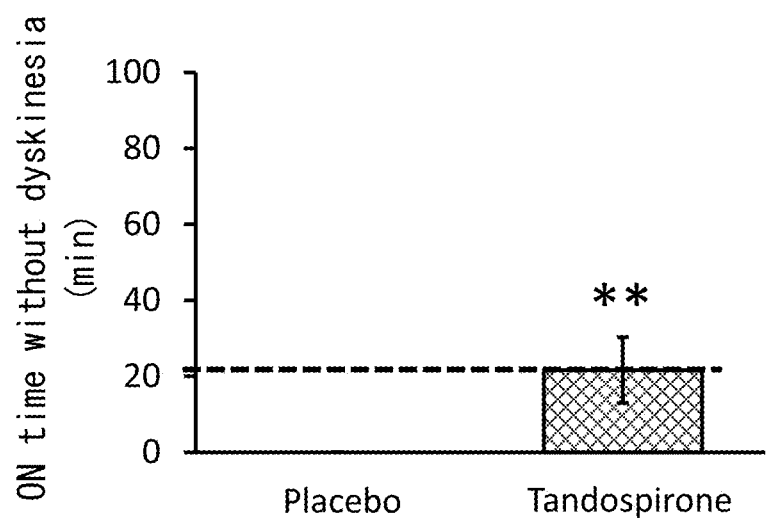
Figure 8J:
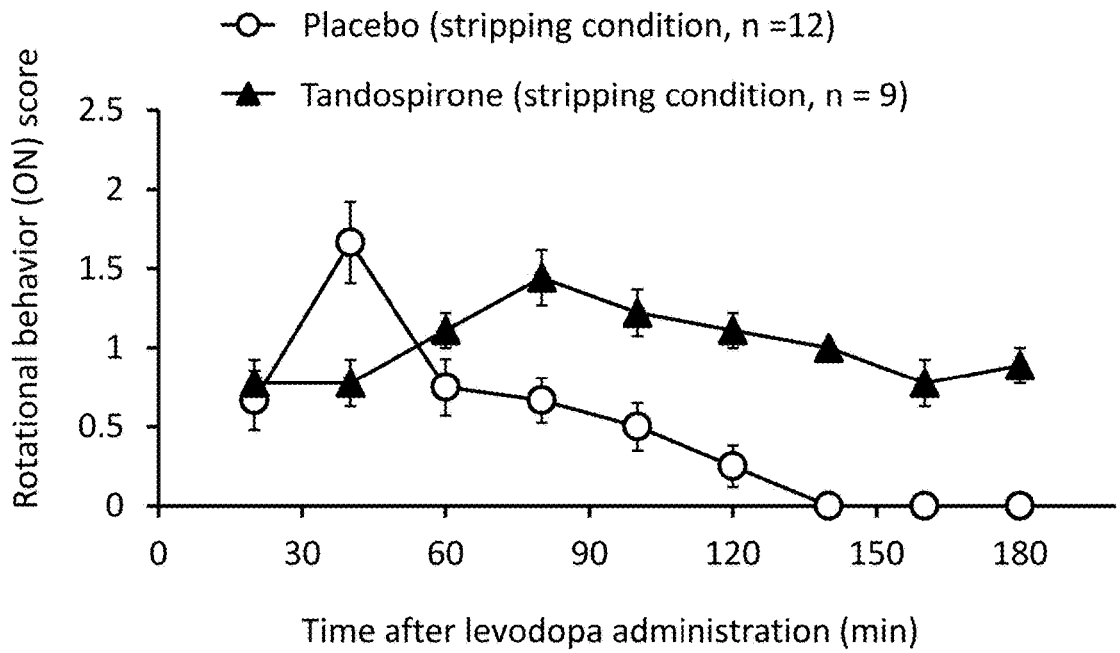
FIGS. 8J, 8K, and 8L show results of measuring dyskinesia-like symptoms and rotational behavior (ON score) for 180 minutes every 20 minutes by administering levodopa to PD-LID rat models by transdermal administration (with stripping condition) of tandospirone. Specifically, a tandospirone tape agent was transdermally administered to a PD-LID rat model on which stratum corneum stripping was performed on the tape agent application site, and levodopa was administered 4 hours later to evaluate dyskinesia-like symptoms (see FIG. 3, Graph A) and rotational behavior (FIG. 8J). The results are indicated in terms of mean value±standard error. From application of a tandospirone tape agent after stratum corneum stripping, an increase in the total ON score was observed (FIG. 8K), and a significant prolongation in the ON-time without dyskinesia for 180 minutes (Locomotive behavior ≥1, and AIMs score=0) was observed (FIG. 8L).
Figure 8K:
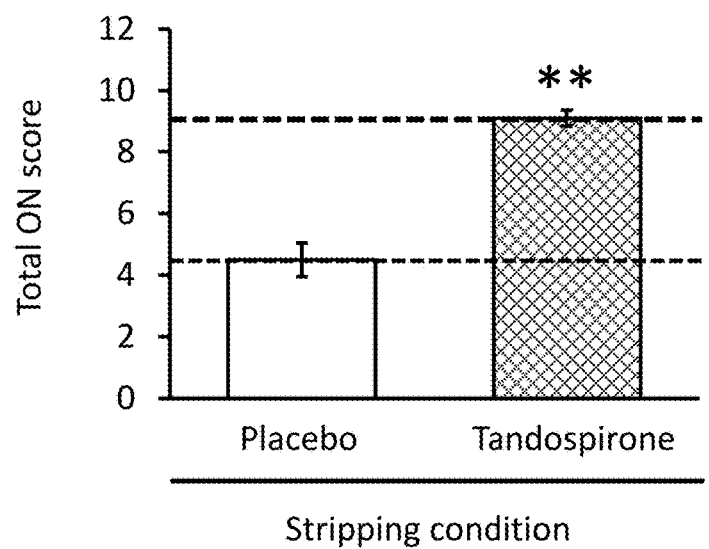
Figure 8L:
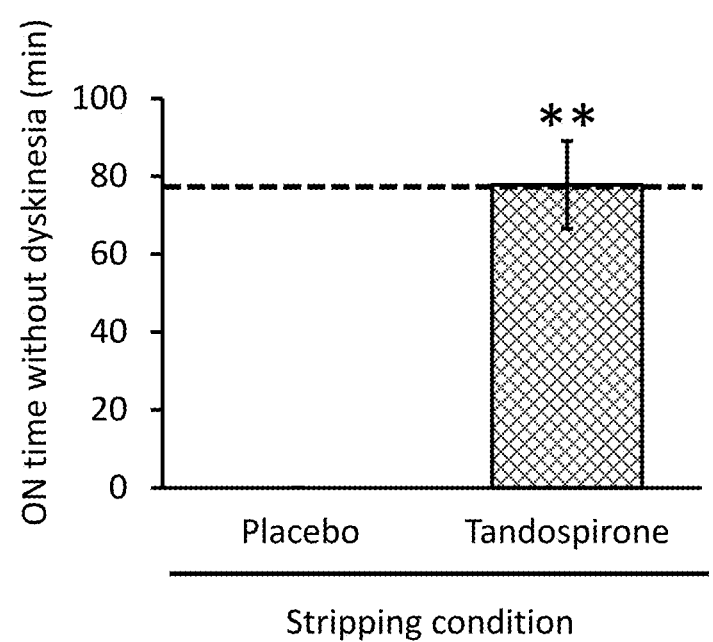
Figure 9:
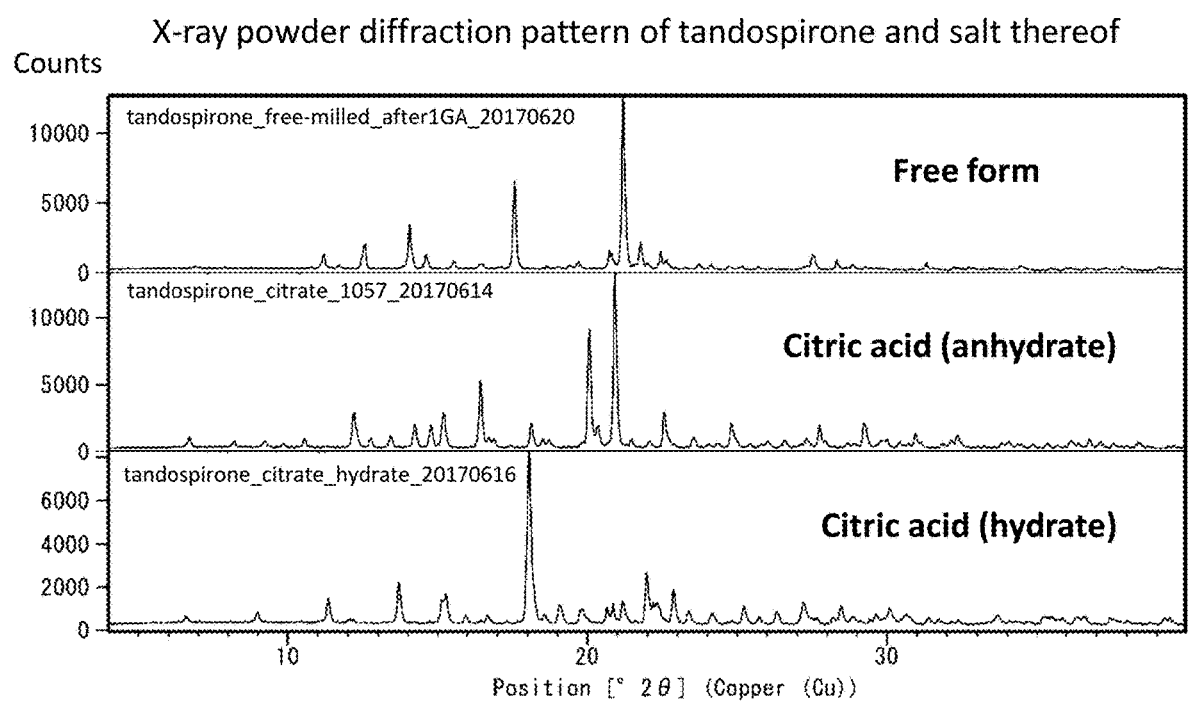
FIG. 9 is a diagram showing X-ray powder diffraction patterns of tandospirone free form, tandospirone citrate (hydrate), and tandospirone citrate (anhydrate).

Continuous subcutaneous infusion of tandospirone citrate (30 mg/mL: mean of 0.41 mg/kg/hour or 60 mg/mL: mean of 0.83 mg/kg/hour) suppressed the increase in total AIMs score associated with repeated administration of levodopa compared to the solvent group (FIG. 6, Graph A). The total AIMs score was significantly lower in the group administered with tandospirone citrate compared to the solvent group on the day after the completion of tandospirone citrate administration (FIG. 6, Graph B).

In view of the results, continuous subcutaneous infusion of tandospirone prevented onset of PD-LID, and the effect thereof was also sustained to the day after the final dose of tandospirone.

Comparative Example 1: Evaluation of Oral Administration of Tandospirone on Dyskinesia Symptoms (Testing Method)

The behavior was observed and evaluated using the same method as Example 2. Tandospirone citrate was suspended in 0.5% methylcellulose solution and orally administered to rats. After 5 minutes, a levodopa containing solution was intraperitoneally administered, and the behavior was observed and evaluated. The results in the drawings are indicated in terms of mean value±standard error. The test results were statistically analyzed by comparison with the solvent administration group by Steel test using the total AIMs score in 3 hours and total AIMs score in 100 to 180 minutes as parameters. * indicates p<0.05, meaning that there is a significant difference.

(Results)

(1) Dyskinesia-Like Symptom

In the tandospirone citrate (10, 30, or 100 mg/kg as citrate concentration) orally administered groups, a significant change in the total AIMs score was not observed in comparison to the solvent administration group (FIGS. 7A, 7B, 7C, 8A and 8B). The results suggest that the PD-LID cannot be improved with a tandospirone oral administration formulation.

At 120 to 140 minutes after levodopa administration, dyskinesia-like symptoms subsided in the solvent administration group, but a clear dyskinesia-like symptom (mean AIMs score of 2 or greater) was observed in the tandospirone citrate oral administration group (30 or 100 mg/kg). Furthermore, when the solvent administration group and tandospirone citrate oral administration group were compared using the total AIMs score in 100 to 180 minutes as the indicator, a significant increase in the total AIMs score was observed in the tandospirone citrate oral administration group (30 or 100 mg/kg) in comparison to the solvent administration group (FIGS. 7A, 7B, 7C and 8C). The result suggests the potential of manifestation of a phenomenon with delayed manifestation and exacerbation of dyskinesia-like symptoms (rebound symptom of dyskinesia) in a formulation for oral administration of tandospirone.

In view of the above, an improvement in dyskinesia symptoms was not observed in PD-LID rat models in the tandospirone oral administration group (Table 3-(i)). A rebound symptom of dyskinesia was observed in high dosage oral administration group (Table 3-(ii)). In view of the results, oral administration of tandospirone has an insufficient effect of improving dyskinesia, and has a risk of manifestation of a rebound symptom. Therefore, combined therapy with a levodopa formulation is possibly unsuitable.

TABLE 3

Comparison of dyskinesia-like symptom scores
for transdermal and oral administration

| | Dosage (mg/kg) Condition | (i) Indicator of degree of improvement in dyskinesia symptom | (ii) Indicator of rebound symptom of dyskinesia |
|---|---|---|---|
| Transdermal administration (Condition 1) (Example 2) | 37 (No stripping) | Improvement 17.7** | No effect −0.1 |
| Transdermal administration (Condition 2) (Example 2) | 45 (With stripping) | Improvement 27.1** | No effect 0.9 |
| Oral administration (Comparative Example 1) | 6.7 | No improvement −3.1 | Exacerbating trend −3.5 |
| Oral administration (Comparative Example 1) | 20 | No improvement −6.5(FIGS. 7A-7C) −8.6(FIGS. 8A-8L) | Exacerbation −9.1*(FIGS. 7A-7C) −8.5*(FIGS. 8A-8L) |
| Oral administration (Comparative Example 1) | 67 | No improvement 2.9 | Exacerbation −10.1* |

The dosage was described as a numerical value converted in terms of tandospirone free form. The difference in total AIMs score in three hours (#1) is used as an indicator of a degree of improvement in dyskinesia symptoms, and the difference in total AIMs score in 100 to 180 minutes (#2) is used as an indicator of a rebound symptom of dyskinesia.

Difference in total AIMs score in 3 hours=(total
  AIMs score for placebo tape agent or solvent
  administration group)−(total AIMs score for
  tandospirone administration group)         (#1)

Difference in total AIMs score in 100 to 180 min-
  utes=(total AIMs score in 100 to 180 minutes
  for placebo tape agent or solvent administration
  group)−(total AIMs score in 100 to 180 minutes
  for tandospirone administration group)     (#2)

**: there is a significant difference (p<0.01), *: there is a significant difference (p<0.05)

As shown in Table 3, a significant difference in improvement of levodopa induced dyskinesia symptoms was not found with oral administration, but a significant improvement thereof was found with transdermal administration.

Oral administration was also newly found to have a rebound symptom of dyskinesia, so that therapy by oral administration of tandospirone was found to be undesirable. Meanwhile, a rebound symptom of dyskinesia was not observed for transdermal administration.

In view of the above, the therapeutic effect of tandospirone oral administration on levodopa induced dyskinesia symptoms is limited, suggesting that tandospirone transdermal administration is preferable.

Example 5-2: Evaluation of ON-Time Prolongation Action in PD-LID Animal Model

This Example evaluated tandospirone's antiparkinsonian action time, i.e., ON-time, of levodopa in PD-LID animal models.

(Test Method)

To make a PD-LID rat model, a mixture of levodopa methyl ester hydrochloride (6 mg/kg; Sigma-Aldrich) dissolved in saline and benserazide hydrochloride (15 mg/kg; Sigma-Aldrich) (hereinafter, also referred to as "levodopa containing solution") was intraperitoneally administered once daily to 6-OHDA-lesioned rats. The levodopa containing solution was repeatedly administered for 3 weeks or longer to observe and evaluate the behavior. The behavior was observed and evaluated in a transparent acrylic cage for 1 minute every 20 minutes after 20 minutes from the intraperitoneal administration of the levodopa containing solution, up until after 3 hours from administration. Observation of behavior was classified into Limb AIMs (involuntary bending or stretching of front limbs on the opposite side of the disorder, opening/closing of hands, up and down movement of the wrist, chorea-like tremor, dystonia-like stiffening), Axial AIMs (twisting of the upper body/neck to the opposite side of the disorder, losing balance and falling, or maintaining an unstable posture), Orolingual AIMs (trembling of the jaw or violently sticking out the tongue forward), and Locomotive behavior (rotational behavior to the other side of the destruction), and was given a score from 0 to 4 (0: none, 1: less than 30 seconds of manifestation, 2: 30 seconds or more of manifestation, 3: constantly, but stopped with a stimulus such as sound, and 4: constant manifestation, which does not stop with a stimulus such as sound). The sum of the scores for Limb AIMs, Axial AIMs, and Orolingual AIMs in 3 hours was used as the total dyskinesia-like symptom (AIMs) score. Individuals with a total AIMs score of less than 10 were excluded from the test as not manifesting a dyskinesia-like symptom. The behavior was observed and evaluated before the drug evaluation date. The rats were assigned to each dosing group by using the 3 hour total dyskinesia-like symptom (AIMs) score, Locomotive behavior score, and rat body weight as indicators, which were used for evaluation of drugs.

For an indicator of dyskinesia behavior, the sum of the Limb AIMs, Axial AIMs, and Orolingual AIMs at each evaluation point was used as the AIMs score. For the rotational behavior (ON score), Locomotive behavior at each evaluation point was used as an indicator. The total ON score in 3 hours was used as the total ON score. For ON time without dyskinesia, the period during which the AIMs score is 0 and Locomotive behavior is 1 or greater at each evaluation point was added.

Duration of action of levodopa without a dyskinesia symptom (ON time without dyskinesia) refers to the aggregate time with no dyskinesia during the antiparkinsonian action effective time, i.e., "ON-time", and defined as the time during which the dyskinesia symptom (AIMs) score is 0 and the rotational behavior (Locomotive behavior) score is 1 or greater at each evaluation point after levodopa administration.

(Oral Administration)

Tandospirone citrate (30 mg/kg, 100 mg/kg as citrate concentration) was suspended in a 0.5% methylcellulose solution and orally administered to rats. After 5 minutes, a levodopa containing solution was intraperitoneally administered, and the behavior was observed and evaluated. The results in the drawings are indicated in terms of mean value±standard error. The test results were statistically analyzed by comparison with the solvent administration group using the Steel test with the total ON score in 3 hours or ON time without dyskinesia as an indicator. ** indicates p<0.01, meaning that there is a significant difference.

(Transdermal Administration)

For evaluation of a tape agent, the abdominal regions of the rats were shaved prior to the evaluation date. The tape agent was applied to the abdominal regions of the rats on the evaluation date at 60 cm$^2$/kg (including 6.5% W/V tandospirone free form). After 4 hours from application, a levodopa containing solution was intraperitoneally administered to observe and evaluate the behavior. The results in the drawings are indicated in terms of mean value±standard error. Individuals with 50% or more of the tape agent coming off during the test were excluded from analysis. The test results were statistically analyzed by comparison with the placebo tape administration group using Wilcoxon rank sum test with the total ON score in 3 hours or ON time without dyskinesia as an indicator. * indicates p<0.05 and ** indicates p<0.05, meaning that there is a significant difference compared to the solvent oral administration group or the placebo tape administration group.

(Transdermal Administration: Stripping Conditions)

When evaluating a tape agent under stratum corneum stripping conditions (tandospirone high exposure conditions), stripping was performed 10 times at the abdominal region of rats using a transpore surgical tape (3M) on the evaluation date, and a tape agent was then applied at 60 cm$^2$/kg (including 6.5% W/V tandospirone free form).

(Results)

An increase in the total ON score after 180 minutes of levodopa administration was observed (FIG. 8E) and an increase in ON time without dyskinesia for 180 minutes was observed (FIG. 8F) relative to the solvent administration group by oral administration of tandospirone citrate (30 mg/kg and 100 mg/kg). Prolongation of ON-time was observed at 180 minutes after levodopa administration (FIGS. 8H and K) and an increase in ON time without dyskinesia for 180 minutes was observed (FIGS. 8I and L) relative to the placebo tape administration group by applying a tandospirone tape agent (with/without stripping condition).

In view of the above results, tandospirone exhibited an action of prolonging ON-time in PD-LID rat models. In particular, ON time without dyskinesia increased from tandospirone transdermal administration, but prolongation of ON time without dyskinesia was observed only at a dose at which there is a risk of side effects (100 mg/kg) from oral administration. This suggests that oral administration cannot provide preferred therapy. It was rather unexpected that a therapeutic effect which is comparable to that from oral administration can be exerted with transdermal administration.

Comparative Example 2: Evaluation of Tandospirone Metabolite on Dyskinesia Symptom The effect of a tandospirone metabolite 1-(2-Pyrimidyl)piperazine (hereinafter, also referred to as "1-PP") on dyskinesia-like symptoms was evaluated.

(Testing Method)

The behavior was observed and evaluated using the same method in Example 2. 1-PP dihydrochloride (Tokyo Chemical Industry) was dissolved in saline and subcutaneously administered to rats. After 5 minutes, a levodopa containing solution was intraperitoneally administered to observe and evaluate the behavior. The results in the drawings are indicated in terms of mean value±standard error. The test results were statistically analyzed by comparison with the solvent administration group by Steel test by using the total AIMs score in 3 hours and total AIMs score in 100 to 180 minutes as parameters.

(Results)

Figure 10:
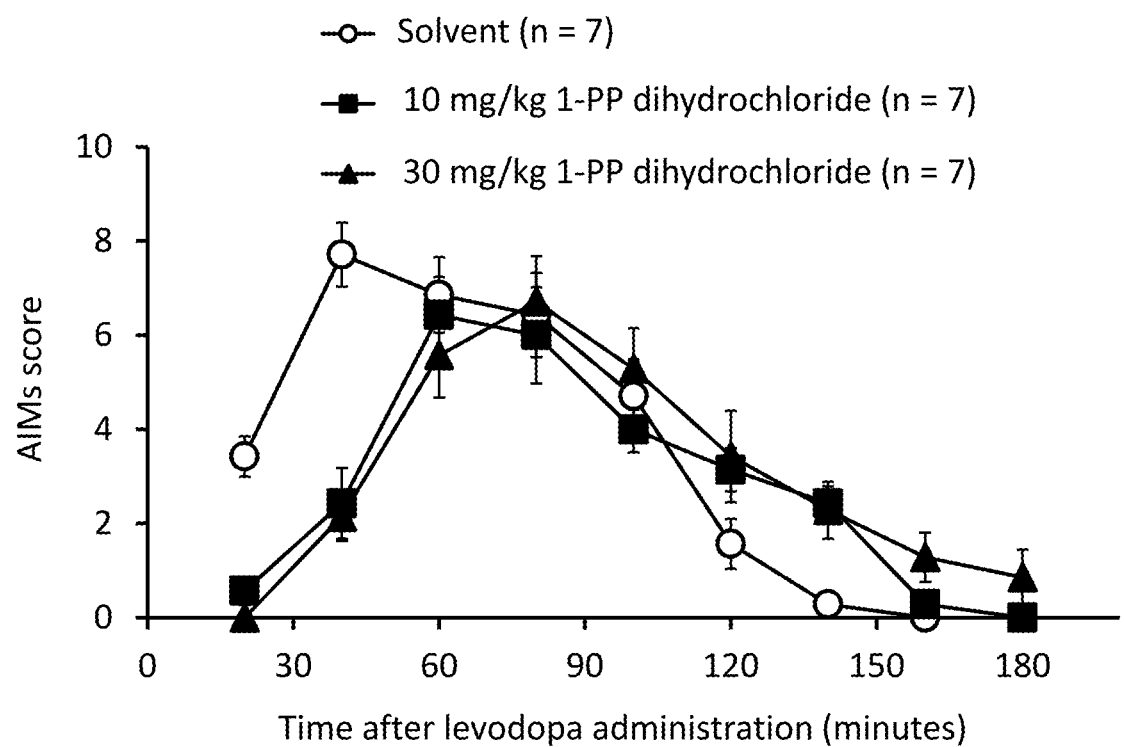
FIG. 10 shows results of evaluating dyskinesia-like symptoms when 1-PP dihydrochloride was subcutaneously administered to PD-LID rat models. Specifically, 1-PP dihydrochloride (10 mg/kg, 30 mg/kg) was subcutaneously administered to PD-LID rat models, and levodopa was administered 5 minutes later to evaluate dyskinesia-like symptoms. Results are indicated in terms of mean value±standard error. In the figure, graph A shows changes in AIMs score over time after levodopa administration. Graph B shows the total AIMs score in 180 minutes. Graph C shows the total AIMs score in 100 to 180 minutes.
Figure 10:
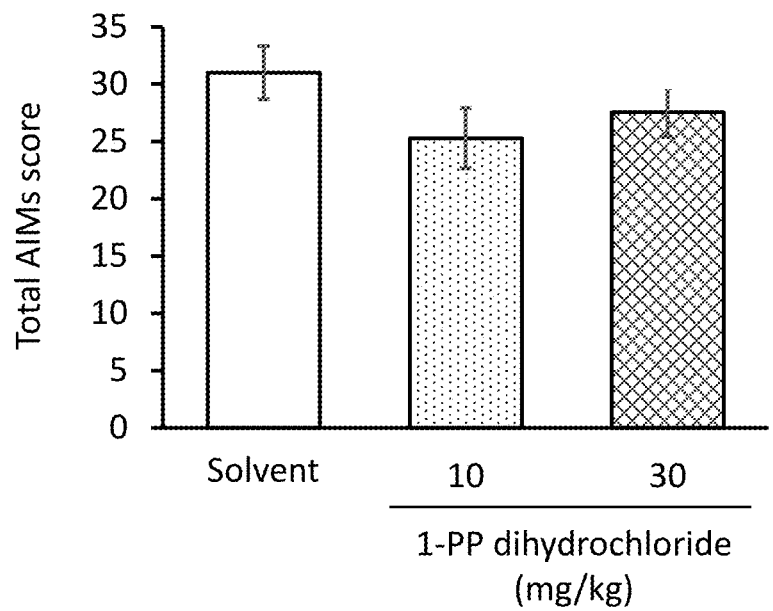
Figure 10:
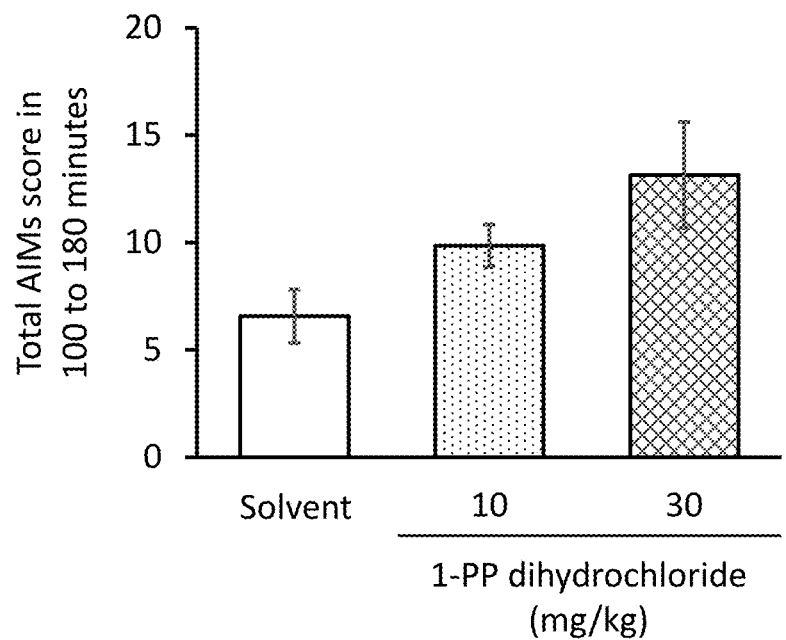

A significant change in the total AIMs score was not found in the 1-PP dihydrochloride (10 or 30 mg/kg) subcutaneous administration group, relative to the solvent administration group (FIG. 10, Graphs A and B).

At 120 to 140 minutes after administration of levodopa, a clear dyskinesia-like symptom (mean AIMs score of 2 or greater) was observed in the 1-PP dihydrochloride subcutaneous administration group (10 or 30 mg/kg). When the solvent administration group and the 1-PP dihydrochloride administration group were compared by using the total AIMs score in 100 to 180 minutes as an indicator, an increasing trend in the total AIMs score, albeit not significant, was observed in the 1-PP dihydrochloride administration group relative to the solvent administration group (FIG. 10, Graph C). The result suggests the potential of tandospirone metabolite 1-PP inducing a rebound symptom of dyskinesia.

The result suggests the potential of a rebound symptom of dyskinesia under administration conditions generating the tandospirone metabolite 1-PP. In other words, for tandospirone, a method of administration that can suppress the generation of 1-PP has less effect on rebound symptoms of dyskinesia and is preferable.

Example 6: Demonstration in Clinical Protocol

The effect of improving PD-LID of the compound of the invention or the combined drug of the invention can be confirmed by a clinical study in accordance with the method described in the following Reference Document 1 (amantadine P3) as clinical study with a suitable design that can evaluate PD-LID (Reference Document 1: JAMA Neurology 2017; 74 (8) 941-949; Reference Document 2: Movement Disorders 2015; 30 (19) 1343-1350).

More specifically, the effect of improving PD-LID can be confirmed by, for example, administering the tandospirone or a pharmaceutically acceptable salt or prodrug thereof of the invention or a combined drug of the invention for a certain dosing period (examples thereof include, but are not limited to, 8 to 12 weeks) in 20 years old or older patients diagnosed as having Parkinson's disease and comparing the period of dyskinesia manifestation based on a patient diary or score such as UPDRS, UDysRS, CDRS, or AIMS before and after the dosing period or the like.

The conditions such as the target patient, dosing period, dosage of agent, and evaluation method can be appropriately changed in the above test.

Example 7: Evaluation of the Dopamine Release Action in the Striatum in PD-LID Animal Models (Test Method)

To measure dopamine release in the striatum, PD-LID rat models were subjected to guide cannula implantation surgery in the striatum and chromatography by the methods described in a reference document (Pharmacol Res Perspect. 2015 June; 3(3): e00142.) On the day of the test, a dialysis probe was inserted into the striatum along the guide cannula. A tape agent was applied to the abdominal regions of rats at 60 cm$^2$/kg (including 6.5% W/V tandospirone free form). After 4 hours from application, a levodopa containing solution was intraperitoneally administered, and dialysate was collected in a sample vial every 10 minutes. The dopamine level in the collected dialysate was measured using an HPLC-ECD system (EiCom). The results in the drawings are indicated in terms of mean value±standard error. Individuals with 50% or more of the tape agent coming off during the test were excluded from analysis. The test results were statistically analyzed by comparison with the placebo tape administration group using t-test. * indicates p<0.05, meaning that there is a significant difference compared to the placebo tape administration group.

(Results)

Figure 11A:
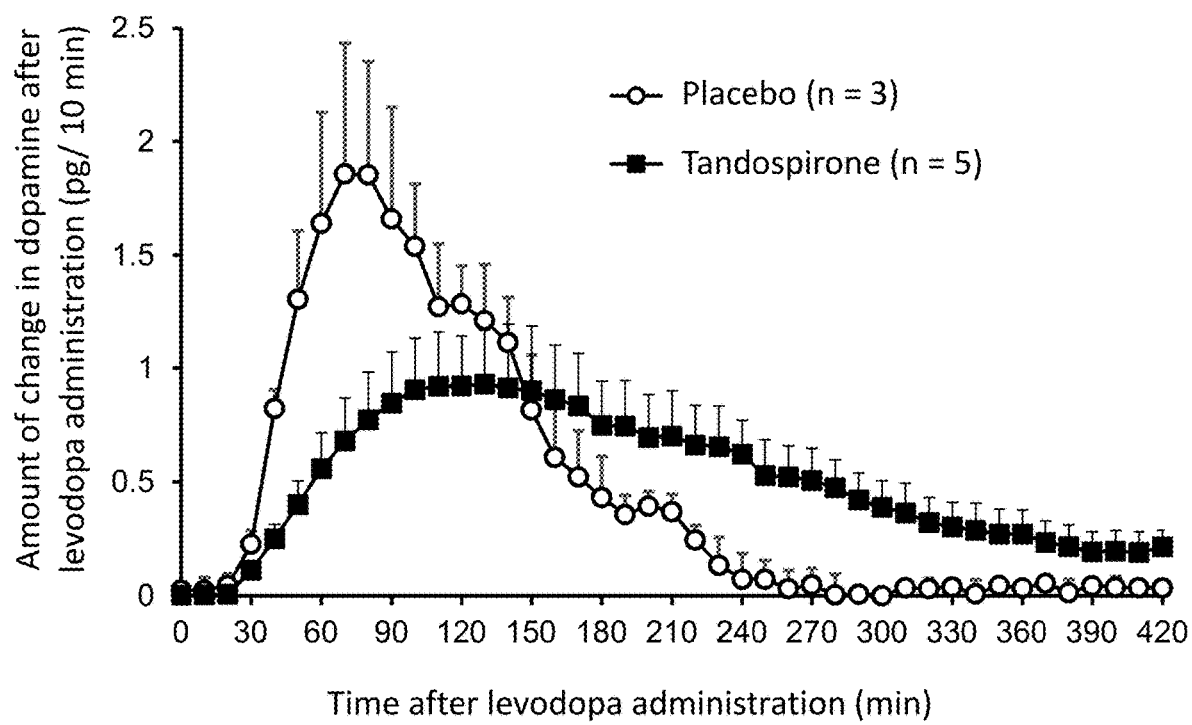
FIG. 11A is the result of intraperitoneally administering levodopa to a PD-LID rat model and measuring the change in the amount of dopamine over time in the striatum by microdialysis.
Figure 11B:
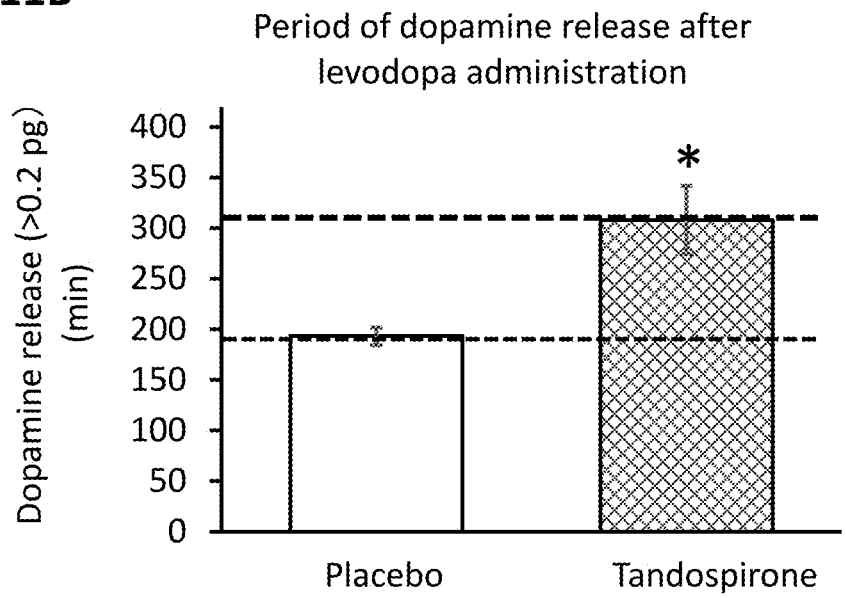
FIG. 11B is the result of computing the time during which the amount of change in released dopamine is 0.2 pg or greater. An effect of prolongation of period of striatum dopamine release relative to the placebo group was observed from application of a tandospirone tape agent.
Figure 11C:
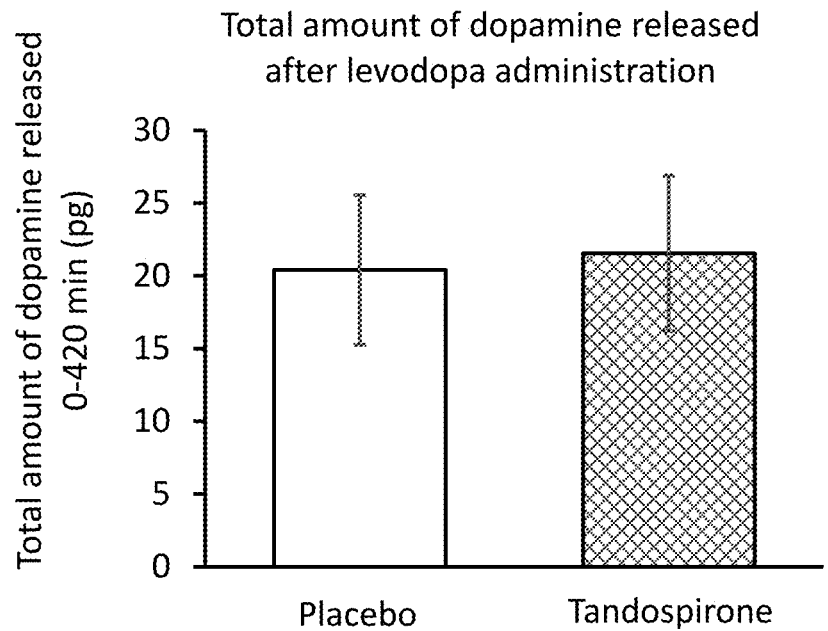
FIG. 11C is the resulting total released dopamine after levodopa administration. A difference in total released dopamine was not found.

The amount of change in dopamine (pg) was measured at every sampling point (every 10 minutes). The amount was calculated as the amount of change from a baseline (mean value of 4 samples before administration of levodopa containing solution), which was calculated up to 420 minutes after administration of levodopa containing solution. A tandospirone tape agent reduced the amount of dopamine released in the striatum from 30 minutes to 150 minutes after levodopa administration, and increased the amount of dopamine released after 150 minutes (FIG. 11A). The period of time during which the amount of change in released dopamine is 0.2 pg or greater was calculated. A significant prolongation was found relative to the placebo tape administration group by applying a tandospirone tape agent (FIG. 11B). Meanwhile, a difference in the total amount of dopamine released after levodopa administration was not found (FIG. 11C).

In view of the above results, a tandospirone tape agent exhibited a sustained action of releasing dopamine in the striatum in PD-LID. Specifically, a tandospirone tape agent was found to exhibit an action of suppressing excessive secretion of dopamine immediately after dopamine administration and maintaining a constant dopamine level in the synaptic cleft of the striatum for an extended period of time by gradually releasing dopamine in PD-LID.

While it is understood that motor complications associated with levodopa therapy for Parkinson's disease have an effect on the rapid increase/decrease in the levodopa level in the synaptic cleft of the striatum, it was found that tandospirone is expected to have an effect of improving PD-LID or motor fluctuations associated with levodopa therapy for Parkinson's disease by suppressing rapid increase/decrease in the dopamine level in the synaptic cleft of the striatum, and has an ideal pharmacological action that can comprehensively treat motor complications.

[Description]

levodopa was administered to a PD-LID rat model and the change in the amount of dopamine was measured over time in the striatum by microdialysis (FIG. 11A).

An effect of prolongation of period of striatum dopamine release relative to the placebo group was observed from application of a tandospirone tape agent (FIG. 11B).

Meanwhile, a difference in total released dopamine after levodopa administration was not found (FIG. 11C).

Example 8: Study in MPTP Induced PD-LID Rhesus Monkey Model

This Example studied the effect of improvement of PD-LID by transdermal administration of tandospirone in a rhesus monkey model with PD-LID induced with 1-methyl-4-phenyl-1,2,3,6-tetrahydropyridine (MPTP) that is used to create a Parkinson's disease animal model.

(Materials and Methods)

MPTP induced Parkinson's disease levodopa induced dyskinesia (PD-LID) rhesus monkey models were created as follows. To male rhesus monkeys (Hamri Co., Ltd.), 0.4 or 0.6 mg/kg of MPTP was administered once or twice a week continuously until Parkinson's disease symptoms manifested stably, and then levodopa (20 or 30 mg/kg) was administered once or twice a week continuously until dyskinesia manifested stably to create PD-LID rhesus monkey models. levodopa/Benserazide (levodopa at 22 mg/kg, and Benserazide at ¼ the weight of levodopa) was orally administered to the PD-LID rhesus monkey models, and dyskinesia symptoms were evaluated every 30 minutes from 5 minutes after administration for 150 minutes. A tandospirone containing paste or a tandospirone free placebo paste was transdermally administered to the monkey models. The back of the rhesus monkeys was shaved. A paste was applied to a 4 cm×10 cm area 19 hours before the test. The paste was covered with a tape and clean fabric, and the monkeys were fitted with a jacket. Dyskinesia was evaluated (dyskinesia score) by analyzing a video capturing the monkey models and giving scores by an evaluator experienced in behavioral evaluation. Dyskinesia scores were evaluated based on Revised non-human primate dyskinesia rating scale (J Neurosci 2001; 21: 6853-6861.) A score of 0 was given if dyskinesia was not observed at all; a score of 1 was given if dyskinesia was observed in less than 30% of the evaluation period, which is deemed as a mild dyskinesia; a score of 2 was given if dyskinesia was observed in 30% or more of the evaluation period but normal behavior was not inhibited, which is deemed as a moderate dyskinesia; a score of 3 was given if dyskinesia was observed in 30% or more and less than 70% of the evaluation period and normal behavior was inhibited, which is deemed as a significant dyskinesia; and a score of 4 was given if dyskinesia was observed in 70% or more of the evaluation period and normal behavior was inhibited, which is deemed as a severe dyskinesia. Systemic dyskinesia was also evaluated as a particularly severe dyskinesia. Systemic dyskinesia was defined as manifestation of dyskinesia at 4 or more of the face, right arm, left arm, body trunk, right leg, and left leg by referring to UDysRS, which is a clinical evaluation scale using dyskinesia by parts in the evaluation. A score of 1 was given if systemic dyskinesia was found in 30% or more of the evaluation period, and a score of 2 was given if systemic dyskinesia was found in 70% or more of the evaluation period.

(Results)

Figure 12A:
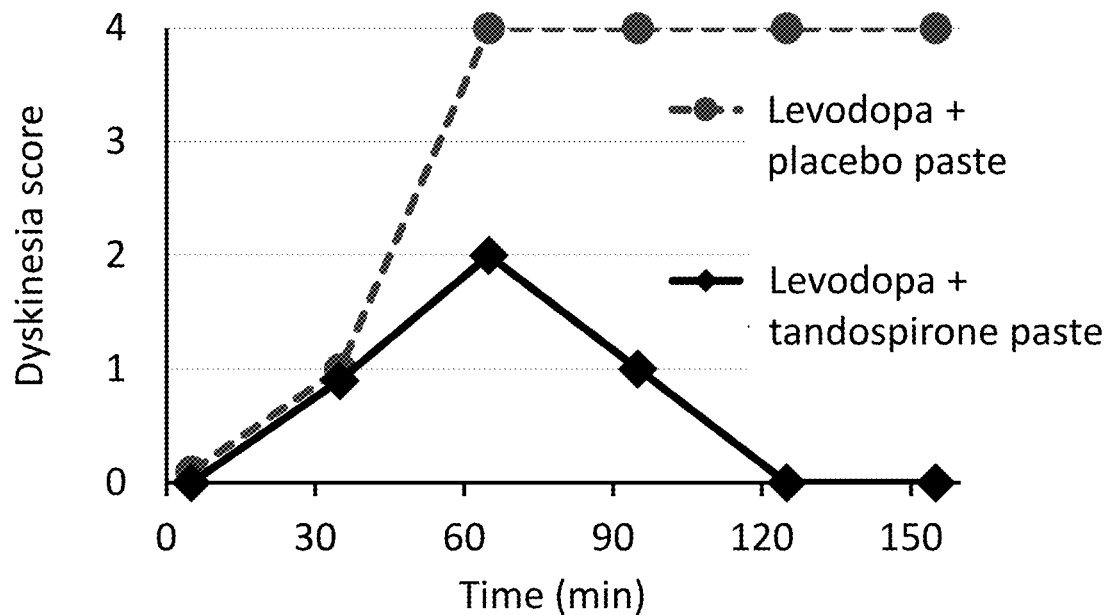
FIGS. 12A-12B show results of orally administering levodopa/Benserazide (levodopa at 22 mg/kg, and Benserazide at ¼ the weight of levodopa) to MPTP induced Parkinson's disease levodopa induced dyskinesia (PD-LID) rhesus monkey model and evaluating dyskinesia symptoms every 30 minutes from 5 minutes after administration for 150 minutes. A tandospirone containing paste or a tandospirone free placebo paste was transdermally administered to monkey models. The back of rhesus monkeys was shaved. A paste was applied to a 4 cm×10 cm area 19 hours before the test. The paste was covered with a tape and clean fabric, and the monkeys were fitted with a jacket. Dyskinesia was evaluated by analyzing a video capturing the monkey models and giving scores by an evaluator experienced in behavioral evaluation. Dyskinesia scores were evaluated based on Revised non-human primate dyskinesia rating scale (J Neurosci 2001; 21: 6853-6861.) A score of 0 was given if dyskinesia was not observed at all; a score of 1 was given if dyskinesia was observed in less than 30% of the evaluation period, which is deemed as a mild dyskinesia; a score of 2 was given if dyskinesia was observed in 30% or more of the evaluation period but normal behavior was not inhibited, which is deemed as a moderate dyskinesia; a score of 3 was given if dyskinesia was observed in 30% or more and less than 70% of the evaluation period and normal behavior was inhibited, which is deemed as a significant dyskinesia; and a score of 4 was given if dyskinesia was observed in 70% or more of the evaluation period and normal behavior was inhibited, which is deemed as a severe dyskinesia. Systemic dyskinesia was also evaluated as a particularly severe dyskinesia. Systemic dyskinesia was defined as manifestation of dyskinesia at 4 or more of face, right arm, left arm, body trunk, right leg, and left leg by referring to UDysRS, which is a clinical evaluation scale using dyskinesia by parts in the evaluation. A score of 1 was given if systemic dyskinesia was found in 30% or more of the evaluation period, and a score of 2 was given if systemic dyskinesia was found in 70% or more of the evaluation period.
Figure 12B:
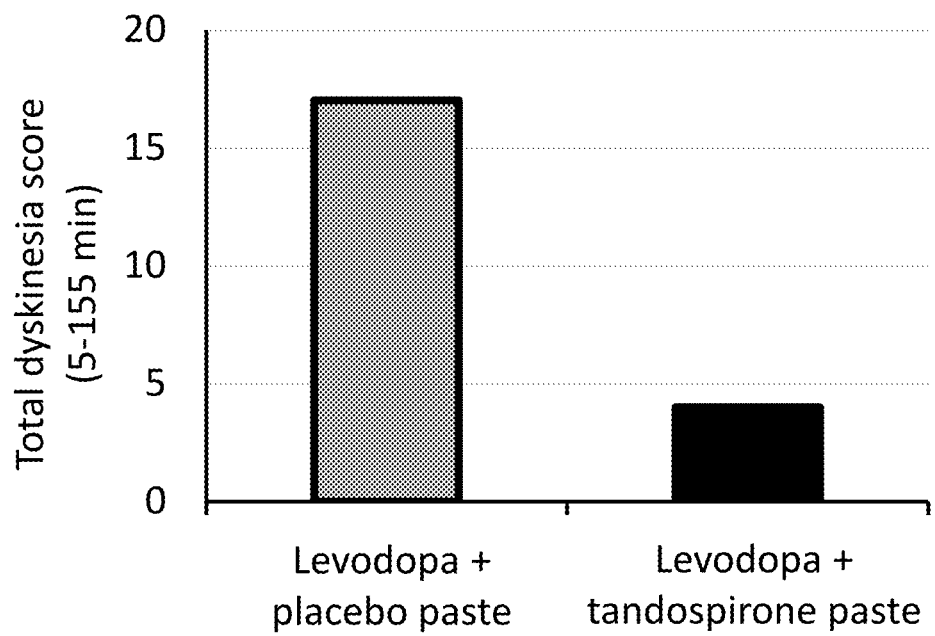

FIGS. 12A-12B show the results of this Example (sustained suppression of development of dyskinesia symptoms in monkey models). Levodopa/Benserazide (levodopa at 22 mg/kg, and Benserazide at ¼ the weight of levodopa) was orally administered to the PD-LID rhesus monkey models, and dyskinesia symptoms (dyskinesia score) were evaluated every 30 minutes from 5 minutes after levodopa/Benserazide administration for 155 minutes. A dyskinesia score of 4 was exhibited at 65 to 155 minutes after levodopa/Benserazide administration with placebo paste administration, while sustained suppression of the dyskinesia score was observed with administration of tandospirone containing paste (FIG. 12A). The total dyskinesia score during 155 minutes after levodopa/Benserazide administration was suppressed 76.5% (FIG. 12B).

Example 9: Evaluation of Tandosprone's Action of Prolonging ON-Time of Levodopa in Parkinson's Disease Animal Model This Example evaluated tandosprone's antiparkinsonian action time, i.e., "ON-time", of levodopa using various routes of administration in Parkinson's disease animal models.

A rat striatum dopaminergic denervation model using topical administration of 6-hydroxydopamine (hereinafter, also referred to as "6-OHDA") to one side of the brain is known as a typical experimental model for Parkinson's disease (rats treated on one side with 6-OHDA (6-OHDA-lesioned rats)). It is known that said model exhibits a rotational behavior to the opposite side from the site of injection of 6-OHDA due to a therapeutic drug for Parkinson's disease, which activates the intracerebral dopaminergic nervous system, such as levodopa or dopamine receptor agonist. The usefulness of a therapeutic drug for Parkinson's disease can be evaluated using such a rotational behavior as an indicator. Since prolongation of rotational behavior time by levodopa can be interpreted as leading to prolongation of ON-time in Parkinson's disease (improvement in motor fluctuations), prolongation in levodopa induced rotational behavior time was evaluated by using this model.

(Testing Method: Preparation of Animal Model)

Wistar male rats (12-week old, Japan SLC, Inc.) were used for the preparation of animal models. Desipramine hydrochloride (25 mg/kg; Wako Pure Chemical) was intraperitoneally administered. After 30 minutes from the administration, the rats were subjected to isoflurane inhalational anesthetic using a general anesthesia apparatus for experimental animals. Under isoflurane anesthesia, the rats were immobilized to a brain stereotaxic instrument. The skin on the head was incised with a surgical scalpel to expose the skull. The coordinates of the bregma used as the origin (AP: 0, ML: 0, DV: 0) was determined, and the coordinates of the right medial forebrain bundle (AP: −4.4 mm, ML: 1.5 mm, DV: 7.8 mm from bregma) were measured. After inserting an injection tube for administration at the measured coordinates, 6-OHDA (9 µg/4 µL; Sigma-Aldrich) inducing dopaminergic denervation was topically injected. After 2 weeks from surgery, apomorphine hydrochloride hemihydrate (0.5 mg/kg; Wako Pure Chemical) was subcutaneously administered, and the rotation movement to the opposite side from the 6-OHDA injected site was observed. Rats with 7 rotations or more per minute were used as rats treated on one side with 6-OHDA.

(Oral Administration)

Tandospirone citrate (suspended in 0.5% methyl cellulose solution) or a solvent (0.5% methyl cellulose solution) was orally administered 5 minutes before observation of rotational behavior to rats treated on one side with 6-OHDA. Levodopa methyl ester hydrochloride (5 mg/kg in levodopa free form) comprising benserazide at ¼ the amount of levodopa in terms of free form concentration was intraperitoneally administered. Benserazide is an agent that is known to suppress the metabolism of levodopa in the periphery, increase the blood levodopa concentration, and increase the intracranial penetration of levodopa. The number of rotations to the opposite side from the site of injection of 6-OHDA was counted for 180 minutes from immediately after the intraperitoneal administration, and the count was tallied in 5 minute increments. The results in the drawings are indicated in terms of mean value±standard error. As the ON-time of each individual, the total value of measured time for 5 minute increments exhibiting a rotation tally that is 20% or more of the peak value of the rotation tally for 5 minute increments in the individual was calculated. The test results were statistically analyzed by comparison with the solvent administration group using the Steel test. * indicates $p<0.05$ and ** indicates $p<0.01$, meaning that there is a significant difference.

(Transdermal Administration)

For evaluation of a tape agent, the abdominal regions of the rats were shaved prior to the evaluation date. The tape agent was applied to the abdominal regions of the rats on the evaluation date at 60 cm$^2$/kg (including 6.5% W/V tandospirone free form). After 4 minutes from application, levodopa methyl ester hydrochloride (5 mg/kg in levodopa free form) comprising benserazide at ¼ the amount of levodopa in terms of free form concentration was intraperitoneally administered. The number of rotations to the opposite side from the site of injection of 6-OHDA was counted for 180 minutes from immediately after the intraperitoneal administration, and the count was tallied in 5 minute increments. The results in the drawings are indicated in terms of mean value±standard error. Individuals with 50% or more of the tape agent coming off during the test were excluded from analysis. As the ON-time of each individual, the total value of measured time for 5 minute increments exhibiting a rotation tally that is 20% or more of the peak value of the rotation tally for 5 minute increments in the individual was calculated. The test results were statistically analyzed by comparison with the solvent administration group using the Steel test. ** indicates $p<0.01$, meaning that there is a significant difference.

(Transdermal Administration: Stripping Conditions)

When evaluating a tape agent under stratum corneum stripping conditions (tandospirone high exposure conditions), stripping was performed 10 times at the abdominal region of rats using a transpore surgical tape (3M) on the evaluation date, and a tape agent was then applied at 60 cm$^2$/kg (including 6.5% W/V tandospirone free form).

(Results)

Figure 13A:
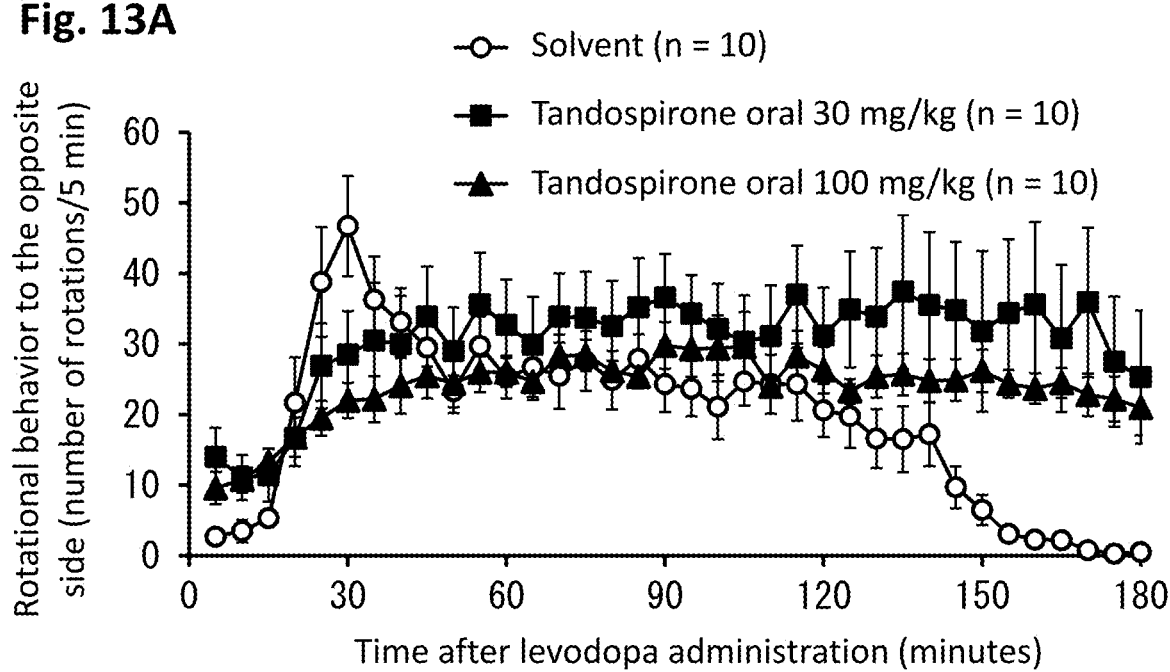
FIGS. 13A-13B shows results of measuring the ON-time (antiparkinsonian action effective time associated with levodopa therapy of Parkinson's disease) by measuring for 180 minutes the rotational behavior (total number of rotations in 5 minutes) after levodopa administration to Parkinson's disease rat models (6-OHDA-lesioned rats) by oral administration of tandospirone citrate. ON-time was defined as the period of time exhibiting a number of rotations that is 20% or greater of the peak value of the total number of rotations in 5 minutes from levodopa administration. Prolongation of ON-time was observed at 120 minutes to 180 minutes after levodopa administration (FIG. 13A) and a significant prolongation of total ON-time was observed to 180 minutes (FIG. 13B) relative to the solvent administration group by oral administration of tandospirone citrate (30 mg/kg and 100 mg/kg as citrate concentration).
Figure 13B:
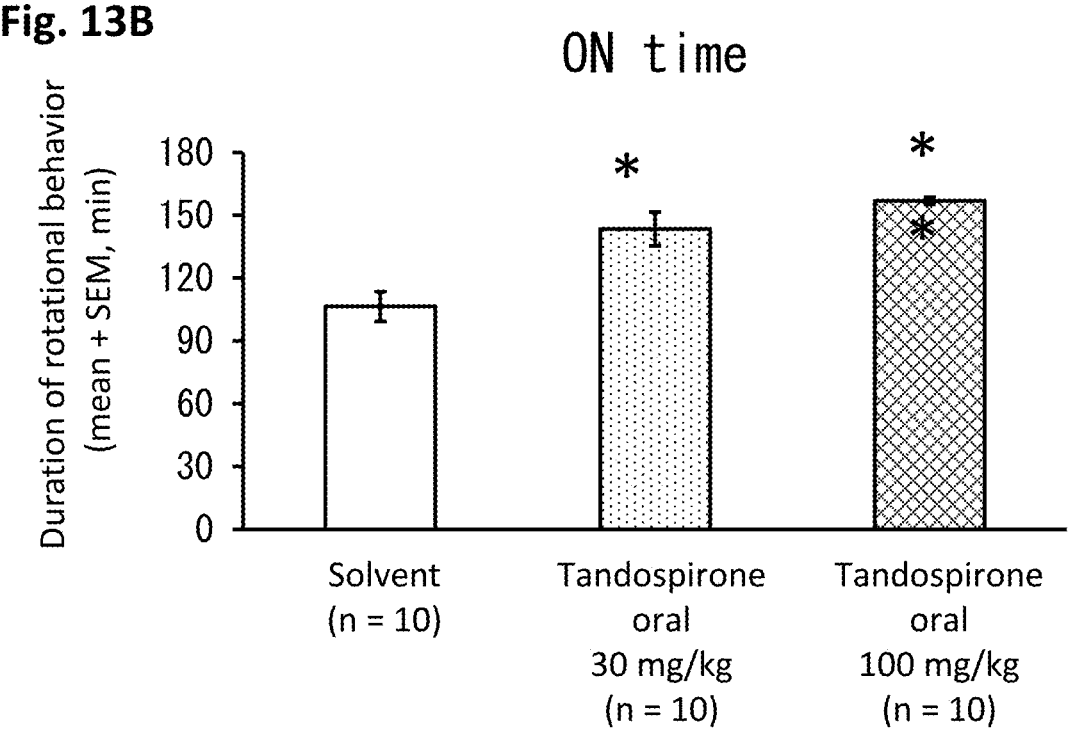
Figure 14A:
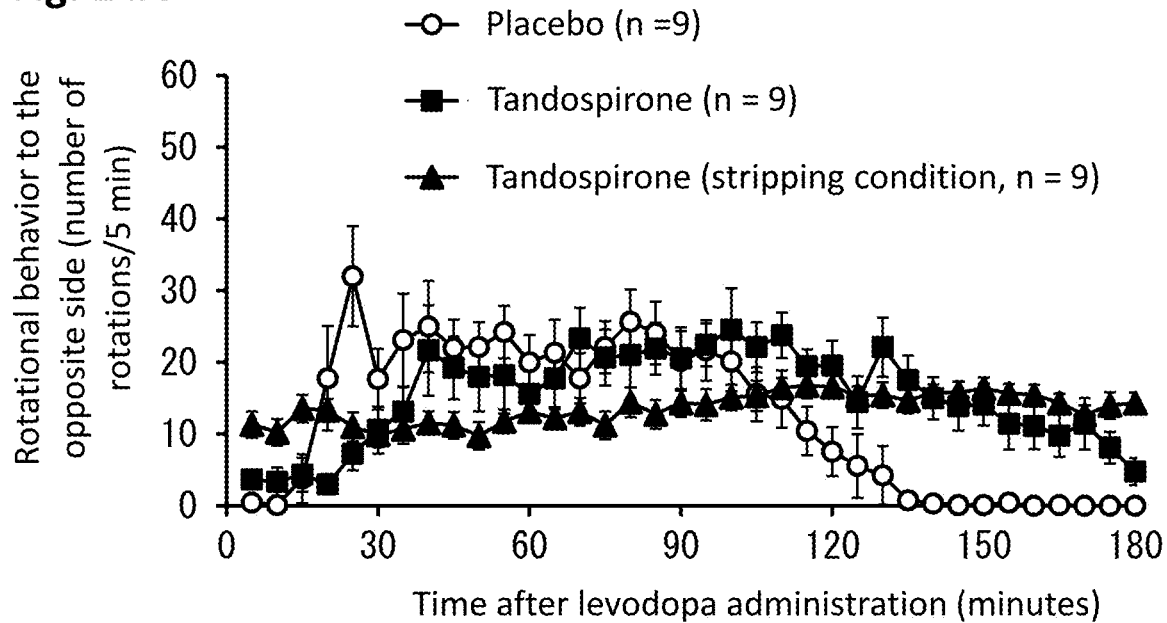
FIGS. 14A-14B show results of measuring the ON-time by measuring, for 180 minutes, the rotational behavior (total number of rotations in 5 minutes) after levodopa administration to Parkinson's disease rat models (6-OHDA-lesioned rats) by transdermal administration (with or without stripping) of tandospirone. ON-time was defined as the period of time exhibiting a number of rotations that is 20% or greater of the peak value of the total number of rotations in 5 minutes from levodopa administration. Prolongation of ON-time was observed at 120 minutes to 180 minutes after levodopa administration (FIG. 14A) and a significant prolongation of total ON-time was observed to 180 minutes (FIG. 14B) relative to the solvent administration group by applying a tandospirone tape agent (60 cm$^2$/kg (including 6.5% W/V tandospirone free form)).
Figure 14B:
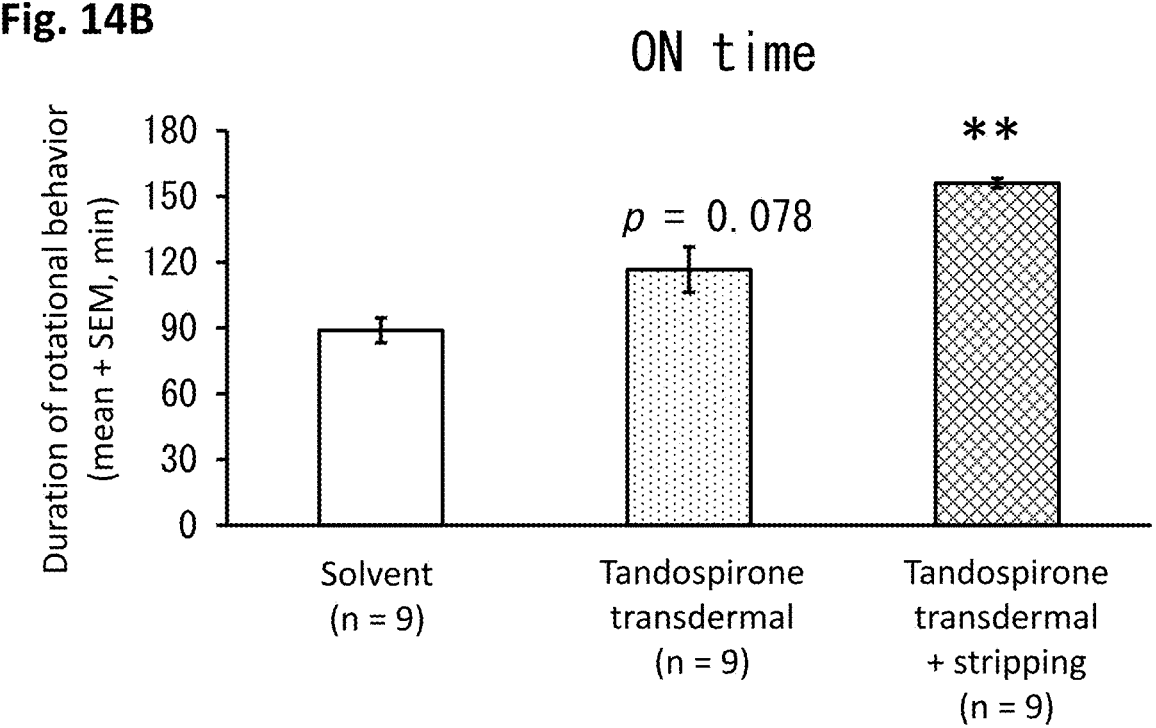

Prolongation of ON-time was observed at 120 minutes to 180 minutes after levodopa administration (FIG. 13A) and a significant prolongation of ON-time was observed to 180 minutes (FIG. 13B) relative to the solvent administration group by oral administration of tandospirone citrate (30 mg/kg and 100 mg/kg). Prolongation of ON-time was observed at 120 minutes to 180 minutes after levodopa administration (FIG. 14A) and a significant prolongation of ON-time was observed to 180 minutes (FIG. 14B) relative to the placebo tape administration group by applying a tandospirone tape agent (with/without stripping condition).

In view of the above results, tandospirone exhibited the same ON-time prolongation action by different administration methods of oral administration and transdermal administration.

Example 10: Clinical Test on Pharmacokinetics of Tandospirone Tape Agent

This Example tested and analyzed the pharmacokinetics such as blood concentration of tandospirone in a clinical test.

(Materials and Methods)

This Example performed measurement, prediction and analysis on plasma tandospirone concentration based on the following method.

(1) A single 24-hour dose of tandospirone tape agent (free form content of 4.4 mg, 8.8 mg, and 17.6 mg) was transdermally administered to the pectoral region of 9 healthy Japanese male subjects, and the plasma tandospirone concentration was measured.

(2) For 35.2 mg, 88 mg, and 176 mg, the plasma tandospirone concentration was predicted based on the results for 17.6 mg. The steady state plasma tandospirone concentration was also predicted using Phoenix® WinNonlin® (Certara).

(Formulations Used)

As the tandospirone tape agent, an acrylic adhesive tape agent, which has a sheet-like structure consisting of three layers (a support, adhesive layer, and a detachable film (liner)) and comprises tandospirone (free form) as an active ingredient, was used. The amount of drug penetration from a 24 hour application was about ⅓ to ½ of the tandospirone free form content (drug dosage) in the tape agent. Although not wishing to be bound by any theory, it is understood in the art that if the amount of drug penetration upon 24 hour application is the same, any tape agent can achieve a similar plasma tandospirone concentration as the present Example.

(Results)

FIGS. 15A to 17B show the results of this Example (plasma tandospirone concentration and prediction under steady state). This data is based on preliminary analysis results.

Figure 15A:
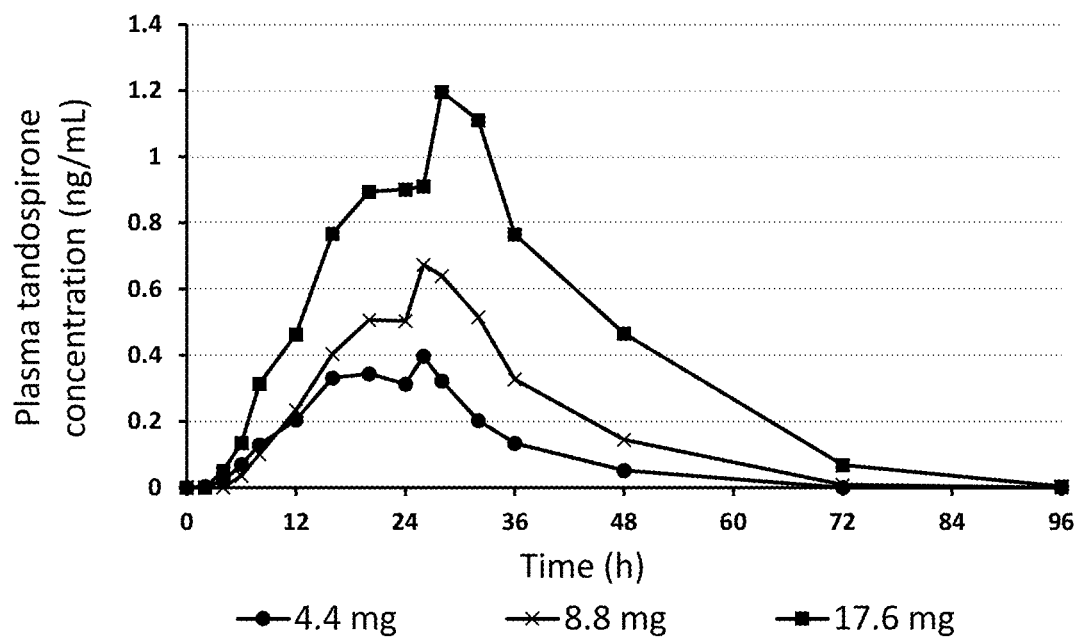
FIG. 15A shows results in Example 10, which shows the change in the concentration of plasma tandospirone free form upon transdermal administration of a single 24-hour dose of a tandospirone tape agent (mean value).
Figure 15B:
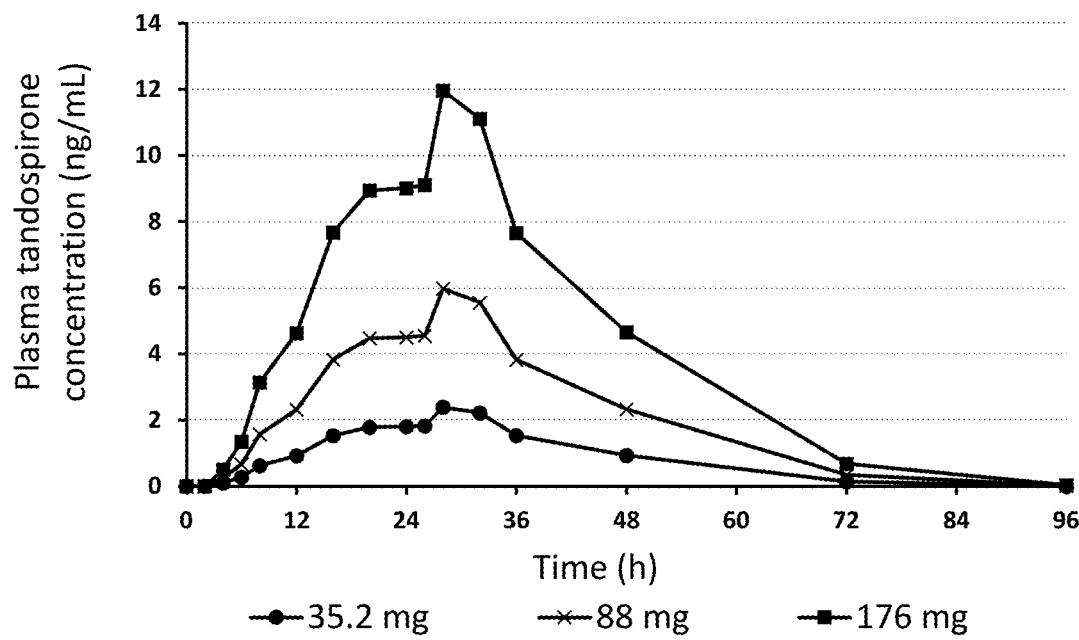
FIG. 15B shows values of prediction and analysis from actual measurement values for 17.6 mg.

FIGS. 15A-15B shows the change in the concentration of plasma tandospirone upon transdermal administration of a single 24-hour dose of a tandospirone tape agent used in this Example (mean value) (the plasma tandospirone concentration is a concentration as a tandospirone free form). FIG. 15A shows the actual measurement value based on a preliminary analysis result for plasma tandospirone concentrations for 4.4 mg, 8.8 mg, and 17.6 mg. FIG. 15B shows values of prediction and analysis from actual measurement values for 17.6 mg.

Figure 16A:
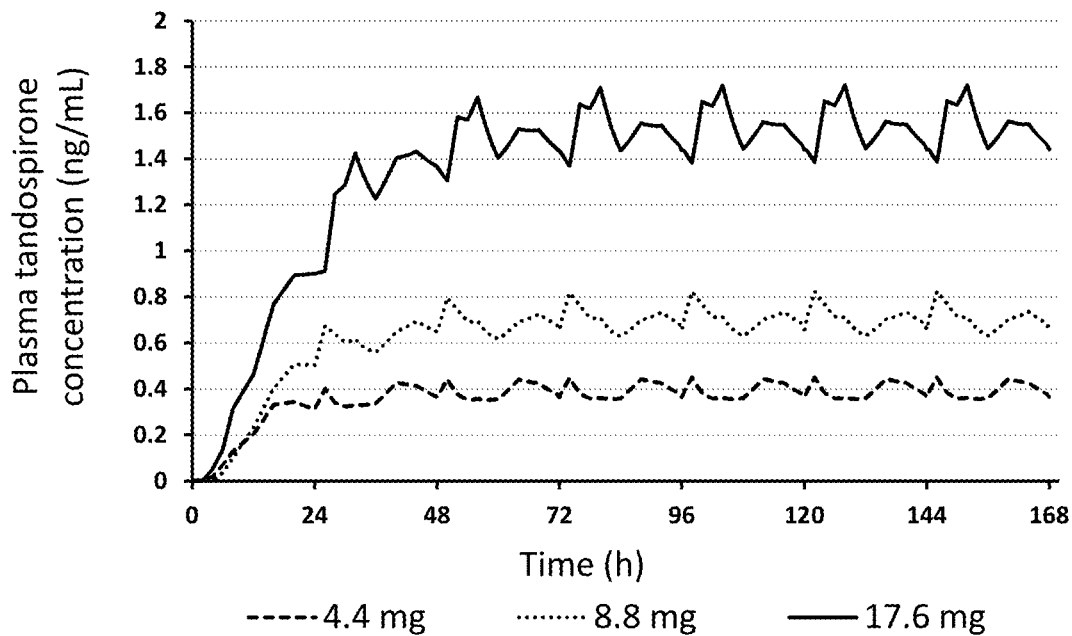
FIGS. 16A-16B also show results in Example 10, which shows a predicted value for the change in the concentration of plasma tandospirone upon once daily repeated transdermal administration of a tandospirone tape agent.
Figure 16B:
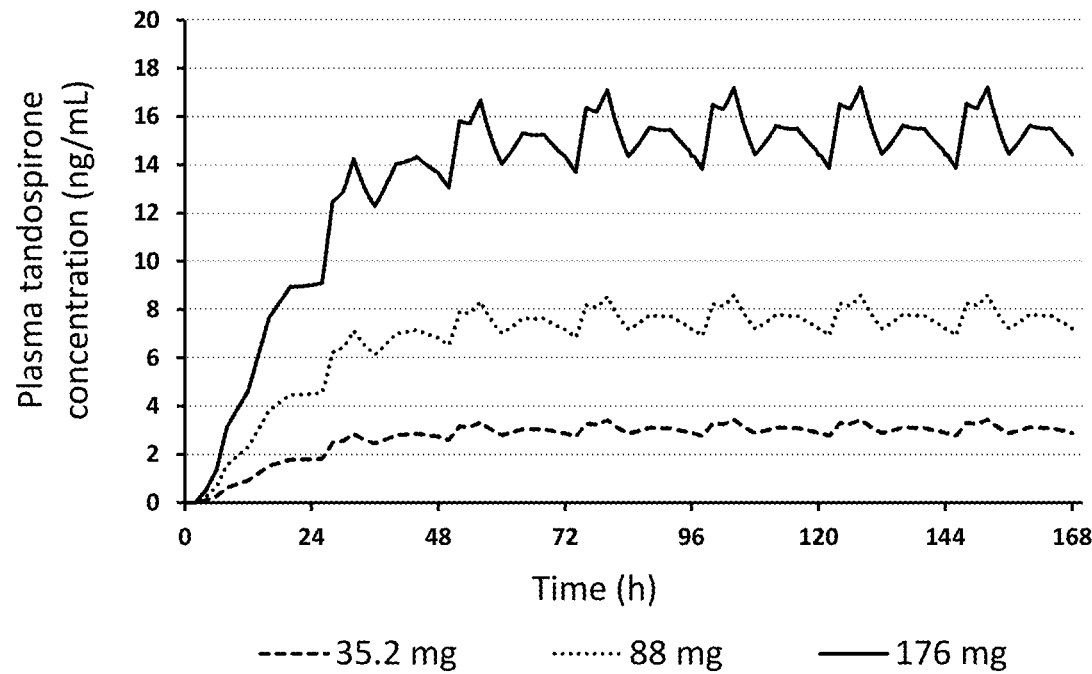

FIGS. 16A-16B show a predicted value for the change in the concentration of plasma tandospirone upon once daily repeated transdermal administration of a tandospirone tape agent of this Example. The results shown in FIG. 16A show values predicted based on the plasma tandospirone concentrations upon a 24-hour single administration of 4.4 mg, 8.8 mg, and 17.6 mg. The results shown in FIG. 16B show values predicted based on the plasma tandospirone concentration upon a 24-hour single administration of 17.6 mg.

Figure 17A:
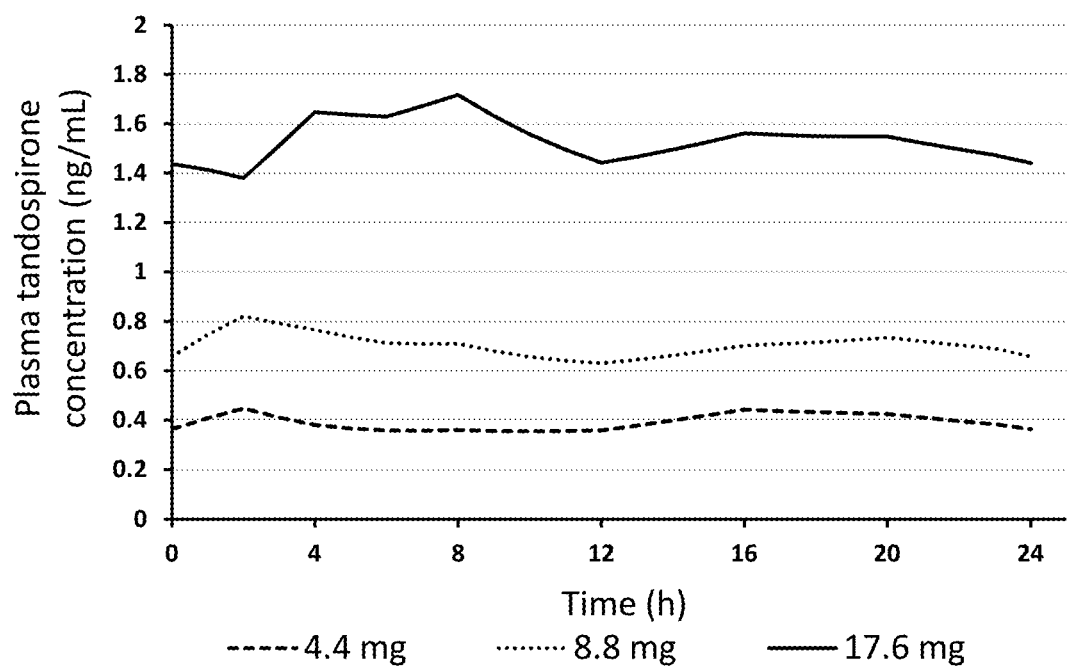
FIGS. 17A-17B also show results in Example 10, which shows a predicted value for the change in the concentration of plasma tandospirone in a steady state upon once daily repeated transdermal administration of a tandospirone tape agent.
Figure 17B:
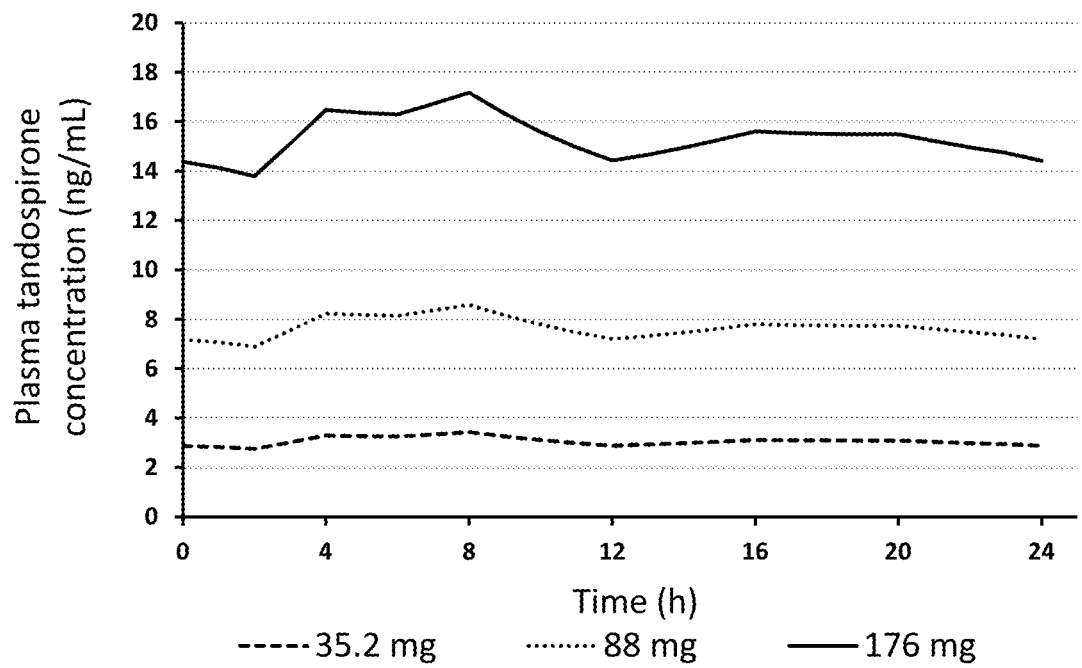

FIGS. 17A-17B shows a predicted value for the change in the concentration of plasma tandospirone in a steady state upon once daily repeated transdermal administration of a tandospirone tape agent in this Example. FIG. 17A is a prediction based on the plasma tandospirone concentration upon a 24-hour single administration of 4.4 mg, 8.8 mg, and 17.6 mg. FIG. 17B is a prediction based on the plasma tandospirone concentration upon a 24-hour single administration of 17.6 mg.

(Discussion)

It is understood that motor fluctuations can be suppressed by using a daily dose (drug dosage per day) of 4 mg to 180 mg of active ingredient.

(Note)

As disclosed above, the present invention is exemplified by the use of its preferred embodiments. However, it is understood that the scope of the present invention should be interpreted solely based on the Claims. It is also understood that any patent, any patent application, and any other references cited herein should be incorporated herein by reference in the same manner as the contents are specifically described herein.

INDUSTRIAL APPLICABILITY

A parenterally administered tandospirone formulation is useful as a therapeutic drug that improves PD-LID.

What is claimed is:

1. A method for treating, improving, or delaying progression of dyskinesia in a subject, comprising transdermally or subcutaneously administering to the subject an effective amount of tandospirone or a pharmaceutically acceptable salt thereof, wherein the tandospirone or the pharmaceutically acceptable salt thereof is administered so that a human blood (plasma) tandospirone concentration is 0.1 to 15 ng/mL for 12 hours or longer per day; and/or 0.1 to 15 ng/mL for 8 to 16 hours after administration of the tandospirone or the pharmaceutically acceptable salt thereof.

2. The method according to claim 1, wherein the subject is suffering from Parkinson's disease.

3. The method according to claim 1, wherein the subject is subject to a drug therapy of Parkinson's disease.

4. The method according to claim 1, wherein the subject is subject to a drug therapy of Parkinson's disease, wherein the drug therapy is at least one selected from the group consisting of Parkinson's disease drug therapy; dopamine replacement therapies and Parkinson's disease adjunct.

5. The method according to claim 1, wherein dopamine amount in striatal synaptic cleft of the subject is sustainably maintained and/or suppressing rapid changes.

6. The method according to claim 1, wherein a levodopa-evoked synaptic dopamine fluxes in a striatum of the subject using $^{11}$C-raclopride Positron Emission Tomography (PET) test is sustainably maintained, and/or suppressing rapid changes and/or intermittent domain receptor stimulation is suppressed.

7. The method of claim 1, wherein the transdermal or subcutaneous administration comprises transdermal administration.

8. The method of claim 1, wherein the dyskinesia comprises at least one of the group consisting of peak-dose dyskinesia, diphasic dyskinesia, and a combination thereof.

9. The method of claim 1, wherein the treatment, improvement, or delay of progression of dyskinesia comprises improvement, or delay of progression of a dyskinesia symptom, reduction of a period of PD-LID manifestation, or a combination thereof.

10. The method of claim 9, wherein the improvement of a dyskinesia symptom is a clinically significant improvement or greater.

11. The method of claim 9, wherein the improvement of a dyskinesia symptom is to a sufficient level to attain a clinical effect.

12. The method of claim 1, wherein the tandospirone or the pharmaceutically acceptable salt thereof is provided as a transdermally administered formulation.

13. The method of claim 1, wherein the tandospirone or the pharmaceutically acceptable salt thereof is provided as an adhesive formulation.

14. The method of claim 12, wherein the transdermally administered formulation is a tape/patch.

15. The method of claim 1, wherein a drug dosage of the tandospirone or the pharmaceutically acceptable salt thereof is 0.1 to 100 mg per day as a free form of tandospirone.

16. The method of claim 1, wherein an amount of drug penetration for the tandospirone or the pharmaceutically acceptable salt thereof is 0.1 to 20 mg per day as a free form of tandospirone.

17. The method of claim 1, wherein the tandospirone or the pharmaceutically acceptable salt thereof is provided as a transdermally administered formulation, and a total applied area per dose is 1 to 100 cm$^2$.

18. The method of claim 1, wherein the human blood (plasma) tandospirone concentration is 1 to 12 ng/mL.

19. The method of claim 1, wherein the human blood (plasma) tandospirone concentration is 2 to 10 ng/mL.

20. The method of claim 1, wherein the tandospirone or the pharmaceutically acceptable salt thereof is an adjunct of levodopa.

21. The method of claim 1, wherein the tandospirone or the pharmaceutically acceptable salt thereof is used with levodopa as a fixed-dose combination or concomitantly as separate formulations.

22. The method according to claim 1, wherein the method further improves motor fluctuations in the subject.

23. The method according to claim 22, wherein the motor fluctuations comprise at least one of the group consisting of a wearing-off phenomenon, an on-off phenomenon, a no-on phenomenon, a delayed on phenomenon, and a combination thereof.

24. The method according to claim 22, wherein treatment, improvement, or delay of progression of the motor fluctuations comprises prolongation of an antiparkinsonian action effective time (ON-time), a reduction of a non-response time (OFF-time), or a combination thereof.

25. The method of claim 1, wherein the tandospirone or the pharmaceutically acceptable salt thereof is administered so that a maximum blood concentration of human blood (plasma) tandospirone in a steady state is 1 to 15 ng/mL, and a ratio of a minimum concentration, with respect to the maximum concentration of human blood (plasma) tandospirone concentration as 100%, is 30 to 95% after administration of the tandospirone or the pharmaceutically acceptable salt thereof.

26. The method of claim 1, wherein the tandospirone or the pharmaceutically acceptable salt thereof is administered so that a maximum blood concentration of human blood (plasma) tandospirone in a steady state is 2 to 12 ng/mL, and a ratio of a minimum concentration, with respect to the maximum concentration of human blood (plasma) tandospirone concentration as 100%, is 30 to 95% after administration of the tandospirone or the pharmaceutically acceptable salt thereof.

27. The method according to claim 4, wherein the Parkinson's disease drug therapy or the dopamine replacement therapies comprises at least one of levodopa therapy, a therapy with levodopa metabolism enzyme inhibitor and dopamine receptor agonist.

28. The method of claim 6, wherein the tandospirone or the pharmaceutically acceptable salt thereof is administered so that an amount of change in striatal [$^{11}$C] raclopride receptor binding from before levodopa administration to 1 hour after administration (amount of change B/1 h) is less than 10% after administering the tandospirone or a pharmaceutically acceptable salt thereof.

29. The method of claim 6, wherein the tandospirone or the pharmaceutically acceptable salt thereof is administered so that a ratio of change B/1 h in the amount of striatal [$^{11}$C] raclopride receptor binding is 90% or less.

\* \* \* \* \*